(12) United States Patent
Abraham et al.

(10) Patent No.: US 12,263,478 B2
(45) Date of Patent: Apr. 1, 2025

(54) MOLECULAR DIAGNOSTIC DEVICES WITH DIGITAL DETECTION CAPABILITY AND WIRELESS CONNECTIVITY

(71) Applicant: Visby Medical, Inc., San Jose, CA (US)

(72) Inventors: Teresa Abraham, Washington, DC (US); Victor Briones, Gilroy, CA (US); Brian Ciopyk, Santa Clara, CA (US); Paul Dentinger, Sunol, CA (US); Kamal Kajouke, San Jose, CA (US); Bryan D. Knysh, Toronto (CA); Brandon Ma, Santa Clara, CA (US)

(73) Assignee: Visby Medical, Inc., San Jose, CA (US)

( * ) Notice: Subject to any disclaimer, the term of this patent is extended or adjusted under 35 U.S.C. 154(b) by 828 days.

(21) Appl. No.: 17/606,669

(22) PCT Filed: Apr. 28, 2020

(86) PCT No.: PCT/US2020/030307
§ 371 (c)(1),
(2) Date: Oct. 26, 2021

(87) PCT Pub. No.: WO2020/223257
PCT Pub. Date: Nov. 5, 2020

(65) Prior Publication Data
US 2022/0203365 A1    Jun. 30, 2022

Related U.S. Application Data

(60) Provisional application No. 62/957,068, filed on Jan. 3, 2020, provisional application No. 62/839,724, filed on Apr. 28, 2019.

(51) Int. Cl.
*B01L 3/00* (2006.01)
*C12Q 1/6825* (2018.01)
(Continued)

(52) U.S. Cl.
CPC ...... *B01L 3/502715* (2013.01); *C12Q 1/6825* (2013.01); *G16B 20/00* (2019.02);
(Continued)

(58) Field of Classification Search
CPC ............ B01L 2200/16; B01L 2300/04; B01L 2300/0663; B01L 2300/0809;
(Continued)

(56) References Cited

U.S. PATENT DOCUMENTS 5,498,392 A   3/1996  Wilding et al.
5,631,165 A   5/1997  Chupp et al.
(Continued)

FOREIGN PATENT DOCUMENTS

CN    108371961    8/2018
EP    2682480 A1   1/2014
(Continued)

OTHER PUBLICATIONS

International Search Report and Written Opinion for PCT/US2020/030307, mailed Jul. 23, 2020.
(Continued)

*Primary Examiner* — Jennifer Wecker
(74) *Attorney, Agent, or Firm* — Mills IP Law, PLLC

(57) ABSTRACT

In some embodiments, a stand-alone molecular diagnostic test device includes a detection circuit that includes a light emitting device and a light receiving device (e.g., a photodiode) that are arranged to produce an electronic signal associated with a colorimetric output produced by the stand-alone molecular diagnostic test.

25 Claims, 32 Drawing Sheets

(51) Int. Cl.
  *G16B 20/00* (2019.01)
  *G16B 25/20* (2019.01)
  *G16B 40/10* (2019.01)
(52) U.S. Cl.
  CPC .............. *G16B 25/20* (2019.02); *G16B 40/10* (2019.02); *B01L 2200/16* (2013.01); *B01L 2300/04* (2013.01); *B01L 2300/0663* (2013.01); *B01L 2300/0809* (2013.01)
(58) Field of Classification Search
  CPC ... B01L 3/502715; B01L 7/52; C12Q 1/6825; C12Q 1/6834; C12Q 2563/103; C12Q 2563/125; C12Q 2565/501; C12Q 2565/629; G01N 2021/6439; G01N 21/76; G01N 21/78; G16B 20/00; G16B 25/20; G16B 40/10
  See application file for complete search history.

(56) References Cited

U.S. PATENT DOCUMENTS

| | | |
|---|---|---|
| 5,726,026 A | 3/1998 | Wilding et al. |
| 5,882,903 A | 3/1999 | Andrevski et al. |
| 5,922,591 A | 7/1999 | Anderson et al. |
| 5,952,664 A | 9/1999 | Wake et al. |
| 6,126,804 A | 10/2000 | Andresen |
| 6,146,591 A | 11/2000 | Miller |
| 6,153,425 A | 11/2000 | Kozwich et al. |
| 6,235,479 B1 | 5/2001 | Rogers |
| 6,249,593 B1 | 6/2001 | Chu et al. |
| 6,313,471 B1 | 11/2001 | Giebeler et al. |
| 6,369,893 B1 | 4/2002 | Christel et al. |
| 6,374,684 B1 | 4/2002 | Dority |
| 6,645,758 B1 | 11/2003 | Schnipelsky et al. |
| 6,780,617 B2 | 8/2004 | Chen |
| 6,893,879 B2 | 5/2005 | Petersen et al. |
| 7,156,809 B2 | 1/2007 | Quy |
| 7,189,522 B2 | 3/2007 | Esfandiari |
| 7,297,313 B1 | 11/2007 | Northrup et al. |
| 7,384,782 B2 | 6/2008 | Nakatani et al. |
| 7,416,892 B2 | 8/2008 | Battrell et al. |
| 7,553,675 B2 | 6/2009 | Jerome et al. |
| 7,569,382 B2 | 8/2009 | Li |
| 7,579,172 B2 | 8/2009 | Cho et al. |
| 7,592,139 B2 | 9/2009 | West et al. |
| 7,648,835 B2 | 1/2010 | Breidford et al. |
| 7,705,339 B2 | 4/2010 | Smith et al. |
| 7,754,452 B2 | 7/2010 | Kim et al. |
| 7,767,439 B2 | 8/2010 | Oh et al. |
| 7,799,521 B2 | 9/2010 | Chen et al. |
| 7,914,986 B2 | 3/2011 | Nunn |
| 7,985,716 B2 | 7/2011 | Yershov et al. |
| 7,998,757 B2 | 8/2011 | Darrigrand et al. |
| 8,018,593 B2 | 9/2011 | Tan et al. |
| 8,048,386 B2 | 11/2011 | Dority et al. |
| 8,088,616 B2 | 1/2012 | Handique |
| 8,110,392 B2 | 2/2012 | Battrell et al. |
| 8,133,671 B2 | 3/2012 | Williams et al. |
| 8,133,703 B2 | 3/2012 | Ching et al. |
| 8,145,431 B2 | 3/2012 | Kloepfer et al. |
| 8,169,610 B2 | 5/2012 | Oldham et al. |
| 8,173,077 B2 | 5/2012 | Korampally et al. |
| 8,187,557 B2 | 5/2012 | Van Atta et al. |
| 8,198,074 B2 | 6/2012 | Moriwaki et al. |
| 8,216,832 B2 | 7/2012 | Battrell et al. |
| 8,231,844 B2 | 7/2012 | Gorfinkel |
| 8,232,091 B2 | 7/2012 | Maltezos et al. |
| 8,232,094 B2 | 7/2012 | Hasson et al. |
| 8,298,763 B2 | 10/2012 | Regan |
| 8,329,453 B2 | 12/2012 | Battrell et al. |
| 8,343,442 B2 | 1/2013 | McBride et al. |
| 8,343,754 B2 | 1/2013 | Wittwer et al. |
| 8,372,340 B2 | 2/2013 | Bird et al. |
| 8,389,960 B2 | 3/2013 | Pieprzyk et al. |
| 8,394,608 B2 | 3/2013 | Ririe et al. |
| 8,426,134 B2 | 4/2013 | Piepenburg et al. |
| 8,475,717 B2 | 7/2013 | Haas et al. |
| 8,492,136 B2 | 7/2013 | Carlisle et al. |
| 8,557,518 B2 | 10/2013 | Jovanovich et al. |
| 8,597,937 B2 | 12/2013 | Ward et al. |
| 8,637,250 B2 | 1/2014 | Jenison |
| 8,722,426 B2 | 5/2014 | Lambotte et al. |
| 8,728,765 B2 | 5/2014 | Ching et al. |
| 8,765,454 B2 | 7/2014 | Zhou et al. |
| 8,772,017 B2 | 7/2014 | Battrell et al. |
| 8,795,592 B2 | 8/2014 | Eiriksson |
| 8,894,946 B2 | 11/2014 | Nielsen et al. |
| 8,895,255 B1 | 11/2014 | Goldberg et al. |
| 8,895,315 B2 | 11/2014 | Batman et al. |
| 8,900,828 B2 | 12/2014 | Smith et al. |
| 8,911,941 B2 | 12/2014 | Michlitsch |
| 8,911,949 B2 | 12/2014 | Bertrand et al. |
| 8,916,375 B2 | 12/2014 | Landers et al. |
| 8,945,843 B2 | 2/2015 | Alvino et al. |
| 8,975,027 B2 | 3/2015 | Gale et al. |
| 8,980,561 B1 | 3/2015 | Cai et al. |
| 9,012,236 B2 | 4/2015 | Jovanovich et al. |
| 9,023,639 B2 | 5/2015 | Kim et al. |
| 9,034,168 B2 | 5/2015 | Khattak et al. |
| 9,044,729 B2 | 6/2015 | Rengifo et al. |
| 9,207,236 B2 | 12/2015 | Cary |
| 9,260,750 B2 | 2/2016 | Hillebrand et al. |
| 9,268,911 B2 | 2/2016 | Sia et al. |
| 9,310,300 B2 | 4/2016 | Alt et al. |
| 9,387,478 B2 | 7/2016 | Bergstedt et al. |
| 9,428,781 B2 | 8/2016 | Cai et al. |
| 9,445,749 B2 | 9/2016 | Erickson et al. |
| 9,469,871 B2 | 10/2016 | Bearinger et al. |
| 9,475,049 B2 | 10/2016 | Siciliano |
| 9,482,635 B2 | 11/2016 | Morales |
| D776,290 S | 1/2017 | Wan et al. |
| 9,623,415 B2 | 4/2017 | Andreyev et al. |
| 9,663,821 B2 | 5/2017 | Unger et al. |
| 9,686,395 B2 | 6/2017 | Erickson et al. |
| 9,702,839 B2 | 7/2017 | Ghaffari et al. |
| 9,718,058 B2 | 8/2017 | Khattak et al. |
| 9,752,182 B2 | 9/2017 | Collier et al. |
| 9,787,815 B2 | 10/2017 | Erickson et al. |
| 9,789,483 B2 | 10/2017 | Khattak et al. |
| 9,807,543 B2 | 10/2017 | Zin et al. |
| 9,810,623 B2 | 11/2017 | Ghaffari et al. |
| 9,841,422 B2 | 12/2017 | Goldberg et al. |
| 9,890,415 B2 | 2/2018 | Stehr et al. |
| 10,040,069 B2 | 8/2018 | Moore et al. |
| 10,052,629 B2 | 8/2018 | Andreyev et al. |
| 10,112,196 B2 | 10/2018 | Andreyev et al. |
| 10,112,197 B2 | 10/2018 | Andreyev et al. |
| 10,124,334 B2 | 11/2018 | Andreyev et al. |
| 10,132,802 B2 | 11/2018 | Ehrenkranz |
| 10,146,909 B2 | 12/2018 | Dimov et al. |
| 10,173,182 B2 | 1/2019 | Tachibana et al. |
| 10,195,610 B2 | 2/2019 | Tang et al. |
| 10,228,377 B2 | 3/2019 | McCarthy et al. |
| 10,267,742 B2 | 4/2019 | Khan |
| 10,603,664 B2 | 3/2020 | Khattak |
| 11,080,848 B2 | 8/2021 | Dimov et al. |
| 11,112,416 B2 | 9/2021 | Pothini et al. |
| 11,162,130 B2 | 11/2021 | Andreyev et al. |
| 11,167,285 B2 | 11/2021 | Andreyev et al. |
| 11,168,354 B2 | 11/2021 | Andreyev et al. |
| 2002/0037520 A1 | 3/2002 | Nikiforov et al. |
| 2003/0027244 A1 | 2/2003 | Colston et al. |
| 2004/0018502 A1 | 1/2004 | Makino et al. |
| 2004/0110141 A1 | 6/2004 | Pusey et al. |
| 2004/0209331 A1 | 10/2004 | Ririe |
| 2004/0224317 A1 | 11/2004 | Kordunsky et al. |
| 2004/0251426 A1 | 12/2004 | Birk et al. |
| 2005/0100946 A1 | 5/2005 | Lipshutz et al. |
| 2005/0194316 A1 | 9/2005 | Pourahmadi et al. |
| 2005/0227275 A1 | 10/2005 | Jung et al. |
| 2006/0160205 A1 | 7/2006 | Blackburn et al. |
| 2006/0177841 A1 | 8/2006 | Wangh et al. |
| 2006/0246493 A1 | 11/2006 | Jensen et al. |

(56) References Cited

U.S. PATENT DOCUMENTS

| | | |
|---|---|---|
| 2007/0026391 A1 | 2/2007 | Stoughton et al. |
| 2007/0036691 A1 | 2/2007 | Lin et al. |
| 2007/0042427 A1 | 2/2007 | Gerdes et al. |
| 2007/0154922 A1 | 7/2007 | Collier et al. |
| 2007/0292941 A1 | 12/2007 | Handique et al. |
| 2008/0038737 A1 | 2/2008 | Smith et al. |
| 2008/0050735 A1 | 2/2008 | Pushnova |
| 2008/0057572 A1 | 3/2008 | Petersen et al. |
| 2008/0113391 A1 | 5/2008 | Gibbons et al. |
| 2008/0153078 A1 | 6/2008 | Braman et al. |
| 2008/0280285 A1 | 11/2008 | Chen et al. |
| 2009/0021728 A1 | 1/2009 | Heinz et al. |
| 2009/0130745 A1 | 5/2009 | Williams et al. |
| 2009/0186344 A1 | 7/2009 | Farinas |
| 2009/0215072 A1 | 8/2009 | McDevitt et al. |
| 2009/0325276 A1 | 12/2009 | Battrell et al. |
| 2010/0003683 A1 | 1/2010 | Sarofim et al. |
| 2010/0035349 A1 | 2/2010 | Bau et al. |
| 2010/0173393 A1 | 7/2010 | Handique et al. |
| 2010/0227386 A1 | 9/2010 | Neuzil et al. |
| 2010/0291588 A1 | 11/2010 | McDevitt et al. |
| 2010/0297640 A1 | 11/2010 | Kumar et al. |
| 2011/0020876 A1 | 1/2011 | Wilding et al. |
| 2011/0039303 A1 | 2/2011 | Janovich et al. |
| 2011/0160090 A1 | 6/2011 | Cary |
| 2011/0203688 A1 | 8/2011 | Reed et al. |
| 2011/0253224 A1 | 10/2011 | Linder et al. |
| 2011/0312074 A1 | 12/2011 | Azimi et al. |
| 2011/0312527 A1 | 12/2011 | Silverbrook et al. |
| 2011/0312666 A1 | 12/2011 | Azimi et al. |
| 2011/0312787 A1 | 12/2011 | Silverbrook et al. |
| 2011/0312841 A1 | 12/2011 | Silverbrook et al. |
| 2012/0021454 A1 | 1/2012 | Bikker et al. |
| 2012/0064534 A1 | 3/2012 | Pipper et al. |
| 2012/0075626 A1 | 3/2012 | Geva et al. |
| 2012/0088294 A1 | 4/2012 | Sun et al. |
| 2012/0135511 A1 | 5/2012 | Battrell et al. |
| 2012/0141337 A1 | 6/2012 | Maltezos et al. |
| 2012/0282681 A1 | 11/2012 | Teixeira et al. |
| 2012/0282684 A1 | 11/2012 | Fritchie et al. |
| 2012/0288897 A1 | 11/2012 | Ching et al. |
| 2013/0040296 A1 | 2/2013 | Tulp et al. |
| 2013/0053255 A1 | 2/2013 | Vangbo et al. |
| 2013/0078736 A1 | 3/2013 | Grover et al. |
| 2013/0115712 A1 | 5/2013 | Yu et al. |
| 2013/0118900 A1 | 5/2013 | Reimitz et al. |
| 2013/0217026 A1 | 8/2013 | Egan et al. |
| 2014/0044609 A1 | 2/2014 | Prusik et al. |
| 2014/0045191 A1 | 2/2014 | DeJohn et al. |
| 2014/0073013 A1 | 3/2014 | Gorman et al. |
| 2014/0087359 A1 | 3/2014 | Njoroge et al. |
| 2014/0098252 A1 | 4/2014 | Chang et al. |
| 2014/0242612 A1 | 8/2014 | Wang et al. |
| 2014/0274770 A1 | 9/2014 | Pack |
| 2014/0329301 A1 | 11/2014 | Handique |
| 2015/0111201 A1 | 4/2015 | Ozcan et al. |
| 2015/0247190 A1 | 9/2015 | Ismagilov et al. |
| 2015/0258273 A1 | 9/2015 | Payne et al. |
| 2015/0346097 A1 | 12/2015 | Battrell et al. |
| 2015/0361419 A1 | 12/2015 | Kim et al. |
| 2016/0008811 A1 | 1/2016 | Laser et al. |
| 2016/0144362 A1 | 5/2016 | Lee et al. |
| 2016/0186240 A1 | 6/2016 | Andreyev et al. |
| 2016/0222442 A1 | 8/2016 | Cary |
| 2016/0256870 A1 | 9/2016 | Ismagilov et al. |
| 2016/0281149 A1 | 9/2016 | Hassibi et al. |
| 2016/0289669 A1 | 10/2016 | Fan et al. |
| 2016/0310948 A1 | 10/2016 | Nowakowski et al. |
| 2017/0021356 A1 | 1/2017 | Dority et al. |
| 2017/0058324 A1 | 3/2017 | Balog et al. |
| 2017/0121756 A1 | 5/2017 | Abate et al. |
| 2017/0173585 A1 | 6/2017 | Mahony et al. |
| 2017/0203297 A1 * | 7/2017 | Andreyev ......... B01L 3/502715 |
| 2017/0247745 A1 | 8/2017 | Schultz et al. |
| 2017/0304829 A1 | 10/2017 | Andreyev et al. |
| 2018/0274031 A1 | 9/2018 | Khatri et al. |
| 2018/0299376 A1 | 10/2018 | Cooper |
| 2018/0304260 A1 | 10/2018 | Thomas et al. |
| 2019/0022643 A1 | 1/2019 | Andreyev et al. |
| 2019/0030532 A1 | 1/2019 | Andreyev et al. |
| 2019/0033223 A1 | 1/2019 | Hand et al. |
| 2019/0040451 A1 | 2/2019 | Mahony et al. |
| 2019/0056341 A1 | 2/2019 | Low et al. |
| 2019/0060895 A1 | 2/2019 | Myers, III et al. |
| 2019/0076841 A1 | 3/2019 | Myers, III et al. |
| 2019/0083975 A1 | 3/2019 | Mitra et al. |
| 2019/0094114 A1 | 3/2019 | Myers et al. |
| 2019/0136226 A1 | 5/2019 | Swenson et al. |
| 2019/0151844 A1 | 5/2019 | Andreyev et al. |
| 2019/0169677 A1 | 6/2019 | Andreyev et al. |
| 2019/0187139 A1 | 6/2019 | Xie et al. |
| 2019/0193077 A1 | 6/2019 | Andreyev et al. |
| 2019/0232283 A1 | 8/2019 | Andreyev et al. |
| 2019/0232293 A1 | 8/2019 | Tang et al. |
| 2019/0262826 A1 | 8/2019 | Rawle |
| 2019/0262827 A1 | 8/2019 | Lalonde et al. |
| 2020/0070157 A1 | 3/2020 | Carrano et al. |
| 2020/0086324 A1 | 3/2020 | Swenson et al. |
| 2020/0346213 A1 | 11/2020 | Andreyev et al. |
| 2020/0408750 A1 | 12/2020 | Khattak |
| 2021/0071236 A1 | 3/2021 | Andreyev et al. |
| 2021/0207194 A1 | 7/2021 | Ciopyk et al. |
| 2021/0292855 A1 | 9/2021 | Rothberg et al. |
| 2021/0293805 A1 | 9/2021 | Rothberg et al. |
| 2021/0295954 A1 | 9/2021 | Rothberg et al. |
| 2021/0299669 A1 | 9/2021 | Swenson et al. |
| 2022/0042076 A1 | 2/2022 | Andreyev et al. |
| 2022/0372557 A1 | 11/2022 | Ciopyk et al. |

FOREIGN PATENT DOCUMENTS

| | | | |
|---|---|---|---|
| WO | WO2001/049416 A1 | 7/2001 | |
| WO | WO2008/082432 | 7/2008 | |
| WO | WO2014/035986 A1 | 3/2014 | |
| WO | WO2014/144548 A2 | 9/2014 | |
| WO | WO2015/143309 A1 | 9/2015 | |
| WO | WO2015/164770 A1 | 10/2015 | |
| WO | WO2016/203019 A1 | 12/2016 | |
| WO | WO2017/025984 A1 | 2/2017 | |
| WO | WO2017/090043 A1 | 6/2017 | |
| WO | WO2017/151195 | 9/2017 | |
| WO | WO2017/160840 A1 | 9/2017 | |
| WO | WO2018/119443 | 6/2018 | |
| WO | WO-2019055135 A1 * | 3/2019 | ............ B01L 3/502 |
| WO | WO2020/180858 | 9/2020 | |
| WO | WO2023/018896 | 2/2023 | |

OTHER PUBLICATIONS

Final Office Action for U.S. Appl. No. 17/017,965, mailed Jul. 19, 2021.

Ahrberg, Christian D. et al. "Polymerase chain reaction in microfluidic devices," © The Royal Society of Chemistry 2016, Lab Chip, 16, pp. 3866-3884, 20 pgs.

Brunklaus, S. et al., Fast nucleic acid amplification for integration in point-of-care applications, Electrophoresis, 2012, vol. 33, pp. 3222-3228.

Choi, Gihoon et al., "A field-deployable mobile molecular diagnostic system for malaria at the point of need," Lab on a Chip, Royal Society of Chemistry, 2016, 16, 4341-4349.

Gehring et al. "A High-Throughput, Precipitating Colorimetric Sandwich ELISA Microarray for Shiga Toxins," J. Toxins, vol. 6, p. 1855-72, Jun. 11, 2014.

Gorgannezhad, Lena et al. "Microfluidic-Based Nucleic Acid Amplification Systems in Microbiology," Micromachines Jun. 19, 2019, 10, 408, www.mdpi.com/journal/micromachines, pp. 1-34.

Harding-Esch et al. "A 30-min nucleic acid amplification point-of-care test for genital *Chlamidya trachomatis* infection in women: a prospective, multi-center study of diagnostic accuracy." EBioMedicine 2018; 28:120-27.

(56) References Cited

OTHER PUBLICATIONS

Huang et al., "Efficient SNP Discovery by Combining Microarray and Lab-on-a-Chip Data for Animal Breeding and Selection," Microarrays, Nov. 16, 2015, vol. 4, No. 4, pp. 570-595, entire document.

Hwang et al., "Black Printed Circuit Board-based Micro-Polymerase Chain Reaction Chip Structure for Fluorescence Detection Test", International Journal of Control and Automation (2015); vol. 8, No. 10: pp. 15-24 (10 pages).

Interbiotech, "Enzymatic substrates for ImmunoAssays," [retreived from the Internet Nov. 18, 2017: <http://www.interchim.fr/ft/B/BA357a.pdf>], 10 pages.

Kim, Yong Tae et al. "Integrated Microdevice of reverse transcription-polymerase chain reaction with colorimetric immunochromatographic detection for rapid gene expression analysis of influenza A H1N1 virus," Biosensors and Bioelectronics, Elsevier Science Ltd UK, Amsterdam, NL V. 33 No. 1, pp. 88-94, Dec. 14, 2011.

Kim, Jungkyu et al. "Automated microfluidic DNA/RNA extraction with both disposable and reusable components," Journal of Micromechanics and Microengineering, Vo. 22, No. 1, Dec. 20, 2011.

Kopp et al., "Chemical Amplification: Continuous-Flow PCR on a Chip", Science (1998); 280 (5366): 1046-1048.

Lee et al. "A polymer lab-on-a-chip for reverse transcription (RT)-PCR based point-of-care clinical diagnostics," The Royal Society of Chemistry, vol. 8, pp. 2121-2127, Oct. 31, 2008.

Lee et al. "Single-channel multiplexing without melting curve analysis in real-time PCR," Scientific Reports, Dec. 11, 2014, vol. 4, Art. No. 7439, pp. 1-6, entire document.

Mohammed et al., Modeling of Serpentine Continuous Flow Polymerase Chain Reaction Microfluidics, IJEST, vol. 4, No. 3, pp. 1183-1189, Mar. 2012.

Petralia, Salvatore et al. "PCR Technologies for Point of Care Testing: Progress and Perspectives," ACS Sensors, 2017, 2 (7), pp. 876-891, Jul. 6, 2017.

Roskos, Kristina et al. "Simple System for Isothermal DNA Amplification Coupled to Lateral Flow Detection," PLoS ONE 8(7): e69355. https://doi.org/10.1371/journal.pone.0069355; Jul. 26, 2013, 11 pages.

Shafagati, et al., The Use of NanoTrap Particles as a Sample Enrichment Method to Enhance the Detection of Rift Valley Fever Virus. PLOS Neglected Tropical Diseases, Jul. 4, 2013; 7(7): e2296.

Tanriverdi et al. A rapid and automated sample-to-result HIV load test for near-patient application. J Infect Dis., 201 Suppl 1:S52-S58, 2010.

Thiha et al. A Colorimetric Enzyme-Linked Immunoabsorbent Assay (ELISA) Detection Platform for a Point-Of-Care Dengue Detection System on a Lab-on-Compact-Disc; Sensors ISSN 1424-8220, May 18, 2015.

Wu, Jinbo et al. "Extraction, amplification and detection of DNA in microfluidic chip-based assays," @Springer-Verlag Wein 2013, pp. 1611-1631.

Zhang, Chunsun et al. "Survey and Summary—Miniaturized PCR chips for nucleic acid amplification and analysis: latest advances and future trends," Nucleic Acids Research, 2007, vol. 35, No. 13, pp. 4223-4237.

Zhang, Chunsun et al. "PCR microfluidic devices for DNA amplification," Biotechnology Advances 24, (2006) pp. 243-284.

Office Action for Chinese Application No. 202080031980.5, mailed Nov. 23, 2022.

Extended Search Report for European Application No. 20798444.4, dated Jan. 3, 2023.

Du, Wenbin et al. "SlipChip," NIH-PA Author Manuscript, NIH Public Access, Author Manuscript, published in final edited form as Lap Chip, PMC, Aug. 21, 2009, 14 pgs.

Medical Design Briefs "Sense Accelerates Instrument-Free Molecular Diagnostic Test for Covid-19," Found online Mar. 28, 2024 at medicaldesignbriefs.com, Retrieved from <https://www.medicaldesignbriefs.com/component/content/article/36631-sense-accelerates-instrument-free-molecular-diagnostic-test-for-covid-19> Reference dated Apr. 7, 2020 (1 page).

RAJENDRAN Vinoth Kumar et al. "Smartphone detection of antibiotic resistance using convective PCR and a lateral flow assay", Sensors and Actuators B: Chemical, Elsevier vol. 298, Jul. 23, 2019 (10 pgs.).

Benett, William et al. "Handheld advanced nucleic acid analyzer," Event: Environmental and Industrial Sensing, Boston, MA, Proceedings of SPIE, vol. 4200 (2000), pp. 55-63.

Hassibi et al. "An array-based melt curve analysis method for the identification and classification of closely related pathogen strains." Biology Methods and Protocols 2018; pp. 1-12.

Primiceri, Elisabetta et al. "Key Enabling Technologies for Point-of-Care Diagnostics," MDPI, Sensors 18, 3607; doi:10.3390/s18113607, www.mdpi.com/journal/sensors, 2018, pp. 1-34.

Richards, James et al. "Miniaturized detection system for handheld PCR assays," Event: Environmental and Industrial Sensing, Boston, MA, Proceedings of SPIE, vol. 4200 (2000), pp. 64-73.

Tsaloglou, Maria-Nefeli et al. "Handheld isothermal amplification and electrochemical detection of DNA in resource-limited settings," Analytical Biochemistry 543, 2018, pp. 116-121.

Ullerich, Lars et al. "Ultra-fast PCR technologies for point-of-care testing," De Gruyter, J. Lab Med 2017; 41(5), pp. 239-244.

Yotoriyama, T. et al. "Miniaturized PCR Device for Rapid Detection of Infectious Agents," 14th International Conference on Miniaturized Systems for Chemistry and Life Sciences, Oct. 3-17, 2010, pp. 142-144.

\* cited by examiner

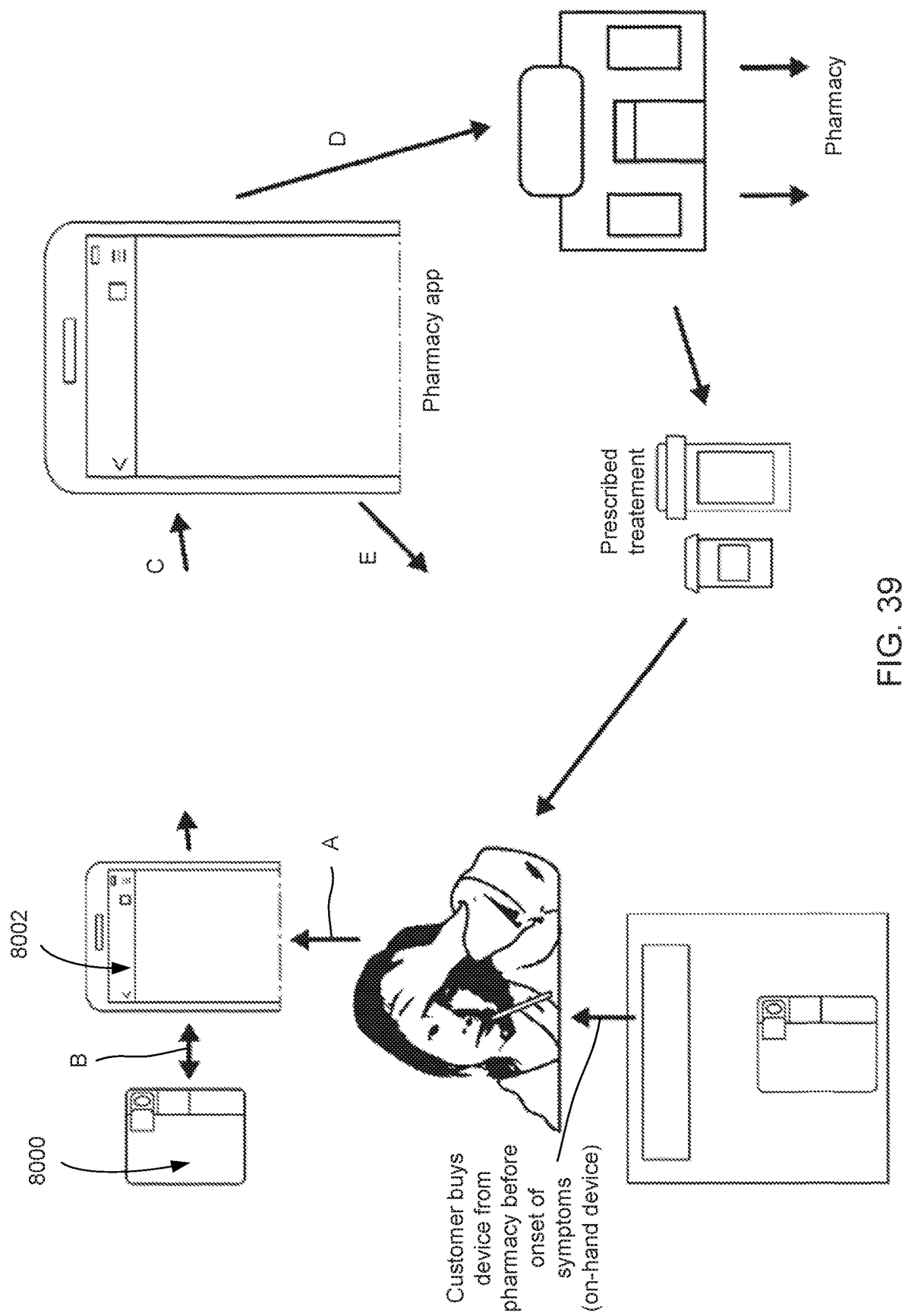

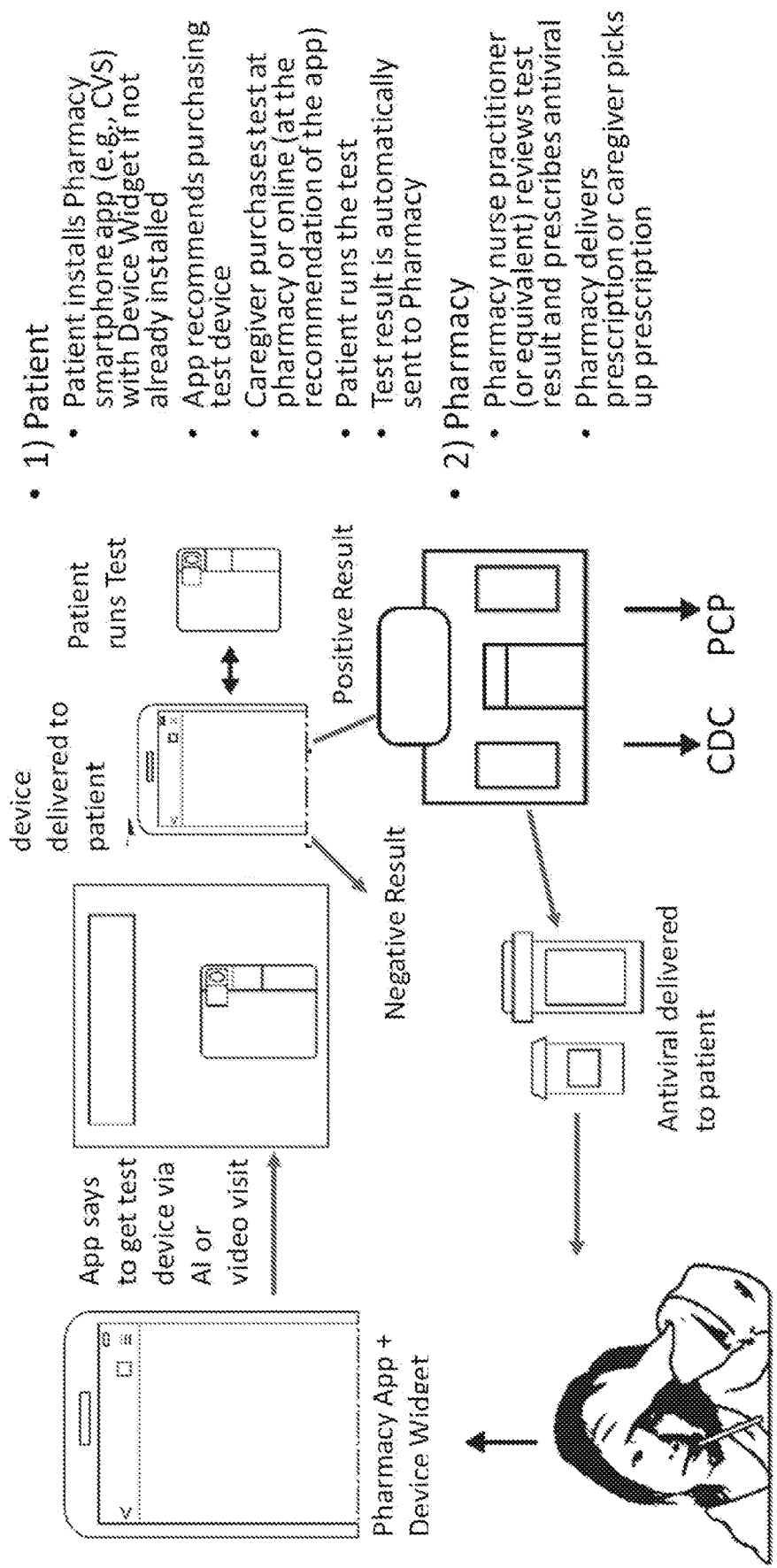

MOLECULAR DIAGNOSTIC DEVICES WITH DIGITAL DETECTION CAPABILITY AND WIRELESS CONNECTIVITY

CROSS-REFERENCE TO RELATED APPLICATIONS

This application is a U.S. national stage filing under 35 U.S.C. § 371 of International Application No. PCT/US2020/030307, entitled "Molecular Diagnostic Devices with Digital Detection Capability and Wireless Connectivity," filed Apr. 28, 2020, which claims benefit of priority to U.S. Provisional Application Ser. Nos. 62/839,724, entitled "Molecular Diagnostic Devices with Digital Detection Capability and Wireless Connectivity," filed Apr. 28, 2019, and 62/957,068, entitled "Devices and Methods for Antibiotic Susceptibility Testing," filed Jan. 3, 2020, each of which is incorporated herein by reference in its entirety.

BACKGROUND

The embodiments described herein relate to devices and methods for molecular diagnostic testing. More particularly, the embodiments described herein relate to disposable, self-contained devices and methods for molecular diagnostic testing that include digital detection capabilities and wireless connectivity, which can enable an operable connection to electronic health records and/or other databases designed to improve healthcare outcomes.

There are over one billion infections in the U.S. each year, many of which are treated incorrectly due to inaccurate or delayed diagnostic results. Many known point of care (POC) tests have poor sensitivity (30-70%), while the more highly sensitive tests, such as those involving the specific detection of nucleic acids or molecular testing associated with a pathogenic target, are only available in laboratories. Thus, molecular diagnostics testing is often practiced in centralized laboratories. Known devices and methods for conducting laboratory-based molecular diagnostics testing, however, require trained personnel, regulated infrastructure, and expensive, high throughput instrumentation. Known high throughput laboratory equipment generally processes many (96 to 384 and more) samples at a time, therefore central lab testing is often done in batches. Known methods for processing test samples typically include processing all samples collected during a time period (e.g., a day) in one large run, resulting in a turn-around time of many hours to days after the sample is collected. Moreover, such known instrumentation and methods are designed to perform certain operations under the guidance of a skilled technician who adds reagents, oversees processing, and moves sample from step to step. Thus, although known laboratory tests and methods are very accurate, they often take considerable time, and are very expensive.

Although recent advances in technology have enabled the development of "lab on a chip" devices, such devices are often not optimized for point-of-care testing or in-home use. For example, some known devices and methods require an expensive or complicated instrument to interface with the test cartridge, thus increasing the likelihood of misuse. Additionally, many known "lab on a chip" devices amplify a very small volume of sample (e.g., less than one microliter), and are therefore not suited for analyzing for multiple different indications (e.g., a 3-plex or 4-plex test). Moreover, devices that produce such small sample volumes often include optical detection using photocells, charge coupled devices (CCD cameras) or the like, because the sample volumes are too small to produce an output that can be read by the naked eye or less sophisticated (and costly) detectors.

Although some known laboratory-based molecular diagnostics test methods and equipment offer flexibility (e.g., the ability to test for multiple different indications), such methods and equipment are not easily adaptable for point of care ("POC") use or in-home use by an untrained user. Specifically, such known devices and methods are complicated to use and include expensive and sophisticated components. Thus, the use of such known laboratory-based methods and devices in a decentralized setting (e.g., POC or in-home use) would likely result in an increase in misuse, leading to inaccurate results or safety concerns. For example, many known laboratory-based systems include sophisticated optics and laser light sources, which can present a safety hazard to an untrained user. Some known systems can also require the user to handle or be exposed to reagents, which can be a safety risk for an untrained user. In addition to being unsuitable for decentralized use, these known systems are also not suitable for long-term storage and shipping. Long-term storage can be desirable, for example to allow for stockpiling of assays for military applications, as a part of the CDC strategic national stockpile program, or other emergency preparedness initiatives.

In addition to these and other difficulties associated with successfully performing molecular diagnostic tests in a decentralized setting, current POC or in-home tests are also difficult to interpret. For example, some known molecular diagnostic tests rely on the user to visually inspect a detection window or strip to determine whether a color change occurred thereby indicating a positive result. Other known tests and methods rely on the user to compare two different portions (e.g., strips) to make a determination regarding whether the test is positive or negative. Although in some instances such known methods can produce acceptable results, in instances when the device does not behave as intended, the results can be mis-interpreted. For example, if a sample has a low load of the target pathogen, the visual readout (e.g., color change) may not be as distinct as indicated on the instructions for use, thereby causing incorrect interpretations. As another example, if certain portions of the sample "bleed" into the background, the visual readout may not be well defined.

Known POC or in-home tests also provide little or no guidance regarding follow-up care and the results provided are not monitored (e.g., for tracking or follow-up purposes). By their very nature, such known tests and methods are conducted in a decentralized location by untrained users. Therefore, follow-up care is often only received if the user proactively contacts a healthcare provider. Moreover, known tests lack connectivity to centralized databases that are used to track the spread of disease.

Thus, a need exists for improved devices and methods for molecular diagnostic testing. In particular, a need exists for improved devices and methods that include digital detection capabilities and wireless connectivity, which can enable an operable connection to electronic health records and/or other databases designed to improve healthcare outcomes.

SUMMARY

Molecular diagnostic test devices having digital detection capabilities and wireless connectivity are described herein. In some embodiments, a stand-alone molecular diagnostic test device includes a detection circuit that includes a light emitting device and a light receiving device (e.g., a photodiode) that are arranged to produce an electronic signal associated with a colorimetric output produced by the stand-alone molecular diagnostic test.

In some embodiments, a molecular diagnostic test device includes a housing, a detection module within the housing, a reagent within the housing, and an electronic system within the housing. The housing defines an input opening through which a biological sample can be conveyed. The detection module defines a detection volume into which the biological sample can be conveyed. The reagent is formulated to facilitate production of an assay signal indicating the presence of a target polynucleotide sequence within the biological sample. The electronic system includes a photodetector assembly, a memory, a processing device and a digital read module implemented in at least one of the memory or the processing device. The digital read module is configured to receive, from the photodetector assembly, a first light signal for a first time period before the biological sample and a reagent are reacted within the detection volume. The digital read module is configured to determine a first magnitude associated with the first light signal during the first time period. The digital read module is configured to receive, from the photodetector assembly, a second light signal for a second time period after the biological sample and the reagent are reacted within the detection volume of the detection module. The second light signal is associated with the assay signal. The digital read module is configured to determine a second magnitude associated with the second light signal during the second time period. The digital read module is configured to determine, based on a comparison of the first magnitude and the second magnitude, whether the target polynucleotide sequence is present in the biological sample. The electronic system is configured to produce an electronic output when the target polynucleotide sequence is determined to be present in the biological sample.

In some embodiments, the target polynucleotide sequence is associated with target organism, include one or more bacteria, fungi, viruses, parasites, or protozoa. In some embodiments, the target polynucleotide sequence can be a portion of a genome used to identify an organism within the biological sample, such as a bacteria (e.g., *Chlamydia trachomatis, Neisseria gonorrhea* and *Trichomonas vaginalis*) or a virus (e.g., Influenza (Flu A, Flu B), Respiratory Syncytial Virus, SARS-CoV-2). In some embodiments, the target polynucleotide sequence can be a portion of a genome that confers a phenotype (e.g., resistance or susceptibility to a course of treatment, such as antibiotics) on the organism. In some embodiments, the target polynucleotide sequence can be a single nucleotide polymorphism (SNP) in an organism.

In some embodiments, the electronic output is a light output, an audible output, a wireless signal, a haptic output, or any combination of these. In some embodiments, the electronic system includes a radio configured to electronically communicate with a computing device via a short-range wireless communication protocol and the electronic output includes a wireless signal indicating the presence of the target polynucleotide sequence.

In some embodiments, the reagent is a solid reagent that is present in the detection module. In other embodiments, the reagent is a liquid reagent that is stored within the molecular diagnostic test device. Specifically, in some embodiments, the molecular diagnostic test device further includes a reagent module and a valve. The reagent module contains the reagent separate from the detection module during the first time period. The electronic system includes a flow control module implemented in at least one of the memory or the processing device. The flow control module is configured to produce a reagent signal to actuate the valve causing the reagent to flow from the reagent module into the detection module.

In some embodiments, the molecular diagnostic test device further includes an amplification module and a pump. The amplification module includes a reaction volume and a heater. The reaction volume is configured to receive the biological sample and the heater conveys thermal energy into the reaction volume to amplify the target polynucleotide sequence. The pump is configured to produce a flow of the biological sample from the amplification module to the detection module.

In some embodiments, a molecular diagnostic test device includes a housing, a detection module within the housing, a reagent within the housing, and an electronic system within the housing. The housing defines an input opening through which a biological sample can be conveyed. The detection module defines a detection volume into which the biological sample can be conveyed. The reagent is formulated to facilitate production of a colorimetric signal within the detection module after the biological sample and the reagent are reacted within the detection volume. The colorimetric signal indicates the presence of a target polynucleotide sequence within the biological sample. The electronic system includes a photodetector assembly, a memory, a processing device and a digital read module implemented in at least one of the memory or the processing device. The light assembly is positioned on a first side of the detection module and is configured to produce a light beam that passes through detection volume of the detection module. The photodetector assembly is positioned on the first side of the detection module and receives a light signal that is associated with any of a reflection or an attenuation of the light beam. The digital read module is configured to determine a magnitude of the light signal and produce, based on the magnitude, an indication whether the colorimetric signal is present in the detection volume.

In some embodiments, the detection module includes a detection flow cell and a heater. The detection flow cell defines the detection volume within which at least one of the biological sample or the reagent can be conveyed. The heater is coupled to a surface of the detection flow cell on a second side of the detection module. The second side is opposite the first side (i.e., the heater is on the opposite side of the detection module from both the light assembly and the photodetector assembly). In some embodiments, the detection flow cell includes a reflective portion on the second side of the detection module. The reflective portion reflects the light beam produced by the light assembly positioned on the first side of the detection module back towards the photodetector assembly. In some embodiments, the detection flow cell includes a light-blocking portion on a third side of the detection module. The third side is nonparallel to the first side and the second side (e.g., the third side can be a side edge of the detection module).

In some embodiments, the detection module includes a detection surface and the colorimetric signal is produced at the detection surface. The light assembly is configured to produce the light beam incident upon the detection surface and the photodetector assembly receives the light signal. The light signal is associated with any of the reflection or the attenuation of the first light beam. A detection envelope is defined about the detection surface, with the light beam and the light signal each being within the detection envelope. The molecular diagnostic test device further includes a light shield surrounding the detection envelope.

In some embodiments, a non-transitory processor-readable medium includes code to cause a processor of a molecular diagnostic test device to receive a signal associated within an amount of light. The code (executed on a processor) can determine a test result based on a change in the signal over a time period. The code (executed on a processor) can cause the device to produce a signal (e.g., a light signal, a wireless signal or the like) associated with the test result.

In some embodiments, a computer-implemented method of detecting the presence of a target polynucleotide sequence within a biological sample can be performed using a molecular diagnostic test device. The method includes receiving, at a photodetector assembly of an electronic system, a first light signal for a first time period after the biological sample and a reagent are reacted within a detection volume of a detection module of the molecular diagnostic test device. The reagent is formulated to facilitate production of a first assay signal and a second assay signal. The first assay signal indicates the presence of the target polynucleotide sequence and the second assay signal indicates the presence of a reference polynucleotide sequence. The first light signal is associated with the first assay signal. A second light signal is received for a second time period after the biological sample and the reagent are reacted within the detection volume of the detection module. The second light signal is associated with the second assay signal. The method includes determining a first magnitude associated with the first light signal during the first time period and determining a second magnitude associated with the second light signal during the second time period. An electronic output is produced when a comparison of the first magnitude and the second magnitude indicates that the target polynucleotide sequence is present.

In some embodiments, the first magnitude and/or the second magnitude can include an average intensity of the light signal over the time period, a rate of change (i.e., slope) of the light signal over the time period, a variability of the light signal over the time period, or any combination of the average intensity, slope, and variability. In some embodiments, the electronic output is produced when a difference between the first magnitude and the second magnitude is within a predetermined magnitude range or a ratio between the first magnitude and the second magnitude is within a predetermined ratio range.

In some embodiments, the determining the first magnitude, the determining the second magnitude, and the comparing of the first magnitude and the second magnitude are performed in a digital read module implemented in at least one of a memory or a processing device of the electronic system.

In some embodiments, either (or both) of the first assay signal or the second assay signal are a colorimetric signal, a chemiluminescence signal, or a fluorescence signal.

In some embodiments, the reference polynucleotide sequence can be an internal control polynucleotide sequence (i.e., a sequence associated with the organism). In some embodiments, the reference polynucleotide sequence can be an external control polynucleotide sequence (i.e., a sequence that is added to the biological solution). For example, in some embodiments, an external control polynucleotide sequence can be a positive control that is added before during or after the biological sample is placed within the molecular diagnostic test device. In some embodiments, the reference polynucleotide sequence can be an invariant polynucleotide sequence associated with the target polynucleotide sequence, such as a polynucleotide sequence associated with a particular polymorphism (e.g., a nucleotide at a SNP).

In some embodiments, a computer-implemented method of detecting the presence of a target polynucleotide sequence within a biological sample can be performed using a molecular diagnostic test device. The method includes receiving, at a photodetector assembly of an electronic system, a first light signal for a first time period before the biological sample and a reagent are reacted within a detection volume of a detection module. The reagent is formulated to facilitate production of a colorimetric signal within the detection volume. The colorimetric signal indicates the presence of the target polynucleotide sequence. The first light signal is associated with a light beam conveyed through the detection module and into the detection volume. A second light signal is received for a second time period after the biological sample and the reagent are reacted within the detection volume of the detection module. The second light signal is associated with the light beam conveyed through the detection module and into the detection volume. The method includes determining a first slope of the first light signal during the first time period and a second slope of the second light signal during the second time period. An electronic output is produced when a comparison of the first slope and the second slope indicates that the colorimetric signal (and thus, the presence of the target polynucleotide sequence) is present.

In some embodiments, the first light signal and the second light signal are each associated with an attenuation of the light beam through the detection volume of the detection module.

In some embodiments, the molecular diagnostic test device is a stand-alone molecular diagnostic test device and the methods of detecting described herein are performed without any external instrument.

In some embodiments, a stand-alone molecular diagnostic test device includes a detection module and an electronic control module (also referred to as an electronic circuit system). The electronic circuit system includes a radio such that the apparatus can be electronically linked to a computing device using a wireless protocol. The stand-alone molecular diagnostic test device (including the electronic control module) can be a single-use, disposable device.

In some embodiments, a molecular diagnostic test device includes a radio, a memory and a communication module. The radio is configured to electronically communicate with a computing device via a wireless protocol (e.g., Bluetooth®). The radio is configured to send a wireless signal associated with a test result. The memory is configured to store information associated with a result (e.g., positive or negative for a given indication) of the test. The communication module, which is implemented in at least one of the memory or a processing device, is configured to control the transmission of the wireless signal.

In some embodiments, a molecular diagnostic test device includes a housing, a detection module within the housing, a reagent within the housing, and an electronic system within the housing. The housing defines an input opening through which a biological sample can be conveyed. The detection module defines a detection volume into which the biological sample can be conveyed. The reagent is formulated to facilitate production of an assay signal within the detection module after the biological sample and the reagent are reacted within the detection volume. The assay signal indicates the presence of a target polynucleotide sequence within the biological sample. The electronic system includes a sensor, a digital read module, and a radio. The sensor (e.g., a photodetector, a chemical detector, or the like) produces a sensor signal associated with the assay signal. The digital read module is implemented in at least one of a memory or a processing device and determines, based on at least one of an intensity of the sensor signal, a slope of the sensor signal, or a variability of the sensor signal, whether the assay signal is present in the detection volume. The radio electronically communicates with a computing device via a short-range wireless communication protocol. The radio sends a first wireless signal to establish a communications link between the computing device and the molecular diagnostic test device. The radio sends a second wireless signal indicating whether the assay signal is present.

In some embodiments, a computer-implemented method of detecting the presence of a target polynucleotide sequence within a biological sample can be performed using a molecular diagnostic test device that includes a housing, a detection module, a reagent, and an electronic system. The detection module defines a detection volume into which the biological sample can be conveyed. The reagent is formulated to facilitate production of an assay signal within the detection module after the biological sample and the reagent are reacted within the detection volume. The assay signal indicates the presence of the target polynucleotide sequence. The electronic system includes a sensor configured to produce a sensor signal associated with the assay signal. The method includes establishing a communications link, via a short-range wireless protocol, between a mobile computing device and the molecular diagnostic test device. A first wireless signal associated with the target polynucleotide sequence is received from the electronic system of the molecular diagnostic test device. A second wireless signal associated with the sensor signal is received from the electronic system of the molecular diagnostic test device. The method further includes producing a test result notification based on the first wireless signal and the second wireless signal.

In some embodiments, the method further includes transmitting a third wireless signal associated with the test result notification. The third wireless signal indicates a location of the molecular diagnostic test device. The location can be based on a location information produced by the mobile computing device. In some embodiments, the third wireless signal is devoid of information associated with a patient identity and includes information associated with at least one patient characteristic (e.g., demographic information, general health information).

BRIEF DESCRIPTION OF THE DRAWINGS

FIG. 39 is a schematic illustration showing a connected health workflow, according to an embodiment.

FIG. 40 is a schematic illustration showing a connected health workflow, according to an embodiment.

DETAILED DESCRIPTION

Figure 1:
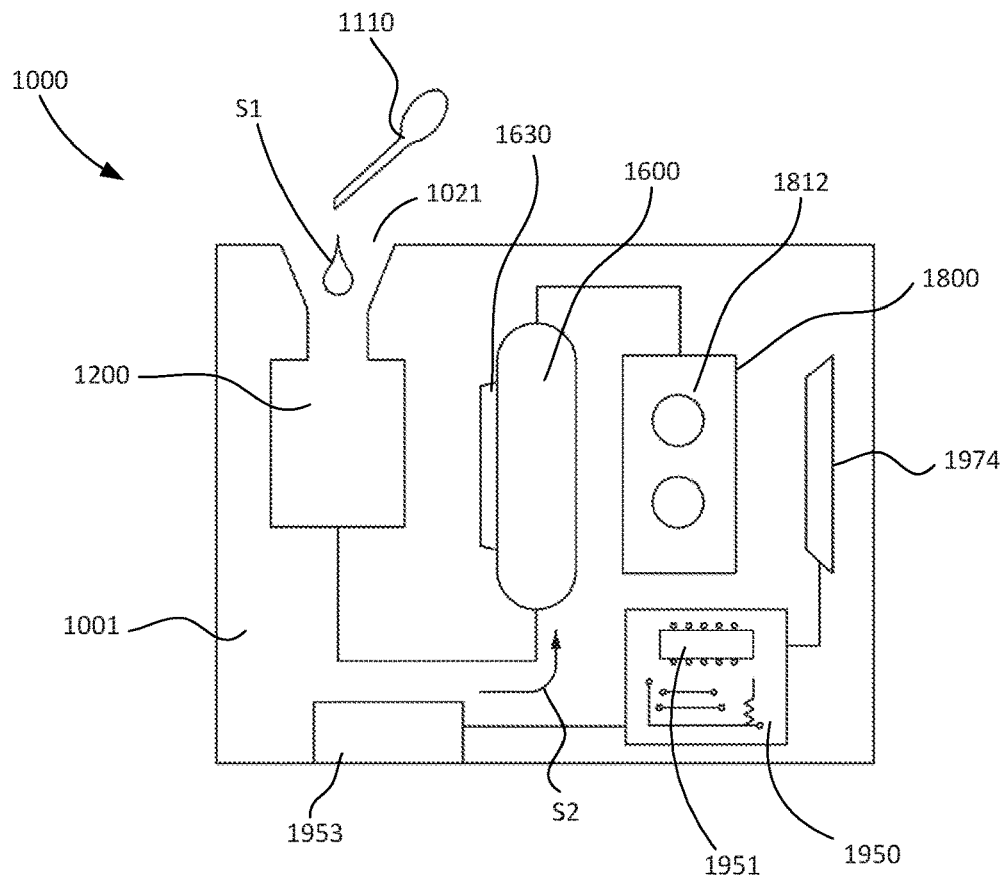
FIGS. 1-4 are schematic illustrations of a molecular diagnostic test device configured to detect the presence of a target polynucleotide sequence within a biological sample, according to an embodiment, in a first configuration (FIG. 1), a second configuration (FIG. 2), a third configuration (FIG. 3), and an optional fourth configuration (FIG. 4).

In some embodiments, an apparatus is configured for a disposable, portable, single-use, inexpensive, molecular diagnostic approach. The apparatus can include one or more modules configured to perform high quality molecular diagnostic tests, including, but not limited to, sample preparation, nucleic acid amplification (e.g., via polymerase chain reaction, isothermal amplification, or the like), and detection. In some embodiments, sample preparation can be performed by isolating the pathogen/entity and removing unwanted amplification (e.g., PCR) inhibitors. The target entity can be subsequently lysed to release target nucleic acid for amplification. A target nucleic acid (e.g., target polynucleotide sequence) in the target entity can be amplified with a polymerase undergoing temperature cycling or via an isothermal incubation to yield a greater number of copies of the target nucleic acid sequence for detection.

In some embodiments, the devices described herein are stand-alone devices that include all necessary substances, mechanisms, and subassemblies to perform any of the molecular diagnostic tests described herein. Such stand-alone devices do not require any external instrument to manipulate the biological samples, and, in some embodiments, only require connection to a power source (e.g., a connection to an A/C power source, coupling to a battery, or the like) to complete the methods described herein. For example, the device described herein do not require any external instrument to heat the sample, agitate or mix the sample, to pump (or move) fluids within a flow member, or the like. Rather, the embodiments described herein are fully-contained and upon add a biological sample and being coupled to a power source, the device can be actuated to perform the molecular diagnostic tests described herein. In some embodiments, the methods and devices are configured such that the device is a CLIA-waived device and/or can operate in accordance with methods that are CLIA waived. In some embodiments, the methods and devices are suitable for use within a point-of-care setting (e.g., doctor's office, pharmacy or the like). In some embodiments, the methods and devices are suitable for use as an over-the-counter (OTC) diagnostic solution. Similarly stated, in some embodiments, the methods and devices are suitable for use by an untrained user (i.e., a lay user), can be supplied without a prescription, and can be performed independent of a health care facility (e.g., at the user's home).

Unless indicated otherwise, the terms apparatus, diagnostic apparatus, diagnostic system, diagnostic test, diagnostic test system, test unit, and variants thereof, can be interchangeably used.

In some embodiments, methods and devices of the present disclosure are utilized to detect the presence of infections with microorganisms within a biological sample. As described herein, detection can include reacting a reagent and a biological sample (including a processed portion of the biological sample that has been amplified) within a detection module to produce one or more assay signals associated with the presence of a polynucleotide sequence. The reacting can be performed by combining (e.g., mixing) the reagent and the biological sample within the detection module, by introducing each of the reagent and the biological sample into the detection module (either at the same time or in a sequential manner), by conveying the biological sample into the detection module, within which the reagent has been stored for use, or any other suitable method for producing the desired reaction. A light signal can be received by a photodetector assembly to electronically detect the presence of the assay signal.

Terms and symbols of nucleic acid chemistry, biochemistry, genetics, and molecular biology used herein follow those of standard treatises and texts in the field, e.g., Kornberg and Baker, *DNA Replication*, Second Edition (W. H. Freeman, New York, 1992); Lehninger, Biochemistry, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

The term "organism" may refer to a microorganism, such as one or more bacteria, fungi, protozoa, viruses. In some embodiments, the organism is multicellular (e.g., a worm or other parasite). The organism may be pathogenic. Illustrative organisms include *Bacillus, Bartonella, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio,* and *Yersinia.*

As used herein, a "biological sample" refers to any tissue or fluid obtained from an organism (e.g. a subject, e.g. a human or animal subject) that contains a polynucleotide (e.g., DNA or RNA) that can be amplified and/or detected by the devices described herein. In some embodiments, any of the devices and methods described herein can be conducted on a variety of different types of samples. Such sample types can include, for example, vaginal swab, penile meatal swab sample, a buccal swab, stool, sputum, nasal wash, nasal aspirate, throat swab, bronchial lavage, blood, blood cells (e.g. white blood cells), fine needle biopsy samples, peritoneal fluid, visceral fluid, pleural fluid, a urine sample, rectal swab sample and/or pharyngeal swab sample, or cells therefrom. Other biological samples useful in the present invention include tumor samples (e.g. biopsies) and blood samples. The term "biological sample" also refers to a portion of the tissue or fluid obtained that has been processed (e.g., that has been filtered, lysed, prepared, amplified or reacted) in connection with the diagnostic methods described herein. Thus, a biological sample can refer to a raw sample (e.g. a raw blood sample) obtained from a patient, as well as a portion of the raw sample that has been "prepared" for use, reacted, or amplified in any of the devices or methods described herein.

The term "nucleic acid molecule," "nucleic acid," or "polynucleotide" may be used interchangeably herein, and may refer to deoxyribonucleic acid (DNA) or ribonucleic acid (RNA), including known analogs or a combination thereof unless otherwise indicated. Nucleic acid molecules to be profiled herein can be obtained from any source of nucleic acid. The nucleic acid molecule can be single-stranded or double-stranded. In some cases, the nucleic acid molecules are DNA. The DNA can be mitochondrial DNA, complementary DNA (cDNA), or genomic DNA. In some cases, the nucleic acid molecules are genomic DNA (gDNA). The DNA can be plasmid DNA, cosmid DNA, bacterial artificial chromosome (BAC), or yeast artificial chromosome (YAC). The DNA can be derived from one or more chromosomes. For example, if the DNA is from a human, the DNA can be derived from one or more of chromosomes 1, 2, 3, 4, 5, 6, 7, 8, 9, 10, 11, 12, 13, 14, 15, 16, 17, 18, 19, 20, 21, 22, X, or Y. In some cases, the nucleic acid molecules include, but are not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. The non-coding RNA, or ncRNA can include snoRNAs, microRNAs, siRNAs, piRNAs and long nc RNAs. Bacterial resistance may be conferred by plasmids or phage and in such cases the polynucleotide may be the plasmid or the phage genome. In some embodiments, "a polynucleotide associated with a target organism" refers to two or more polynucleotides. For example, detection of a locus on a first polynucleotide (e.g., the genomic DNA of the organism) is used to detect presence of the organism while resistance or susceptibility to a drug is determined by detection of the plasmid or phage associated with the target organism. The source of nucleic acid for use in the devices, methods, and compositions described herein can be a biological sample comprising the nucleic acid.

Target nucleic acid sequences or target polynucleotides (or polynucleotide sequences) include genomic nucleic acids of a particular organism. Such target nucleic acid sequences may be single stranded or double stranded and may include a sense strand and/or an antisense strand. Such target nucleic acid sequences may be a deoxyribonucleic acid ("DNA") or a ribonucleic acid ("RNA").

Polymorphisms, in general, refer to changes of a nucleotide at a single base-pair location on a nucleic acid. A polymorphism means a substitution, inversion, insertion, or deletion of one or more nucleotides at a genetic locus, or a translocation of DNA from one genetic locus to another genetic locus. A "single nucleotide polymorphism" or "SNP" as used herein refers to a substitution of one nucleotide in the polynucleotide sequence of a genome of an organism with respect to a reference sequence (e.g. the wild-type sequence of the organism, or any alternative sequence variant present in a population of organisms of the same species). For example, a SNP in an organism is a nucleotide position that differs between representatives of that species; a SNP in a human population is a nucleotide position that differs between representatives between individuals; and a SNP in the context of cancer is a nucleotide position that differs between the genome of the subject and the genome of tumor cells within the subject. The term "polymorphic locus" refers to a locus comprising a polymorphism (e.g. a SNP) and sufficient flanking polynucleotide sequences to permit detection by a probe.

An "allele" refers to a particular polymorphism (e.g., a nucleotide at the SNP) whose detection is desired. When the SNP is in a coding sequence, the allele may encode a change in the protein encoded by the polynucleotide (or "target region"). An "antiallele" refers to nucleotide present at the same position (i.e. the SNP locus) in the reference sequence. In the case of drug-resistance detection, the drug-resistance allele is the nucleotide whose presence in the polynucleotide confers a phenotype (e.g., resistance or susceptibility) on the organism. The antiallele refers to an allele that confers the opposite phenotype on the organism. Conversely, in the detection of drug sensitivity, the "allele" is the nucleotide at the SNP locus that covers sensitivity to the drug; the "antiallele" is the nucleotide at the SNP locus of the reference sequence, the same organism having resistance to the drug. When more than two alternative nucleotides are observed at the same position in a sequence (the SNP locus), the "allele" is the nucleotide to be detected, and the two or three alternative nucleotides are "antialleles."

Such SNPs can occur in organisms with highly variable genomes, such as pathogens in general. One of skill will readily understand and identify pathogens in general and those characterized with highly variable genomes. Such pathogens include such as viruses, organism, parasites and fungi. The devices and methods described herein are not limited to any particular SNP, as the devices and methods described herein are intended to determine the presence of a various SNPs. SNP can readily be identified in literature in various organisms.

In some embodiments, the target nucleic acid or polynucleotide sequences may be amplified using methods known to those of skill in the art. Such methods include using a polymerase, primers and nucleotides. "Amplifying" includes the production of copies of a nucleic acid molecule via repeated rounds of primed enzymatic synthesis.

Amplification methods may comprise contacting a nucleic acid with one or more primers that specifically hybridize to the nucleic acid under conditions that facilitate hybridization and chain extension. Exemplary methods for amplifying nucleic acids include the polymerase chain reaction (PCR) (see, e.g., Mullis et al. (1986) Cold Spring Harb. Symp. Quant. Biol. 51 Pt 1:263 and Cleary et al. (2004) Nature Methods 1:241; and U.S. Pat. Nos. 4,683,195 and 4,683,202), anchor PCR, RACE PCR, ligation chain reaction (LCR) (see, e.g., Landegran et al. (1988) Science 241:1077-1080; and Nakazawa et al. (1994) Proc. Natl. Acad. Sci. U.S.A. 91:360-364), self-sustained sequence replication (Guatelli et al. (1990) Proc. Natl. Acad. Sci. U.S.A. 87:1874), transcriptional amplification system (Kwoh et al. (1989) Proc. Natl. Acad. Sci. U.S.A. 86:1173), Q-Beta Replicase (Lizardi et al. (1988) BioTechnology 6:1197), recursive PCR (Jaffe et al. (2000) J. Biol. Chem. 275:2619; and Williams et al. (2002) J. Biol. Chem. 277:7790), the amplification methods described in U.S. Pat. Nos. 6,391, 544, 6,365,375, 6,294,323, 6,261,797, 6,124,090 and 5,612, 199, or any other nucleic acid amplification method using techniques well known to those of skill in the art. In some embodiments, the methods disclosed herein utilize linear amplification. In some embodiments, the methods disclosed herein utilize PCR amplification.

"Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 72-78° C.

The term "PCR" encompasses derivative forms of the reaction, including but not limited to, reverse transcription (RT)-PCR, nested PCR, quantitative PCR, multiplexed PCR, and the like. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. e.g., "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) Anal. Biochem., 273:221-228. Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., Biotechniques, 26:112-126 (1999); Becker-Andre et al., Nucleic Acids Research, 17:9437-9447 (1989); Zimmerman et al., Biotechniques, 21:268-279 (1996); Diviacco et al., Gene, 122:3013-3020 (1992); Becker-Andre et al., Nucleic Acids Research, 17:9437-9446 (1989); and the like.

In some embodiments, a detection module includes one or more probes designed to bind to an amplicon associated with the target polynucleotide sequence. The term "probe" as used herein refers to an unlabeled oligonucleotide used to capture a target amplicon. Generally the probe is covalently conjugated to a surface of the detection module, although non-covalent conjugated methods may also be employed. An illustrative, non-limiting means for conjugating a probe to a substrate is a amide coupled. In some embodiments, the surface of the detection module comprises an amorphous polymer (e.g., a cyclic olefin copolymer (COC)). Surface modification of a COC substrate surface can be achieved by oxygen plasma treatment, such as described in Hwang et al. Surface and Coatings Technology 202:3669-74 (2008); Gubala et al. Colloids and Surfaces B: Biointerfaces 81:544-48 (2010); or Carvalho et al. ACS Applied Materials and Interfaces 9:16644-50 (2017). Following activation of the substrate (e.g. a COC substrate) to yield an amine-reactive substrate (e.g. carboxylated COC), amino-modified oligonucleotides can be coupled to the surface by various attachment chemistries including but not limited to acrylic phosphoramidite (Acrydite™), adenylation, azide (NHS ester), I-Linker™ (to aldehyde or ketone-modified substrates), or amino modifiers. A primary amino group can be used to attach the oligonucleotide probes to the surface. Amino modifiers can be positioned at the 5'-end with either a standard (C6) or longer (C12) spacer arm. Amino modifications can also be positioned at the 3'-end. Internal amino modifications can be introduced using an amino-dT base. Illustrative amino modifiers include a 3' amino modifier C6, 3' amino modifier C12, 5' amino modifier C6, and a 5' amino modifier C12. A "resistance probe" is a probe that binds preferentially to an allele associated with resistance to treatment (e.g. drug treatment). A "susceptibility probe" or "sensitivity probe" is a probe that binds preferentially to an allele associated with susceptible to treatment (e.g. drug treatment).

A probe according to the present disclosure may be referred to as a hybridization probe which is a fragment of DNA or RNA of variable length which is used in DNA or RNA samples to detect the presence of nucleotide sequences (the target amplicon) that are complementary or substantially complementary to the sequence in the probe. The probe thereby hybridizes to single-stranded nucleic acid (DNA or RNA) whose base sequence allows probe-target base pairing due to complementarity between the probe and target amplicon. The probe is linked to a surface in the detection module by covalent chemical attachment or other methods of associating an oligonucleotide with a substrate as described herein or known in the art.

To detect hybridization of the target amplicon to the probe, the target amplicon is tagged (or "labeled") with a molecular marker or label, for example a fluorescent marker or other detectable moiety such as a radioactive moiety or any enzyme capable of generating a colored or fluorescent signal in the presence of an appropriate enzyme substrate.

Visually detectable markers suitable for use in the devices and methods of the disclosure include various enzymes, prosthetic groups, fluorescent markers, luminescent markers, bioluminescent markers, and the like. Examples of suitable fluorescent moieties include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of suitable bioluminescent markers include, but are not limited to, luciferase (e.g., bacterial, firefly, click beetle and the like), luciferin, aequorin and the like. Examples of suitable enzyme systems having visually detectable signals include, but are not limited to, galactosidases, glucorinidases, phosphatases, peroxidases, cholinesterases and the like. Other suitable markers useful for detection of polynucleotides, are known to those of skill in the art.

In some embodiments, the primer sets of the disclosure comprise a detectable moiety, whereby amplification of a target region using the primer set results in production of a tagged target amplicon. In some embodiments, the detectable moiety is a biotin tag. Either forward primer, reverse primer, or both forward and reverse primers may be biotinylation. In some embodiments, one or both primers is biotin-tagged. After hybridization of the target amplicon to a probe, detection proceeds by introducing into the detection module of a first reagent, the first reagent comprising a biotin-labeled marker (e.g. a fluorescent marker or an enzyme system) is provided. In some embodiments, the first reagent comprises streptavidin-tagged horse radish peroxidase (HRP). After optionally removing excess of the first agent by washing the detection chamber, a second reagent may be provided. In some embodiments, the second reagent is substrate for a peroxidase (e.g. HRP).

The substrate can include, for example, any of tetramethylbenzidine (TMB), 3-ethylbenzothiazoline-6-sulfonic acid, o-phenylenediamine, Amplex Red, homovanillic acid, 3,3'-diaminobenzidine, 3-amino-9-ethylcarbazole, 5-Bromo-4-chloro-3-indolyl phosphate, 5-Bromo-4-chloro-3-indolyl phosphate/nitro blue tetrazolium, Fast Red (Sigma). In some embodiments, the substrate is TMB. In such embodiments, TMB in the detection module 2800 changes color from colorless to blue, and finally yellow above any positive chambers. The yellow color is produced when the detection module 2800 is heated to about 40° C. during the detection operation. In contrast, some ELISA based formats produce a color change that goes to blue or green, and does not proceed to yellow until it is exposed to a stop solution.

In other embodiments, the substrate of the substrate is a precipitating substrate formulated to catalyze the production of the visible signal OP by producing an insoluble colored product when the substrate is in contact with the enzyme. Such precipitating substrates can include, for example, TMB (3,3',5,5' tetramethylbenzidine), DAB (3,3' diaminobenzidine), or 4 CN (4-chloro-1-napthol) based membrane substrates for horseradish peroxidase enzymes, or BCIP (5-bromo-4-chloro-3-indolyl-phosphate) based membrane substrates for alkaline phosphatase. In some embodiments, the precipitating substrate can be the BioFX® TMB HRP Membrane Substrates produced by Surmodics. In some embodiments, the precipitating substrate can maintain stability when stored for up to one year in a liquid form at room temperature. In other embodiments, the precipitating substrate can maintain stability when stored for up to two years in a liquid form at room temperature. Moreover, such precipitating substrates can produce a dark color, which can be easier to visualize and interpret. In some embodiments, the precipitating substrate can produce a colorimetric output that persists for at least one hour, at least two hours, at least three hours, at least 12 hours, at least 24 hours, or at least 48 hours. Further illustrative detection methods are providing in International Patent Publication No. WO2018/005710A1, which is incorporated herein by reference in its entirety.

As used in this specification and the appended claims, the term "reagent" includes any substance that is used in connection with any of the reactions described herein. For example, a reagent can include an elution buffer, a PCR reagent (e.g., a primer), an enzyme, a substrate, a wash solution, or the like. A reagent can include a mixture of one or more constituents. A reagent can include such constituents regardless of their state of matter (e.g., solid, liquid or gas). Moreover, a reagent can include the multiple constituents that can be included in a substance in a mixed state, in an unmixed state and/or in a partially mixed state. A reagent can include both active constituents and inert constituents. Accordingly, as used herein, a reagent can include non-active and/or inert constituents such as, water, colorant or the like.

The methods described herein can be performed on any suitable molecular diagnostic device, such as any of the diagnostic devices shown and described herein or in International Patent Publication No. WO2016/109691, entitled "Devices and Methods for Molecular Diagnostic Testing," International Patent Publication No. WO2017/185067, entitled "Printed Circuit Board Heater for an Amplification Module," International Patent Publication No. WO2018/005710, entitled "Devices and Methods for Detection of Molecules Using a Flow Cell," and International Patent Publication No. WO2018/005870, entitled "Devices and Methods for Nucleic Acid Extraction," each of which is incorporated herein by reference in its entirety.

Any of the methods described herein can be performed using the molecular diagnostic test device 1000, which is shown schematically in FIGS. 1-4. The test device 1000 is configured to manipulate a biological sample to produce one or more electronic outputs indicating whether a target polynucleotide sequence is present in the biological sample, according to any of the methods described herein. In some embodiments, the test device 1000 (and any of the devices described herein) can be an integrated device that is suitable for use within a point-of-care setting (e.g., doctor's office, pharmacy or the like) or decentralized facility. In some embodiments, the methods and devices are suitable for use as an over-the-counter (OTC) diagnostic solution. Similarly stated, in some embodiments, the methods and devices are suitable for use by an untrained user (i.e., a lay user), can be supplied without a prescription, and can be performed independent of a health care facility (e.g., at the user's home). In some embodiments, the modules of the device 1000 are contained within a single housing such that the test device can be fully operated without any additional external instrument, docking station, or the like. Similarly stated, the device 1000 is a stand-alone device that includes all necessary substances, mechanisms, and subassemblies to perform any of the molecular diagnostic tests and produce the electronic outputs described herein. Such stand-alone devices do not require any external instrument to manipulate the biological samples, read the results or transmit the results, and, in some embodiments, only require connection to a power source (e.g., a connection to an A/C power source, coupling to a battery, coupling via a USB charging port, or the like) to complete the methods described herein.

In some embodiments, the device 1000 (and any of the devices shown and described herein) can be a CLIA-waived device and/or can operate in accordance with methods that are CLIA waived. Similarly stated, in some embodiments, the device 1000 (and any of the other devices shown and described herein) is configured to be operated in a sufficiently simple manner and can produce results with sufficient accuracy to pose a limited likelihood of misuse and/or to pose a limited risk of harm if used improperly. In some embodiments, the device 1000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 1000 can be configured for long term storage in a manner that poses a limited likelihood of misuse (spoilage of the reagent(s), expiration of the reagents(s), leakage of the reagent(s), or the like). In some embodiments, the molecular diagnostic test device 1000 is configured to be stored for up to about 16 months, up to about 12 months, up to about 28 months, up to about 24 months, up to about 20 months, up to about 18 months, up to 12 months, up to 6 months, or any values there between.

The test device 1000 includes a housing 1001, a sample preparation module 1200, a reaction module 1600, a detection reagent R (see FIG. 3), a detection module 1800, and an electronic detection system 1950. In some embodiments, the test device 1000 can include any other components or modules described herein, such as, for example, a valve (e.g., to control flow of reagents and/or sample, such as the valve 4340), a fluid transfer module (e.g., the fluid transfer module 4400), and/or an amplification module (e.g., the amplification module 4600). The housing 1001 can be any structure within which the modules or other components described herein are contained (or partially contained) to form an integrated device for sample preparation and/or molecular testing. The housing 1001 can be a monolithically constructed housing or can include multiple separately constructed members that are later joined together to form the housing 1001. As shown in FIG. 1, the housing defines an input opening 1021 through which a biological sample S1 can be conveyed into the test device and/or the sample preparation module 1200.

The sample preparation module 1200 defines a sample input volume that receives a biological sample S1. Referring to FIG. 1, in some embodiments, the biological sample S1 can be conveyed into the device by a sample transfer device 1110. The sample transfer device 1110 can be any suitable device, such as a pipette or other mechanism configured can be used to aspirate or withdraw the sample S1 from a sample cup, container or the like, and then deliver a desired amount of the sample via the opening 1021. The sample preparation module 1200 can include any components as described herein to manipulate the biological sample S1 for further diagnostic testing and/or to produce a solution for detection of a nucleic acid. For example, in some embodiments, the sample preparation module 1200 can include one or more heaters, one or more chambers within which the biological sample S1 can be manipulated, one or more mixing chambers, and/or certain on-board reagents (e.g., a lysing buffer, an RT enzyme, a control substance, or the like). In some embodiments, the sample preparation module 1200 can function merely as a sample holding or mixing chamber. For example, in some embodiments, the sample preparation module 1200 can contain the desired amplification reagents to facilitate a desired amplification according to any of the methods described herein. In other embodiments, the sample preparation module 1200 is configured to extract nucleic acid molecules from the biological sample S1 and can produce an input solution S2 (see FIG. 1) that is conveyed into the reaction module 1600.

In yet other embodiments, the sample preparation module 1200 can perform a series of operations, including a reverse transcription reaction. For example, in some embodiments, the sample preparation module 1200 can perform any or all of A) receiving the biological sample S1, B) mixing the biological sample with desired reagents (e.g., a positive control reagent and a reverse transcriptase), C) performing lysing operations to release target RNA from the biological sample S1, D) performing a reverse transcription reaction to produce cDNA, and E) heating the resulting solution to inactivate the reverse transcriptase. Thus, in some embodiments, the sample preparation module 1200 enables an efficient, fast RT-PCR to be performed within a single environment or module. The sample preparation module 1200 (and any of the sample preparation modules described herein) can operate in a similar manner as any of the sample preparation modules or reverse transcription modules described herein or in U.S. Patent Publication No. 2019/0169677, entitled "Portable Molecular Diagnostic Device and Methods for the Detection of Target Viruses," which is incorporated herein by reference in its entirety.

The reaction module 1600 includes defines a reaction volume and includes a heater 1630. The reaction volume can be formed from any suitable structure that defines a volume or a series of volumes within which the input solution S2 can flow and/or be reacted to produce a solution S3 that is conveyed into the detection module 1800. Thus, the reaction module 1600 can function as an amplification module, a lysis module, or any other module within which a reaction can occur to facilitate detection of the target polynucleotide sequence. In some embodiments, the reaction module 1600 can amplify the target nucleic acid molecules therein to produce an output detection solution S3 that contains a target amplicon (or multiple target amplicons) to be detected. The heater 1630 can be any suitable heater or group of heaters that can heat the input solution S2 to perform any of the amplification operations as described herein. For example, in some embodiments, the reaction module 1600 (or any of the reaction modules or amplification modules described herein) can be similar to the amplification modules shown and described in U.S. Patent Publication No. 2017/0304829, entitled "Printed Circuit Board Heater for an Amplification Module," which is incorporated herein by reference in its entirety. In other embodiments, the amplification module 1600 (or any of the amplification modules described herein) can be similar to the amplification modules shown and described in International Patent Publication No. WO2016/109691, entitled "Devices and Methods for Molecular Diagnostic Testing," which is incorporated herein by reference in its entirety. In other embodiments, the structure and/or function of the reaction module 1600 can be incorporated into the detection module 1800. Said another way, in some embodiments, the molecular diagnostic test device 1000 need not include a separate reaction chamber.

The detection module 1800 is configured to react the biological sample (identified as the processed solution S3) with one or more reagents to cause production of one or more assay signals (see the assay signals $AS_1$ in FIG. 3 and $AS_2$ in FIG. 4) to indicate presence of the target polynucleotide sequence. Although the biological sample is identified as a portion (i.e., S3) of the initial biological sample (i.e., S1) that has been processed, reacted or prepared within the sample preparation module 1200 and the reaction module 1600, in other embodiments, the portion of the biological sample that is reacted within the detection module 1800 can be any suitable portion of the initial biological sample S1. As described herein presence of the target polynucleotide sequence can indicate the presence of a target organism, whether the target organism is susceptible to a course of treatment, whether the target organism is resistant to a course of treatment, or other characteristics of the target organism. Specifically, the detection module 1800 defines a detection volume 1812 within which the biological sample and one or more reagents (see reagent R in FIG. 3) can be reacted. The reacting can be performed by combining (e.g., mixing) the reagent R and the biological sample S3 within the detection module 1800, by introducing each of the reagent R and the biological sample S3 into the detection module 1800 (either at the same time or in a sequential manner), by conveying the biological sample S3 into the detection module 1800, within which the reagent R has been stored for use, or any other suitable method for producing the desired reaction. In some embodiments, the detection module 1800 can include one or more detection surfaces to which one or more probes are attached. As described herein, such probes can be designed to permit annealing or hybridization of a target amplicon with sufficient specificity to permit detection of the presence (or absence) of a target amplicon indicating the presence of the target polynucleotide sequence. In other embodiments, the detection module can include one or more detection chambers in which different reagents or probes can be combined or reacted with the biological sample to produce a series of assay signals.

The reagent R is contained within the housing 1001 and is formulated to facilitate production of the assay signal indicating the presence of the target polynucleotide sequence. In some embodiments, the reagent R can be stored within the detection module 1800. In other embodiments, the reagent R can be stored within a reagent module (not shown in FIGS. 1-4) or any other module within the housing 1001. For example, in some embodiments, the reagent can be in a liquid state and can be stored in a sealed container within the housing 1001. In other embodiments, the reagent R can be in a solid (e.g., lyophilized) state and can be stored in a fluid path through which the biological sample flows. In some embodiments, the molecular diagnostic test device 1000 can include two or more reagents to facilitate production of the assay signal. For example, in some embodiments, the test device can include a first detection reagent formulated to facilitate production of a signal that indicates a presence of the target polynucleotide sequence (e.g., within the solution S3). The first detection reagent can comprise streptavidin-tagged horse radish peroxidase (HRP) of the compositions shown and described herein. The test device can also include a second detection reagent that is formulated to produce the assay signal (e.g., $AS_1$) when catalyzed by the first detection reagent. For example, in some embodiments, the second detection reagent can be a substrate (e.g., a precipitating substrate) of the types shown and described herein.

The assay signal(s) can be any signal indicating the presence of the target polynucleotide sequence. For example, in some embodiments, the assay signals $AS_1$, $AS_2$ can be colorimetric signals produced by the substrate (e.g., a precipitating substrate) of the types shown and described herein. In such embodiments, the detection of the assay signal is accomplished with a separate light source (not shown in FIGS. 1-4) that is passed through or onto the detection module (and the colorimetric assay signals) to determine the presence of the colorimetric assay signal. In other embodiments, however, the assay signals $AS_1$, $AS_2$ can be chemiluminescence signals produced by luminescence reaction. In such embodiments, the assay signal itself can be detected by the sensor 1974 without the need for a separate light source. In other words, the assay signal and the light signal are the same. In yet other embodiments, the assay signals $AS_1$, $AS_2$ can be fluorescence signals produced when an excitation light source excites the biological solution S3 in the detection module 1800.

The electronic detection system 1950 can be coupled to and/or within the housing 1001 of the molecular diagnostic test device 1000. In some embodiments, the electronic detection system 1950 be a portion of an overall electronic control system that controls the heaters, valves, pumps, power delivery and/or any other components of the device 1000 to facilitate the molecular testing as described herein. The electronic detection system 1950 can perform electronic detection of the assay signal $AS_1$ and produce an electronic output, as described herein. In other embodiments, the electronic detection system 1950 can both control the operation of the device and perform electronic detection of the assay signal $AS_1$. Similarly stated, the electronic detection system need not be separate from the electronic control system that controls other aspects of the device 1000 (e.g., fluid movement, heating, and the like). Thus, any functions of the electronic control system can be performed by the electronic detection system 1950 and vice-versa. The electronic system 1950 includes a processor 1951, a memory (not identified), a sensor 1974, and an output device 1953. The electronic detection system 1950 also includes one or more applications or modules that are implemented in at least one of the memory or the processor 1951. For example, in some embodiments, the electronic system 1950 includes a communication module and a digital read module (not shown in FIGS. 1-4). In some embodiments, the electronic system 1950 includes other modules for controlling the device (e.g., a flow control module, a heater control module, and a feedback module). In other embodiments, an electronic control system need not include all (or any) of these modules, and can include any other modules described herein.

The processor 1951, and any of the processors described herein can be any suitable processor for performing the methods described herein. In some embodiments, processor 1951 can be configured to run and/or execute application modules, processes and/or functions associated with the molecular diagnostic test device 1000. For example, the processor 1951 can be configured to run and/or execute the communication module, the digital read module, and/or any of the other modules described herein, and perform the methods associated therewith. The processor 1951 can be, for example, a Field Programmable Gate Array (FPGA), an Application Specific Integrated Circuit (ASIC), a Digital Signal Processor (DSP), and/or the like. The processor 1951 can be configured to retrieve data from and/or write data to memory. In some embodiments, the processor 1951 is a Bluetooth® low energy (BLE) processor.

The memory (not shown) can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth. In some embodiments, the memory stores instructions to cause the processor to execute modules, processes and/or functions associated with the molecular diagnostic test device 1000. For example, the memory can store instructions to cause the processor 1951 to execute any of the application modules described herein, and perform the methods associated therewith. In some embodiments, the memory stores information, such as one or more thresholds or ranges to be used in the methods of detection described herein.

The sensor 1974 can be any suitable switch, optical/light input sensors, temperature sensor, chemical sensor, and/or any other suitable sensor configured to receive one or more light signals (e.g., the light signals $LS_1$, $LS_2$, and/or $LS_3$) and produce a sensor signal associated with the light signal. In some embodiments, the sensor 1974 can include one or more of any of the sensors described herein. In some embodiments, the sensor 1974 can be a photodetector that is adjacent the detection module 1800 and that receives one or more light signals (e.g., the light signals $LS_1$, $LS_2$, and/or $LS_3$). In some embodiments, the sensor 1974 can be a photodetector assembly that includes multiple photodiodes. The electronic detection system 1950 can include any other sensors of the types described herein.

The output device 1953 and any of the output devices described herein can be any suitable output device for producing one or more electronic outputs (see, e.g., the electronic outputs $OP_1$ and $OP_2$) when the target polynucleotide sequence is determined to be present in the biological sample S1. For example, in some embodiments, the output device 1953 includes a light output device (e.g., light-emitting diode; LED) that produces one or more light signals to convey the test results. The output device 1953 can include multiple LEDs aligned with openings or labels on the device (not shown) corresponding to one of the conditions to be detected by the test device 1000. Thus, when the digital read module detects the presence of a polynucleotide sequence, the appropriate LED will emit light adjacent the opening, label or indicium on the test device 1000. In other embodiments, the output device 1953 includes an audible output device (e.g., a speaker) that produces one or more audible outputs to convey the test results. In yet other embodiments, the output device 1953 includes a haptic output device (e.g., a vibration mechanism) that produces one or more haptic outputs to convey the test results. In yet other embodiments, the output device 1953 includes a radio that produces a wireless signal associated with the test results. In some embodiments, the output device 1953 can include any combination of visual, audible, haptic, and/or wireless output mechanism.

In some embodiments, the output device 1953 can also function to allow information to transmitted to the electronic system 1950. Similarly stated, in some embodiments, the molecular diagnostic test device 1000 (and any of the test devices described herein) can include an input/output device (or assembly). For example, in some embodiments, the electronic system 1950 can include a touchscreen, a microphone, a transceiver, or the like, through which input can be provided to the electronic system 1950. For example, in some embodiments, the user can enter information associated with a sample type, a patient identity, or the like.

Figure 2:
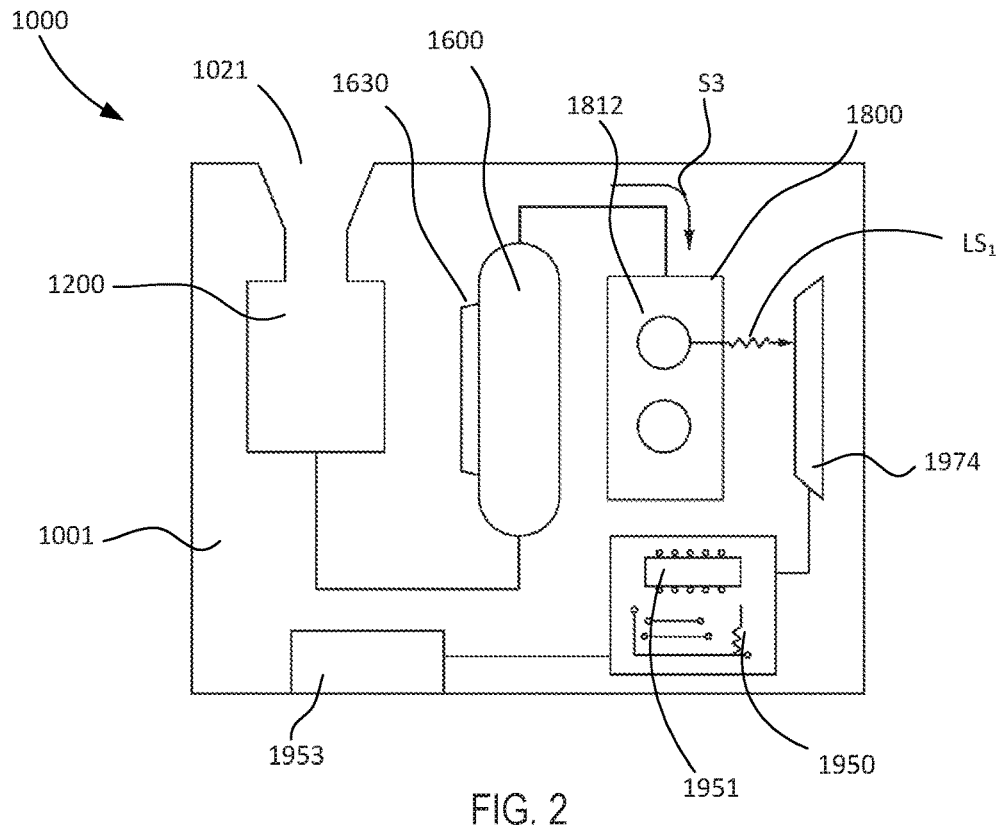
Figure 3:
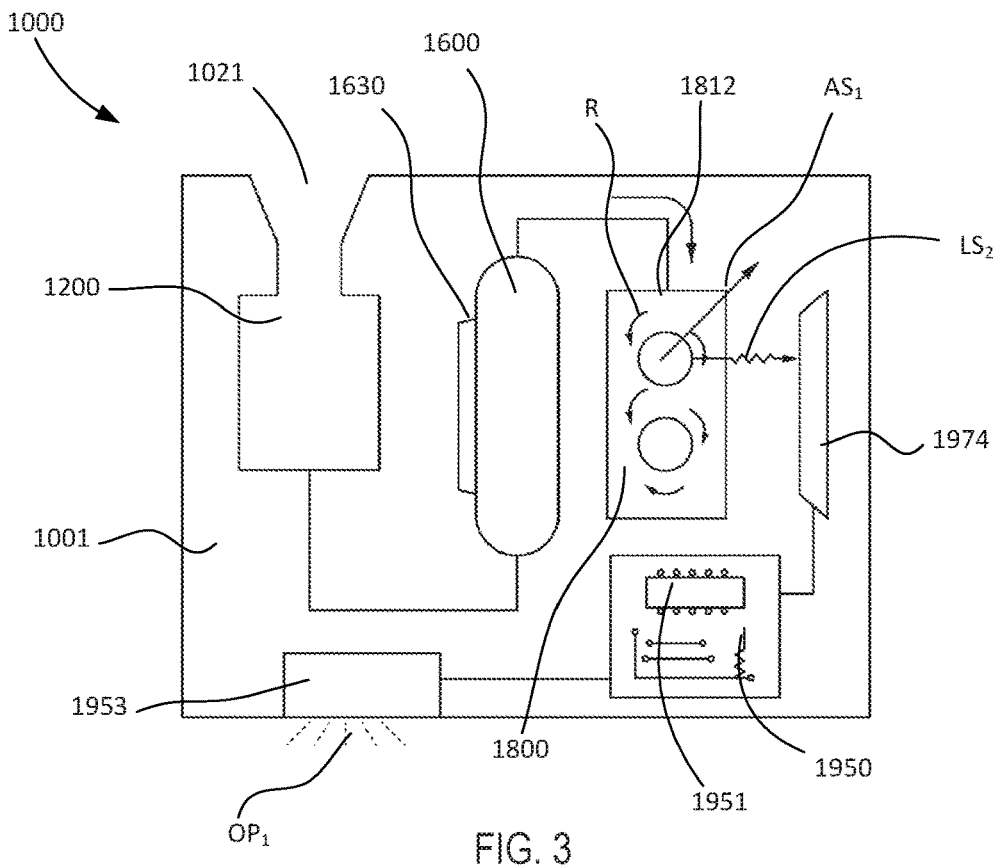

The digital read module can be a hardware and/or software module (stored in memory and/or executed in the processor 1951) of the types shown and described herein (the digital read module 3960 described herein). The digital read module is configured to receive a sensor signal (e.g., from the sensor 1974) and determine, based on the sensor signal, a test result (e.g., whether the assay signal is present, whether the target polynucleotide sequence is present, whether a positive control has properly produced a signal, etc.). Referring to FIG. 2, in some embodiments, the digital read module is configured to receive, from the sensor 1974, a first sensor signal associated with the first light signal $LS_1$ for a first time period before the biological sample S3 and the reagent R are reacted within (e.g., both introduced into) the detection volume. The first light signal $LS_1$ is therefore a background (or baseline) signal. Referring to FIG. 3, the digital read module is further configured to receive, from the photodetector assembly, a second sensor signal associated with the second light signal $LS_2$ for a second time period after the biological sample S3 and the reagent R are reacted within (e.g., after both have been introduced into) the detection volume 1812. Thus, the second light signal $LS_2$ is associated with the assay signal $AS_1$ that is produced when the biological sample S3 and the reagent R have been combined within or each has been introduced into the detection volume 1812. The digital read module is configured to determine a first magnitude associated with the first light signal and a second magnitude associated with the second light signal. The digital read module then determines, based on a comparison of the first magnitude and the second magnitude, whether the target polynucleotide sequence is present in the biological sample. In this manner, the digital read module can account for differences in the background signal and/or the assay signal $AS_1$ that can result from part-to-part variability (e.g., changes in the sensitivity of the sensor 1974, changes in the light insulation adjacent the sensor 1974 due to manufacturing variations, changes in the intensity of any excitation/detection light that may be present), changes in the testing environment (e.g., ambient pressure, temperature, humidity), different microbial loads (of the target organism to be detected) within the biological sample, or other changes.

Figure 4:
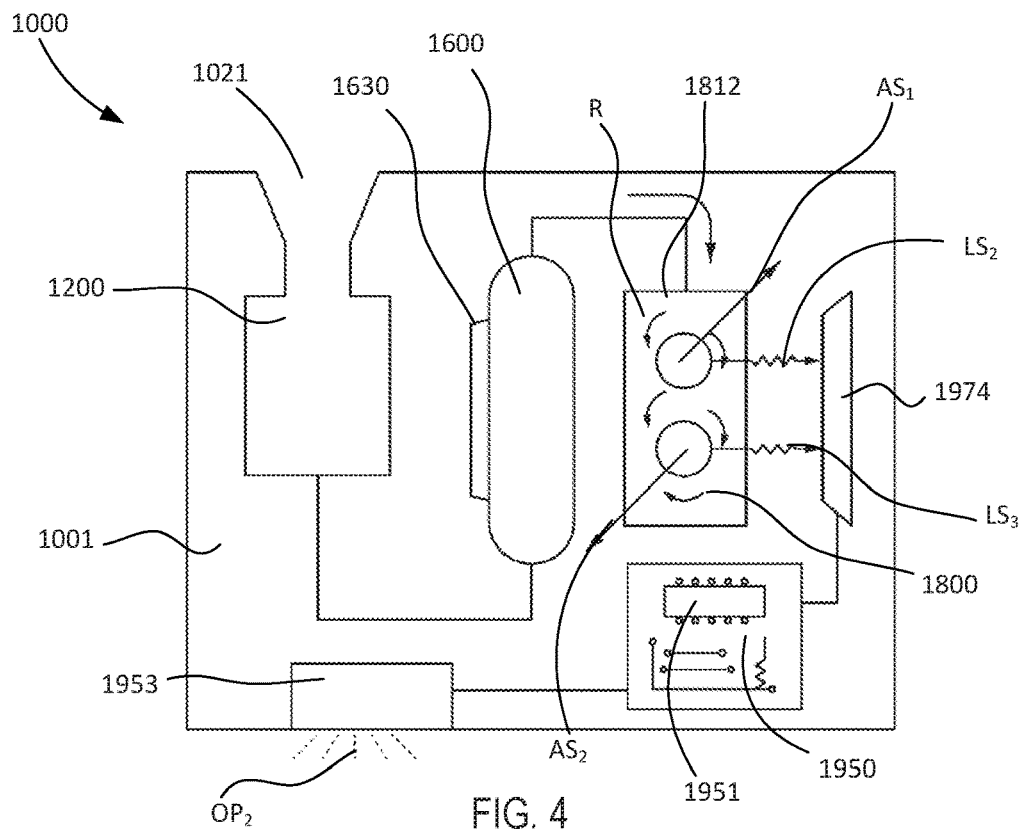

Referring to FIG. 4, in some embodiments, the molecular diagnostic test device 1000 (and any of the devices described herein) can be configured to detect the presence of multiple different polynucleotide sequences (or different portions of the same polynucleotide sequence). For example, in some embodiments, the detection module 1800 can include different portions or surfaces, each being configured to capture or retain a different polynucleotide sequence. In some embodiments, the detection module 1800 can include a first portion (or surface) that captures the target polynucleotide sequence and from which the first assay signal $AS_1$ is produced. The detection module 1800 can include a second portion (or surface) that captures a reference polynucleotide sequence and from which a second assay signal $AS_2$ is produced. The reference polynucleotide sequence can be an internal reference polynucleotide sequence (i.e., a sequence associated with the organism). In other embodiments, the reference polynucleotide sequence can be an external control polynucleotide sequence (i.e., a sequence that is added to the biological solution). For example, in some embodiments, an external control polynucleotide sequence can be a positive control that is added before during or after the biological sample is placed within the molecular diagnostic test device. The positive control can be a sequence associated with an organism that is not nonpathogenic to humans, is not harmful to the environment, and is extremely unlikely to be found on a human. Thus, if the presence of the positive control reference polynucleotide sequence is successfully detected, then the proper function of the test device 1000 can be verified. In other embodiments, the reference polynucleotide sequence can be an invariant polynucleotide sequence associated with the target polynucleotide sequence, such as a polynucleotide sequence associated with a particular polymorphism (e.g., a nucleotide at a SNP). For example, the reference polynucleotide sequence can be associated with a target allele within the target organism associated with resistance to a treatment (a resistance allele), or a target allele within the target organism associated with susceptibility to the treatment (a susceptibility allele).

In such multiplex embodiments, the digital read module is further configured to receive, from the photodetector assembly, a third sensor signal associated with the third light signal $LS_3$ for a third time period after the biological sample S3 and the reagent R are reacted within the detection volume 1812. Thus, the third light signal $LS_3$ is associated with the second assay signal $AS_2$ that is produced when the biological sample S3 and the reagent R are combined within or each has been introduced into the detection volume 1812. The third time period can be the same as the second time period. The digital read module is configured to determine a third magnitude associated with the third light signal determines, based on a comparison of the second magnitude (i.e., the second light signal $LS_2$) and the third magnitude (i.e., the third light signal $LS_3$), whether the target polynucleotide sequence is present in the biological sample. In this manner, the digital read module can account for differences between a control signal ($AS_2$) and a target signal ($AS_1$) in determining whether the target polynucleotide sequence is present. Additional functions of the digital detection module are described below, including the description of the method shown in FIG. 5.

The communication module can be a hardware and/or software module (stored in memory and/or executed in the processor 1951). The communication module is configured to receive an indication (e.g., from the sensor(s)) and/or test result information from the digital read module and cause production of one or more electronic outputs (see, e.g., $OP_1$ and $OP_2$) associated with the test result.

Figure 5:
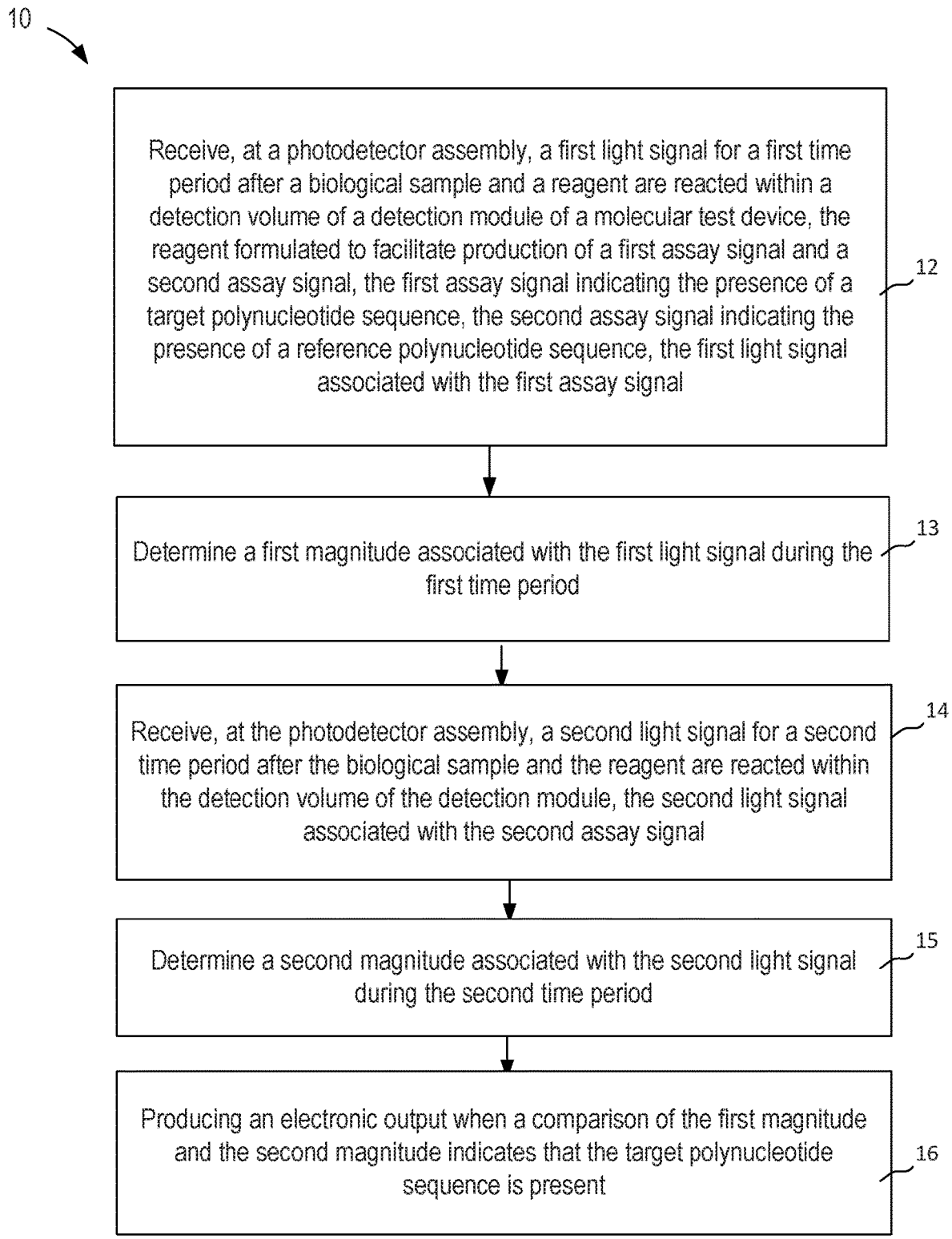
FIG. 5 is a flow chart of a method for detecting the presence of a target polynucleotide sequence within a biological sample, according to an embodiment.

The molecular diagnostic test device 1000 (and any of the molecular diagnostic test devices described herein) can perform any of the detection methods described herein. For example, FIG. 5 is a flow chart of a method 10 of detecting the presence of a target polynucleotide sequence within a biological sample, according to an embodiment. Although the method 10 is described as being performed on the device 1000, in other embodiments, the method 10 can be performed on any suitable device, such as the device 4000, the device 5000, and the device 6000 described below. The method 10 includes receiving, at a photodetector assembly (e.g., the sensor 1974), a first light signal for a first time period after the biological sample and the reagent are reacted within a detection volume (e.g., the detection volume 1812) of the detection module (e.g., the detection module 1800), at 12. The reagent is formulated to facilitate production of a first assay signal and a second assay signal. The first assay signal (e.g., the assay signal $AS_1$) indicates the presence of the target polynucleotide sequence and the second assay signal (e.g., the assay signal $AS_2$) indicates the presence of a reference polynucleotide sequence. The first light signal is associated with the first assay signal. In some embodiments, the first light signal is any one of a colorimetric signal, a chemiluminescence signal, or a fluorescence signal. The biological sample and the reagent can be reacted, introduced into, or combined within a detection volume in any suitable manner. For example, in some embodiments, the biological sample can be introduced at a first time such that only portions (e.g., a biotinylated amplicon) of the biological sample remain within the detection module. The reagent can be introduced at a second time and can react with the portion of the biological sample to produce the assay signals described herein. Thus, the biological sample and the reagent can be reacted within a detection volume without the entirety of each component residing within the detection module at the same time, such as, for example, as described below for the reaction occurring in the detection module 2800. Moreover, in some embodiments, undesired portions of the biological sample can be washed from the detection module before the reagent is introduced into the detection module.

A first magnitude associated with the first light signal is determined, at 13. The first magnitude can be any one of a slope (i.e., rate of change) of the first light signal during the first time period, an average intensity of the first light signal during the first time period, or a variability of the first light signal during the first time period.

The method 10 includes receiving, at the photodetector assembly (e.g., the sensor 1974), a second light signal for a second time period after the biological sample and the reagent are reacted within the detection volume (e.g., the detection volume 1812), at 14. The second time period can be concurrent with or partially overlap the first time period. In other embodiments, the second time period can be different from the first time period (e.g., the second time period can occur after the first time period). The second light signal is associated with the second assay signal (e.g., the assay signal $AS_2$). Thus, the second light signal is associated with the presence of the reference polynucleotide sequence. As described above, the reference polynucleotide sequence can be an internal reference polynucleotide sequence (i.e., a sequence associated with the organism) or an external control polynucleotide sequence (i.e., a sequence that is added to the biological solution).

A second magnitude associated with the second light signal is determined, at 15. The second magnitude can be any one of a slope (i.e., rate of change) of the second light signal during the second time period, an average intensity of the second light signal during the second time period, or a variability of the second light signal during the second time period. The first magnitude and/or second magnitude can be determined within the digital read module, and can include filtering the first light signal and/or the second light signal to reduce noise in the signal or by employing numerical algorithms to determine an equation representing the first light signal and/or the second light signal as a function of time. In other embodiments, the electronic system can include signal amplifiers, filter components or the like and the first magnitude and/or the second magnitude can be determined based on an amplified and filtered signal associated with the first light signal and/or the second light signal.

An electronic output is produced when a comparison of the first magnitude and the second magnitude indicates that the target polynucleotide sequence is present, at 16. In some embodiments, the comparison indicates that the target polynucleotide sequence is present when a difference between the first magnitude and the second magnitude is within a predetermined magnitude range. For example, in some embodiments, if difference between the average intensity of the first light signal (i.e., the first magnitude) and the average intensity of the second light signal (i.e., the second magnitude) is greater than a minimum value, then the target polynucleotide sequence is considered to be present. In some embodiments, if difference between the average intensity of the first light signal (i.e., the first magnitude) and the average intensity of the second light signal (i.e., the second magnitude) is greater than a minimum value but less than a maximum value, then the target polynucleotide sequence is considered to be present. In some embodiments, the comparison indicates that the target polynucleotide sequence is present when a ratio of the first magnitude and the second magnitude is within a predetermined ratio range. For example, in some embodiments, if ratio between the average intensity of the first light signal (i.e., the first magnitude) and the average intensity of the second light signal (i.e., the second magnitude) is greater than a minimum value (e.g., fifty percent), then the target polynucleotide sequence is considered to be present.

In some embodiments, the detection module includes a first detection surface and a second detection surface. The first assay signal is a first colorimetric signal produced at the first detection surface and the second assay signal is a second colorimetric signal produced at the second detection surface. The first light signal is associated with a first light beam conveyed through the first detection surface and the second light signal is associated with a second light beam conveyed through the second detection surface. Thus, the first magnitude is associated with a first attenuation of the first light beam and the second magnitude is associated with a second attenuation of the second light beam. By comparing the attenuation of the two light beams, the digital read module can determine whether the target polynucleotide sequence is present.

Figure 6:
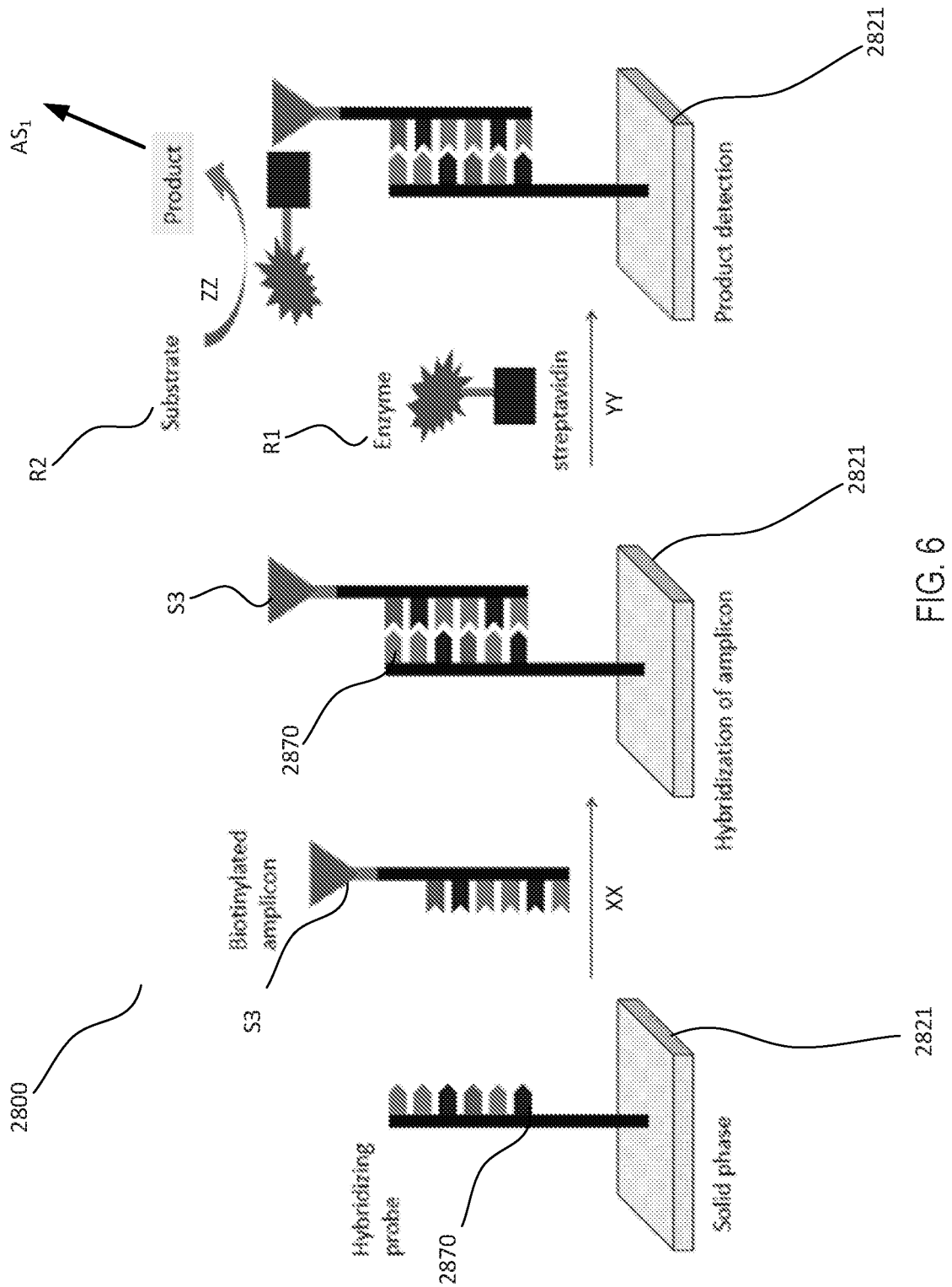
FIG. 6 is a diagram illustrating an enzyme linked reaction, according to an embodiment, resulting in the production an assay signal.

Any of the colorimetric signals described herein can be produced by any suitable reaction(s) within a detection module of a molecular diagnostic test device. For example, FIG. 6 illustrates a portion of the operation and/or features associated with an enzymatic reaction, according to an embodiment. Although FIG. 6 illustrates the enzymatic reaction as occurring with a detection module 2800, the enzymatic reaction can be conducted by or within any of the detection modules described herein. The detection module 2800 and the reaction performed therein can be configured such that the device within which the detection module 2800 is contained is a single-use device that can be used in a point-of-care setting, a decentralized facility, and/or in a user's home. Similarly stated, in some embodiments, the device that contains the detection module 2800 can be configured for use in a decentralized test facility. Moreover, the reaction shown in FIG. 6 can provide one or more assay signals (e.g., $AS_1$) that can be detected via any of the digital detection methods or via any of the digital read modules as described herein.

As shown, the detection module 2800 includes a detection surface 2821 within a read lane or flow channel. The detection surface 2821 is spotted and/or covalently bonded with a specific hybridizing probe 2870, such as an oligonucleotide. The hybridizing probe 2870 (also referred to as a capture probe) can be similar to any of the capture probes described herein. In some embodiments, the hybridizing probe 2870 is specific for a target organism, target polynucleotide sequence, and/or amplicon. The bonding of the hybridizing probe 2870 to the detection surface 4821 can be performed using any suitable procedure or mechanism. For example, in some embodiments, the hybridizing probe 2870 can be covalently bound to the detection surface 2821.

Figure 11:
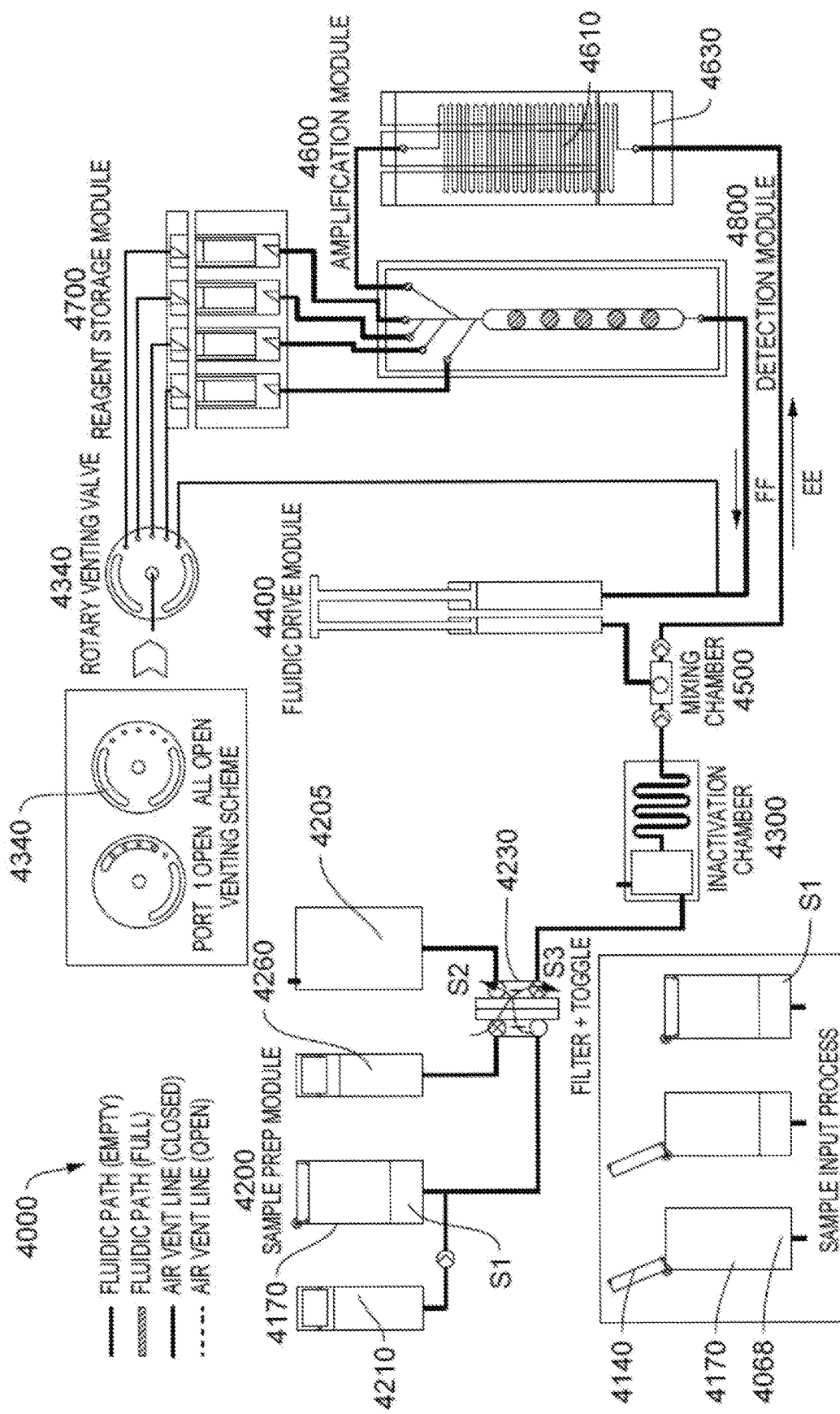
FIG. 11 is a schematic illustration of a molecular diagnostic test device, according to an embodiment.

Reference S3 illustrates the biotinylated amplicon (which is associated with the biological sample) that is produced from an amplification step such as, for example, by the amplification module 4600 of FIG. 11 (or any other amplification modules described herein). The biotin can be incorporated within the amplification operation and/or within the amplification module 4600 in any suitable manner. As shown by the arrow XX, the biotinylated amplicon S3 is conveyed within the read lane and across the detection surface 2821. The hybridizing probe 2870 is formulated to hybridize to the target amplicon S3 that is present within the flow channel and/or in proximity to the detection surface 2821. In some embodiments, the detection module 2800 and/or the detection surface 2821 is heated to incubate the biotinylated amplicon S3 in the read lane in the presence of the hybridizing probe 2870 allowing binding to occur. In this manner, the target amplicon S3 is captured and/or is affixed to the detection surface 2821, as shown. Although disclosed as being labeled with biotin, in other embodiments, the target molecules can be labeled in any suitable manner that will allow binding of the complex comprising a sample molecule binding moiety and an enzyme capable of facilitating a colorimetric reaction. For example, in some embodiments, the target molecules can be labeled with one or more of the following: streptavidin, fluorescein, Texas Red, digoxigenin, or Fucose.

As shown by the arrow YY, a first detection reagent R1 is conveyed within the read lane and across the detection surface 2821. The first detection reagent R1 can be any of the detection reagents described herein. In some embodiments, the first detection reagent R1 can be a horseradish peroxidase (HRP) enzyme ("enzyme") with a streptavidin linker. In some embodiments, the streptavidin and the HRP are cross-linked to provide dual functionality. As shown, the first detection reagent R1 is bound to the captured amplicon S3. In some embodiments, the detection module 2800 and/or the detection surface 2821 is heated to incubate the first detection reagent R1 within the read lane in the presence of the biotinylated amplicon S3 to facilitate binding.

As shown by the arrow ZZ, a second detection reagent R2 is conveyed within the read lane and across the detection surface 2821. The second detection reagent R2 can be any of the detection reagents described herein. The second detection reagent R2 can be, for example, a substrate formulated to enhance, catalyze and/or promote the production of the assay signal $AS_1$ when reacted with the second detection reagent R2. Specifically, the substrate is formulated such that upon contact with the second detection reagent R2 (the HRP/streptavidin) color molecules are produced. As such, a colorimetric assay signal $AS_1$ is developed where HRP attaches to the amplicon. The color of the assay signal $AS_1$ indicates the presence of bound amplicon: if the target pathogen, target amplicon and/or target organism is present, the color product is formed, and if the target pathogen, target amplicon and/or target organism is not present, the color product does not form.

In some embodiments the second detection reagent R2 can be continuously flowed across the detection surface 2821 to ensure that the reaction producing the color molecules does not become limited by the availability of the detection reagents. Moreover, in some embodiments, the second detection reagent R2 can be a precipitating substrate.

Any of the devices described herein can include an electronic system that detects the presence of the colorimetric signals produced by the detection module therein (e.g., the detection module 2800 or any of the other detection modules described herein). Converting the color change produced by the chemical reactions into a digital result removes end-user ambiguity when interpreting test results. Additionally, the computer-implemented methods described herein can determined based on comparison to a reference signal or other signals to improve the limit of detection and accuracy of detection. In some embodiments, the electronic system or a detection circuit therein can include one or more light emitting devices and one or more photodetectors and a computer-implemented module that determines a characteristic of the light associated with the detection surfaces of the detection module. For example, in some embodiments, a computer-implemented module can determine an amount of light attenuation through the detection surface(s). As the detection surface(s) changes color (as a result of the reactions described above), the amount of an incident light that passes through the detection surface will be reduced. By detecting the reduction in the light, the detection circuit can produce a digital signal that indicates the presence of the colorimetric signal produced by the detection surfaces.

Figure 7:
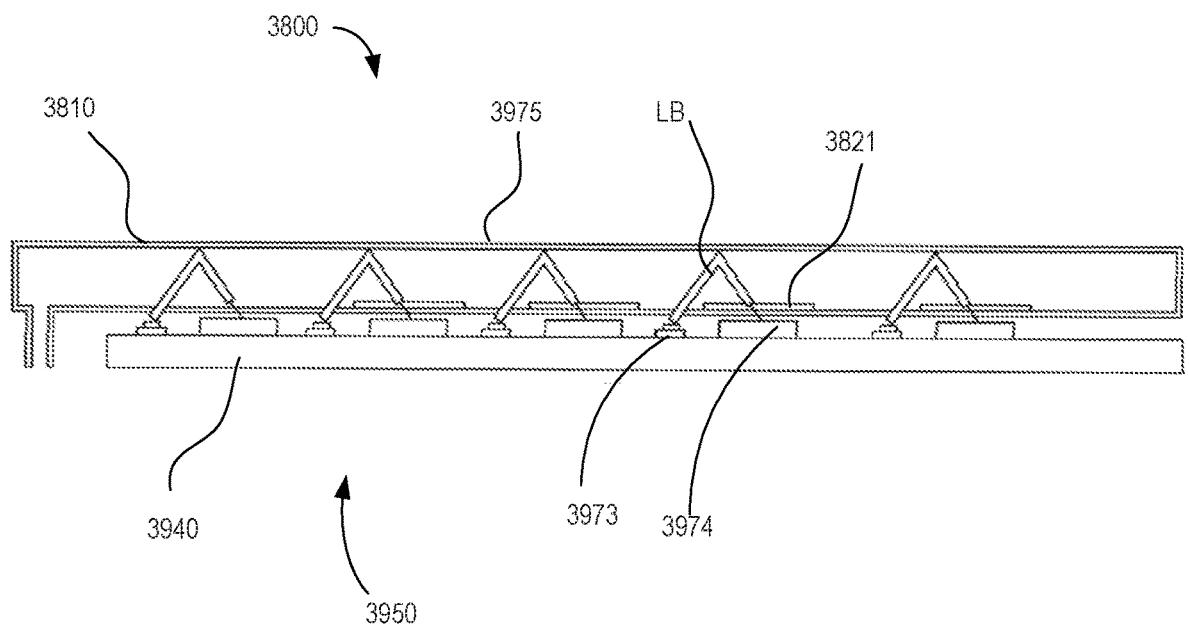
FIG. 7 is a schematic illustration of a detection module of a molecular diagnostic test device, according to an embodiment.
Figure 8:
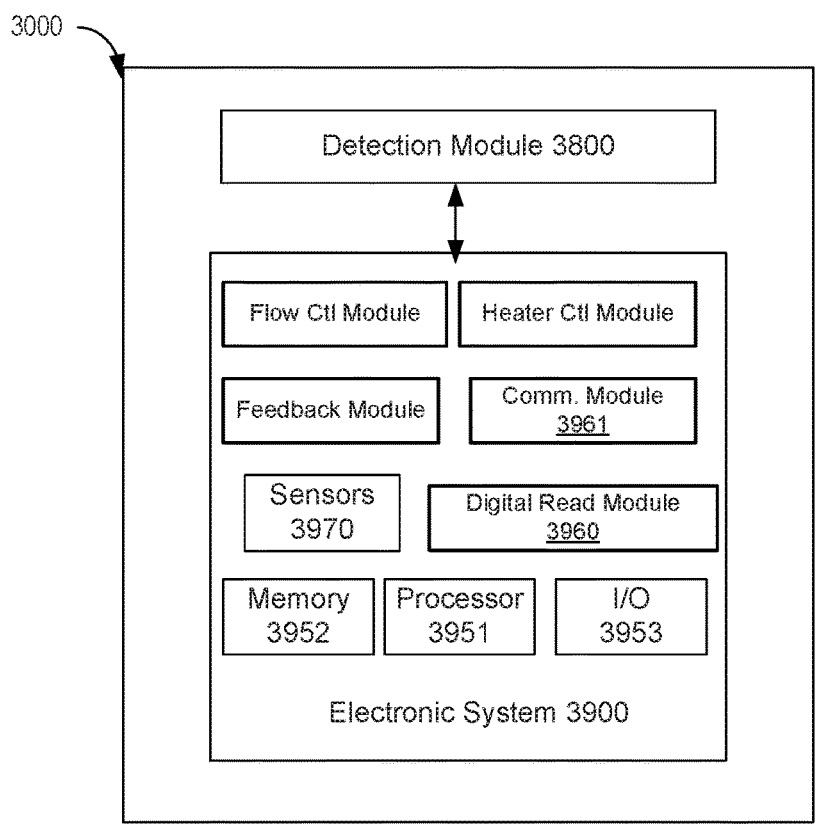
FIG. 8 is a schematic illustration of a molecular diagnostic test device including the detection module shown in FIG. 7 and an electronic system, according to an embodiment.

For example, FIGS. 7 and 8 are schematic illustrations of a portion of molecular diagnostic test device 3000 according to an embodiment that includes digital detection capability. The device 3000 includes a detection module 3800 and an electronic detection system 3950. Although not shown in FIGS. 7 and 8, the device 3000 can include any of the modules described herein, such as sample preparation module 4200, a reagent module 4700, and an amplification module 4600. Similarly stated, the detection module 3800 and the electronic detection system 3950 can be included in any of the other test devices shown herein. The detection module 3800 includes a flow cell 3810 that includes one or more detection surfaces 3821 (only one detection surface is identified in FIG. 7). The flow cell can be similar to the structure of the lid and the detection housing 4810 as shown above and the detection surfaces 3821 can be similar to any of the detection surfaces described herein. For example, the detection surfaces 3821 can be correspond to a control (or reference) detection surface, a first detection surface, a second detection surface, and a third detection surface (and any number of detection surfaces), and can have probes adhered thereto. The probes can bind to target amplicon(s), as described herein, and subsequent reaction with one or more reagents can produce a colorimetric output (also referred to as a color signal) from one or more of the detection surfaces 3821.

The electronic detection system 3950 includes a printed circuit board 3940 and a series of light-emitting diodes (LEDs) 3973 (collectively referred to as a light assembly) and photodiodes 3974 (collectively referred to as a photodetector assembly; only one pair of LEDs and photodiodes is identified). The printed circuit board 3940 can be similar to, operatively coupled to, or a portion of the printed circuit board/heater 4840 and or the printed circuit board 4940 described herein. In other embodiments, the printed circuit board 3940 can be similar to or a portion of the printed circuit board/heater 4630 described herein. The printed circuit board 3940 can include a processor 3951 (see the schematic illustration in FIG. 8), and/or any other electrical components necessary for the detection module 3800 and the electronic detection system 3950 (or portions thereof) to operate as desired. For example, the electrical components can be resistors, capacitors, inductors, switches, microcontrollers, microprocessors and/or the like. Moreover, the detection system 3950 and its components can be electrically coupled to (or form a part of) an overall electronic control system 3900 (see FIG. 8) that controls operation of the entire device 3000 (including activation of heaters, flow of fluids, etc.).

As shown, the LEDs and photodiodes are arranged on one side of the flow cell 3810, with one pair corresponding to each of the detection surfaces 3821. In this manner, when the LED is actuated, it will produce a light beam LB that is reflected from a reflective member 3975 and back through the flow cell 3810 and detection surface 3821. The photodiode under the detection surface 3821 will receive the reflected light signal. By positioning the LEDs and photodiodes in the manner (e.g., with a photodiode directly under each detection surface), substantially all light detected by the photodiode will be from the light beam LB that passes through the detection surface 3821. In this manner, when the target nucleic acid is present, it will bind to the probe (as described above). Addition of the reagent, which can be a precipitating substrate formulated to produce an insoluble colored particle when the reagent is contacted with a catalyzing agent, then produces a colored "spot" on the detection surface. As the reaction proceeds, the light beam from the LED will be attenuated as it passes through the spot, thereby yielding a reduced light signal (not shown) detected by the photodiode. Accordingly, by monitoring the signal from the photodiode, the digital read module 3960 (described below) can determine when a color spot has sufficiently formed to produce a positive result. As described herein, the sensor signals from the photodiodes 3974 (which are associated with the attenuated light signals received by the photodiodes 3974) can be manipulated by a digital read module to determine a magnitude (e.g., average value, slope, average variability) over a time period. The digital read module can also compare the magnitude of a light signal from a first detection surface with that of a second detection surface to determine whether the color spot on the first detection surface has formed sufficiently to indicate the presence of the target polynucleotide sequence.

The reflective member 3975 can be any suitable material coupled to the top of the flow cell 3810 (i.e., the side that opposite the printed circuit board). For example, in some embodiments, the reflective member 3975 can be planar, white material that reflects a high percentage of the incident light (from the LEDs) through the flow cell 3810 and the detection surface 3821. In other embodiments, the reflective member 3975 is not a separate item that is coupled to the flow cell 3810, but rather is integral to the flow cell. For example, in some embodiments, a portion of the flow cell can be constructed from a material having the desired optical properties to produce reflection of the light beam LB. In some embodiments, the reflective member 3975 can be tuned to (or associated with) a particular light wavelength. Specifically, the reflective member 3975 can be formulated to maximize the reflection (or transmission) of a certain wavelength range of the light beam LB.

In some embodiments, the detection module 3800 can include any suitable shielding or light noise attenuation mechanisms to reduce light other than that emitted by the desired LED 3973 from reaching the desired photodiode 3974. For example, in some embodiments, the detection module 3800 can include shield that surrounds a detection envelope associated with each of the detection surfaces 3821 between the bottom of the flow cell and the photodiode. In other embodiments, the detection module 3800 can include a cover or light shroud around substantially all of the detection module to reduce the likelihood that external light will impact the electronic detection system 3950. In some embodiments, the printed circuit board 3940 can include one or more alignment features (e.g., pins, protrusions, openings) that facilitate alignment with the flow cell 3810. In this manner, the detection surfaces 3821 can be aligned with the LED/photodiode pairs and any light shield components used to minimize the impact of external light (or light from adjacent LEDs) affecting the detection accuracy.

In other embodiments, the LEDs 3973 and photodiodes 3974 can be arranged in any suitable configuration. For example, although the electronic detection system 3950 is shown as having a photodiode underneath (or aligned with) the detection surface 3821 and the LED offset from the detection surface 3821, in other embodiments, the LED can be aligned with the detection surface 3821 and the photodiode can be offset from the detection surface 3821. In other embodiments, an electronic detection system can include one LED for each detection surface but only one photodiode (or light detection device) that detects light. In such embodiments, the detection module can include a scattering mechanism (not shown) that scatters a portion of the light towards the photodiode where each LED is producing the light when powered separately from other LEDs. In other embodiments, a detection circuit can include one photodiode under each of the detection surfaces but only one LED. In such embodiments, the detection module can include a scattering mechanism (not shown) that shines the light from the single LED incident upon all of the detection surfaces. Such embodiments would be well-suited for reading from all photodiodes simultaneously.

Although the detection module 3800 is shown as including both the LEDs 3973 and the photodiodes 3974 on one side of the flow cell and a reflective member 3975 on the other side, in other embodiments, a detection circuit can include an LED on one side of the flow cell 3810 and the photodiode directly opposed, on the other side of the flow cell 3810.

Figure 18:
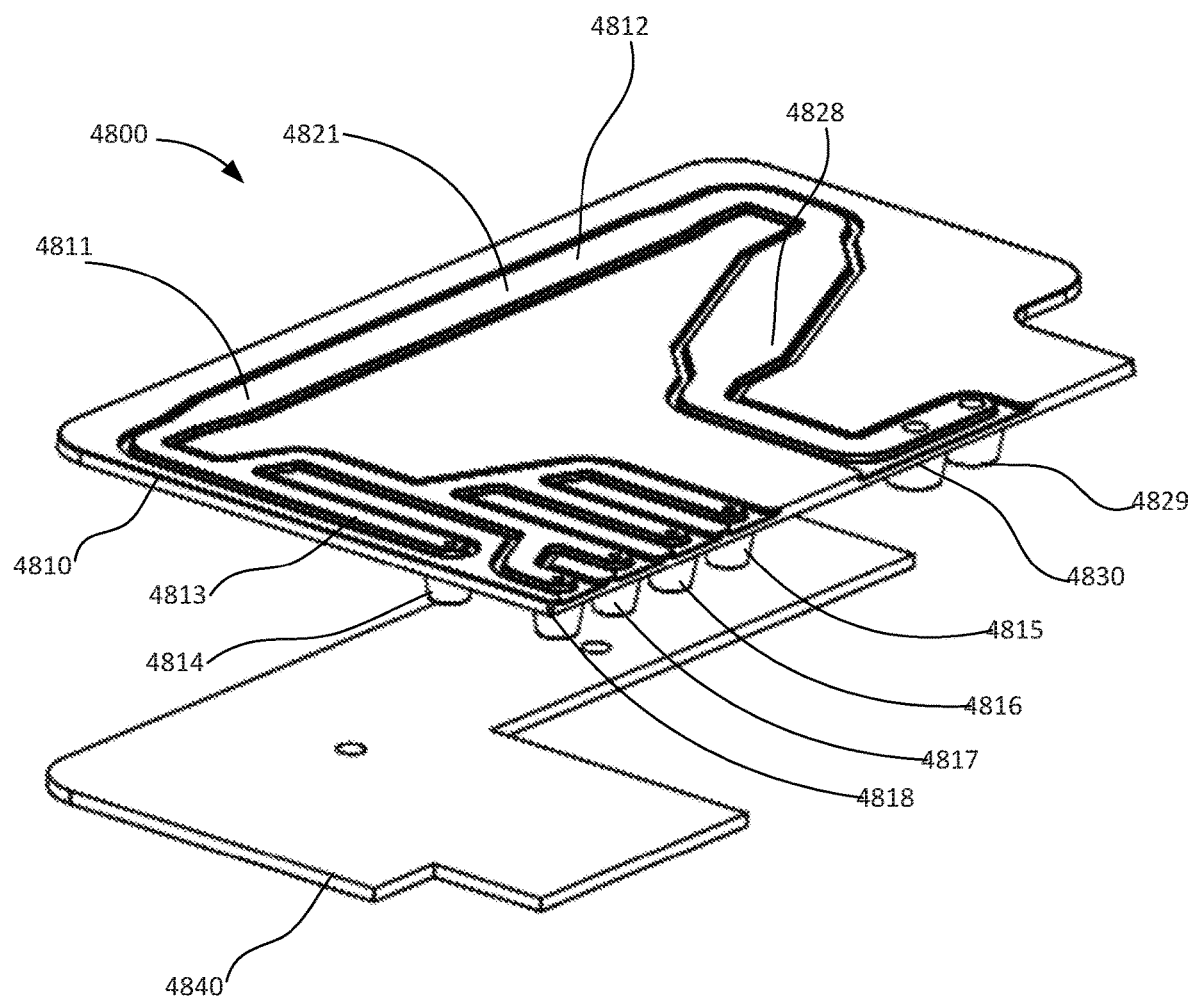
FIGS. 18 and 19 are a perspective exploded view and a front view, respectively, of a detection module of the molecular diagnostic test device shown in FIGS. 12 and 13.

FIG. 8 is a schematic illustration of the molecular diagnostic test device 3000, showing various hardware and software modules of an overall electronic control system 3900, which includes the structure and function of the electronic detection system 3950 described above. As noted above, the molecular diagnostic test device 3000 can be any of the molecular diagnostic test devices described herein. The molecular diagnostic test device 3000 can be a stand-alone device similar to the molecular diagnostic test device 4000 described herein. The molecular diagnostic test device 3000 includes or is attached to the electronic control system 3900. In some embodiments, the electronic control system 3900 can be coupled to and/or within a housing of the molecular diagnostic test device 3000, and can include one or more printed circuit boards, processors, and/or subsystems. For example, the electronic control system 3900 can include the components of the electronic system 4900 described below, including the amplification module printed circuit board heater 4630 (FIG. 16) and the detection module heater 4840 (FIG. 18). The electronic control system 3900 also includes the printed circuit board 3940 and components shown and described in FIG. 7. The electronic control system 3900 includes at least one processor 3951, at least one memory 3952, one or more sensors (collectively identified as 3970), and an input/output subsystem 3953. The electronic control system 3900 also includes a communication module 3961 and a digital read module 3960. The electronic control system 3900 also includes other modules for controlling the device (e.g., a flow control module, a heater control module, and a feedback module). Although shown as including each of these application modules, in other embodiments, an electronic control system need not include all (or any) of these modules, and can include any other modules described herein.

The processor 3951, and any of the processors described herein can be any suitable processor for performing the methods described herein. In some embodiments, processor 3951 can be configured to run and/or execute application modules, processes and/or functions associated with the molecular diagnostic test device 3000. For example, the processor 3951 can be configured to run and/or execute the communication module 3961, the digital read module 3960, and/or any of the other modules described herein, and perform the methods associated therewith. The processor 3951 can be, for example, a Field Programmable Gate Array (FPGA), an Application Specific Integrated Circuit (ASIC), a Digital Signal Processor (DSP), and/or the like. The processor 3951 can be configured to retrieve data from and/or write data to memory, e.g., the memory 3952.

The memory 3952 can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth. In some embodiments, the memory 3952 stores instructions to cause the processor 3951 to execute modules, processes and/or functions associated with the molecular diagnostic test device 3000. For example, the memory 3952 can store instructions to cause the processor 3951 to execute any of the application modules described herein, and perform the methods associated therewith.

The sensor(s) 3970 included within the electronic control system 3900 can include any number of switches, optical/light input sensors, temperature sensors, contact sensors, and/or any other suitable input device. The sensor(s) 3970 can include any of the sensors described herein. Specifically, the sensor(s) 3970 can include one or more pairs of LEDs 3973 and photodiodes 3974, as described above.

The input/output subsystem 3953 (which functions as a user interface) can include any suitable components for conveying information to, and in some embodiments, receiving information from, a user. For example, in some embodiments, the input/output subsystem 3953 can include one or more light output devices (e.g., LEDs) that produce a light signal that can be easily seen by the user to read the device. For example, in some embodiments, the input/output subsystem 3953 can include a red LED that emits red light from an opening in the device housing when an invalid test has occurred (e.g., when no signal is detected from a control detection surface). The input/output subsystem 3953 can also include a green LED that emits green light from an opening in the device housing when a signal from the control detection surface has been detected, indicating that a valid test has occurred.

In some embodiments, the input/output subsystem 3953 can include LEDs that are aligned with one of the control windows or control openings defined by the housing. For example, referring to the device 4000 shown in FIGS. 12 and 13, the input/output subsystem 3953 can include LEDs aligned with each of the openings 4011 corresponding to one of the conditions to be detected by the test device. For example, the input/output subsystem 3953 can include an LED positioned to emit light through the opening adjacent the "target bacteria" indicium on the housing 4010. Thus, when the digital read module 3960 detects the presence of a signal from the detection surface from which a colorimetric signal is produced when the target polynucleotide sequence is present in the biological sample, the LED will emit light adjacent the "target bacteria" indicium on the housing 4010.

As another non-limiting example, the input/output subsystem 3953 can include an LED positioned to emit light through the opening adjacent the "drug resistant" indicium on the housing 4010. Thus, when the digital read module 3960 detects the presence of a signal from the detection surface from which a colorimetric signal is produced when a polynucleotide sequence associated with drug resistance (also referred to as a -R allele) is present in the biological sample, the LED will emit light adjacent the "drug resistant" indicium on the housing 4010. Further, in some embodiments, the input/output subsystem 3953 can include an LED positioned to emit light through the opening adjacent the "susceptible to drug" indicium on the housing 4010. Thus, when the digital detection module 3960 detects the presence of a signal from the detection surface from which a colorimetric signal is produced when a polynucleotide sequence associated with drug susceptibility (also referred to as a -S allele) is present in the biological sample, the LED will emit light adjacent the "susceptible to drug" indicium on the housing 4010.

In other embodiments, the input/output subsystem 3953 can produce any suitable electronic output to be read by the user. Such electronic outputs can include an audible output (e.g., produced by a speaker), a haptic (vibratory) output, a light output (e.g., as described herein), and a wireless signal.

In some embodiments, the input/output subsystem 3953 can include a monitor or screen that displays visual elements to a user. The screen can be a touch screen upon which a series of graphical user interface elements (e.g., windows, icons, input prompts, graphical buttons, data displays, notification, or the like) can be displayed. In some embodiments, the graphical user interface elements (not shown) are produced by a user interface module. In such embodiments, the user can also enter information into the electronic system 3900 via the input/output subsystem 3953.

The communication module 3961 can be a hardware and/or software module (stored in memory 3952 and/or executed in the processor 3951). The communication module 3961 is configured to receive an indication (e.g., from the sensor(s)) and/or test result information from the digital detection module 3960 and transmit an output signal associated with the test result. The output signal(s) are produced to the user via the input/output subsystem 3953, as described above.

The digital read module 3960 can be a hardware and/or software module (stored in memory 3952 and/or executed in the processor 3951). The digital read module 3960 is configured to receive a signal (e.g., from one or more photodiodes 3974) and determine, based on the signal, whether a color signal from the corresponding detection surface is present. Functions of the digital read module 3960 are described with respect to the device 1000 and the device 2000 above, and also the method 20 (FIG. 9) and accompanying plot (FIG. 10).

Figure 9:
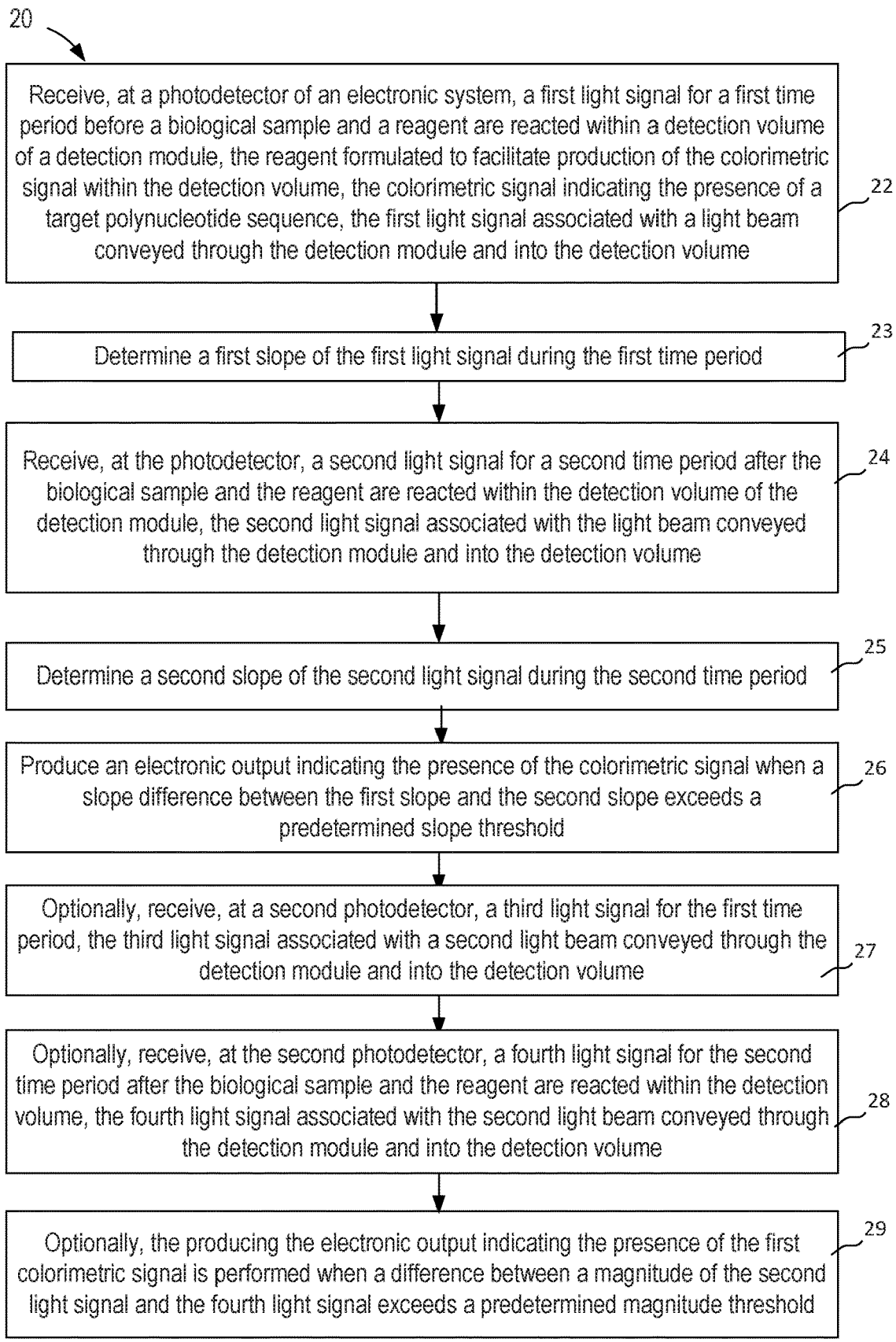
FIG. 9 is a flow chart of a method for detecting the presence of a target polynucleotide sequence within a biological sample, according to an embodiment.
Figure 10:
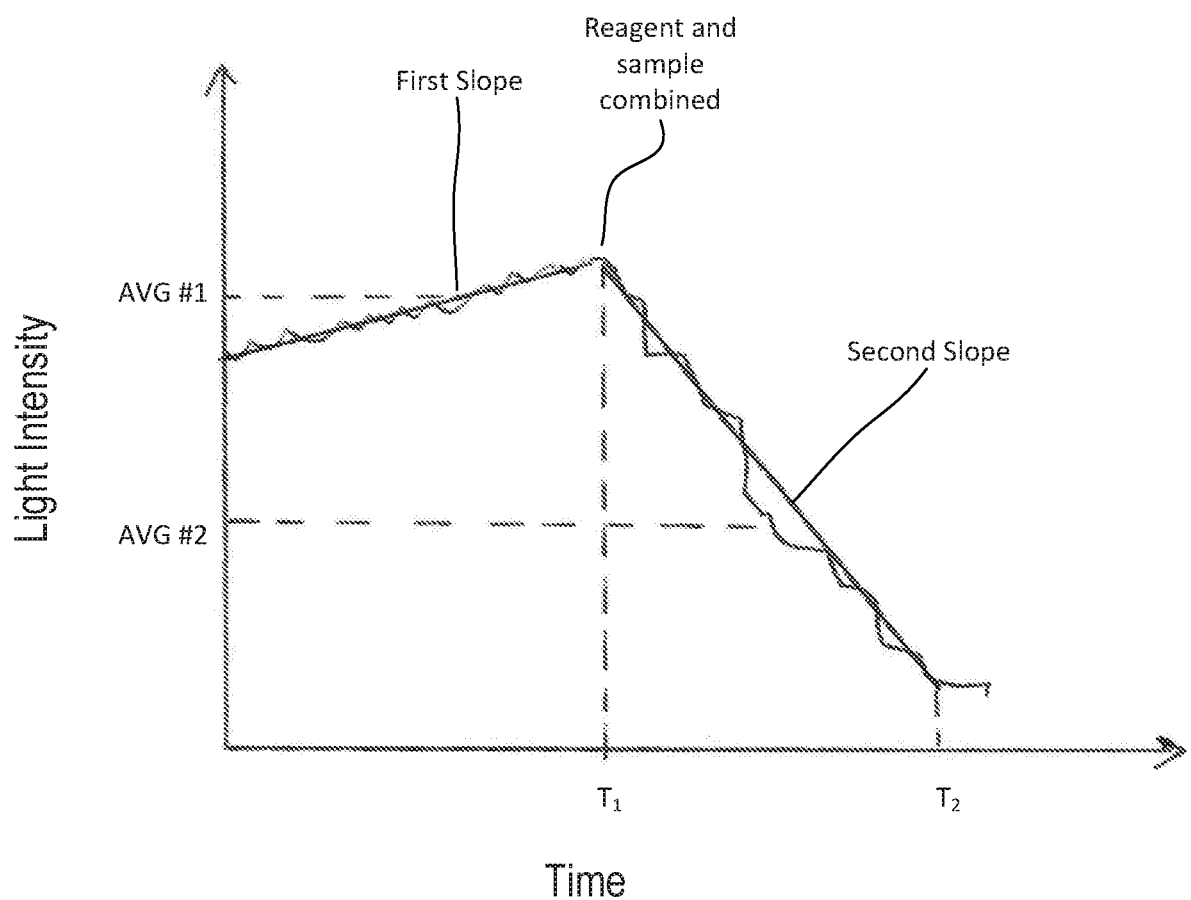
FIG. 10 is a plot showing a representative light signal produced by an electronic system of a molecular diagnostic test device, according to an embodiment.

FIG. 9 is a flow chart of a method 20 of detecting the presence of a target polynucleotide sequence within a biological sample, according to an embodiment. Although the method 20 is described as being performed on the device 3000, in other embodiments, the method 20 can be performed on any suitable device, such as the device 4000, the device 5000, and the device 6000 described below. Moreover, although the method 20 is described along with the graph showing a representative light signal produced by an electronic system, the method 20 is not limited to detection of only light signals as characterized in FIG. 10. The method 20 includes receiving, at a photodetector assembly (e.g., the photodetectors 3974), a first light signal for a first time period before the biological sample and the reagent are reacted within a detection volume of the detection module (e.g., the detection module 3800), at 22. The reagent is formulated to facilitate production of a colorimetric signal (which functions as an assay signal) within or from the detection module. For example, the colorimetric signal can be produced from one of the detection surfaces 3821 described above. The colorimetric signal indicates the presence of the target polynucleotide sequence. The first light signal is associated with a light beam conveyed through the detection module (e.g., the light beam LB shown in FIG. 7). Thus, the first light signal can be the amount of attenuation of the light beam LB as it passes through the detection module and the colorimetric signal that may be produced therein.

A first slope (i.e., rate of change) of the first light signal during the first time period is determined, at 23. Referring to FIG. 10, the first time period is represented on the x-axis as being the time period before time $T_1$, which is before the reagent and the biological sample are reacted within the detection module. During the first time period, the intensity of the first light signal can be changing due to environmental conditions associated with the device 3000 and/or the detection module 3800. For example, in some embodiments, the temperature of the detection module and/or other components within the device (e.g., an amplification module) is changed to facilitate the production of the colorimetric signal(s). Specifically, in some embodiments, the detection module is heated to facilitate binding of the amplicon (i.e., the target polynucleotide sequence) to the detection surface. As a result, the temperature of the electronic detection system 3950, including the photodetector (e.g., the photodetectors 3974) and the light source(s) that produce the light beam (e.g., LEDs 3973), is increased during this heating phase. Subsequently, when the detection heater is disabled, the temperature of the electronic detection system 3950 will decrease. Additionally, the introduction of constituents into the detection module can also change the heat transfer characteristics of the detection module and the electronic detection system 3950. Because the output of the LEDs increases as the operating temperature decreases and because the performance of the photodetectors may also change as a function of temperature, it is not practical to obtain a constant background signal in the stand-alone device 3000 (or the other devices described herein). As such, the method 20 (and the digital read modules described herein) establish a background signal based on the slope of the first light signal (i.e., the first slope). In other embodiments, the method can include determining a first average intensity of the first light signal (e.g., AVG #1) or a variability of the first light signal during the first time period.

The method 20 includes receiving, at the photodetector assembly (e.g., the photodetectors 3974), a second light signal for a second time period after the biological sample and the reagent are reacted within the detection volume, at 24. The second light signal is associated with the light beam conveyed through the detection module (e.g., the light beam LB shown in FIG. 7). Thus, the second light signal can be the amount of attenuation of the light beam LB as it passes through the detection module and the colorimetric signal that may be produced therein. The reacting can be performed by combining (e.g., mixing) the reagent and the biological sample within the detection module, by introducing each of the reagent and the biological sample into the detection module (either at the same time or in a sequential manner), by conveying the biological sample into the detection module, within which the reagent has been stored for use, or any other suitable method for producing the desired reaction.

A second slope (i.e., rate of change) of the second light signal is determined, at 25. Referring to FIG. 10, the second time period is represented on the x-axis as being the time period between time $T_1$ and time $T_2$, which is after the reagent and the biological sample are reacted within the detection module. During the second time period, the intensity of the second light signal can change due to both the changing environmental conditions and also as a result of the colorimetric signal that may be formed. For example, as shown in FIG. 10, in some embodiments, a high load of the target polynucleotide sequence in the biological sample will result in a very dark colorimetric signal being formed very rapidly. In this instance, the intensity of the second light signal is dominated by the attenuation of the colorimetric signal and only minimally impacted by the change in environmental conditions (e.g., temperature). As a result, the second light signal rapidly decreases and the second slope is a negative slope with a high value. In other embodiments, a low load of the target polynucleotide sequence in the biological sample will result in a light colorimetric signal being formed slowly during the second time period. In such instances, the intensity of the second light signal may be more equally affected by the attenuation of the colorimetric signal and the change in environmental conditions (e.g., temperature). As a result, the second light signal may have a less pronounced change over the second time period. In yet other embodiments, absence of the target polynucleotide sequence in the biological sample will result in substantially no colorimetric signal being formed during the second time period. In such instances, the intensity of the second light signal is dominated by the change in environmental conditions (e.g., temperature).

As described herein, the biological sample and the reagent can be reacted, introduced, or combined within a detection volume in any suitable manner. For example, in some embodiments, the biological sample can be introduced at a first time such that only portions (e.g., a biotinylated amplicon) of the biological sample remain within the detection module. The reagent can be introduced at a second time and can react with the portion of the biological sample to produce the assay signals described herein. Thus, the biological sample and the reagent can be reacted within a detection volume without the entirety of each component residing within the detection module at the same time. Moreover, in some embodiments, undesired portions of the biological sample can be washed from the detection module before the reagent is introduced into the detection module.

An electronic output is produced when a comparison of the first slope and the second slope indicates that the target polynucleotide sequence is present, at 26. In some embodiments, the comparison indicates that the target polynucleotide sequence is present when a difference between the first slope and the second slope is within a predetermined magnitude range. For example, in some embodiments, if difference between the first slope and the second slope is greater than a minimum value, then the colorimetric signal (and thus the target polynucleotide sequence) is considered to be present. In other embodiments, the comparison indicates that the target polynucleotide sequence is present when a ratio of the first slope and the second slope is within a predetermined ratio range. For example, in some embodiments, if ratio between the first slope and the second slope is greater than a minimum value (e.g., fifty percent), then the colorimetric signal (and thus the target polynucleotide sequence) is considered to be present. In yet other embodiments, the comparison can be based on a change of sign of the first slope and the second slope (i.e., a change from a positive slope to a negative slope).

By basing the determination of whether the colorimetric signal (and thus the target polynucleotide sequence) is present on a comparison with a background signal that is unique to the particular device 3000, the digital read module can account for differences in the background signal and/or the colorimetric signal that can result from part-to-part variability (e.g., changes in the sensitivity of the sensor 3974, changes in the light insulation adjacent the sensor 3974 due to manufacturing variations, changes in the intensity of any excitation/detection light that may be present), changes in the testing environment (e.g., ambient pressure, temperature, humidity), different microbial loads (of the target organism to be detected) within the biological sample, or other changes.

In some embodiments, the detection module includes a first detection surface and a second detection surface. The first colorimetric signal is produced at the first detection surface and the second colorimetric signal is produced at the second detection surface. The first light signal is associated with a first light beam conveyed through the first detection surface and the second light signal is associated with a second light beam conveyed through the second detection surface. In such embodiments, the method 20 can optionally include receiving, at a second photodetector, a third light signal for the first time period, the third light signal associated with a second light beam conveyed through the detection module and into the detection volume, at 27. A fourth light signal is then received for the second time period after the biological sample and the reagent are reacted within the detection volume of the detection module, at 28. The fourth light signal associated with the second light beam conveyed through the detection module and into the detection volume. The method further optionally includes producing the electronic output indicating the presence of the first colorimetric signal when a difference between a magnitude of the second light signal (i.e., from the first detection surface) and the fourth light signal (i.e., from the second detection surface) exceeds a predetermined magnitude threshold. The second magnitude is associated with a first attenuation of the first light beam and the fourth magnitude is associated with a second attenuation of the second light beam. By comparing the attenuation of the two light beams, the digital read module can determine whether the target polynucleotide sequence is present.

In some embodiments, the method 20 (and any of the methods described herein) can optionally include producing one or more flow signals that cause flow of constituents within the detection module. For example, in some embodiments, the method 20 can optionally include producing sample flow signal to cause the biological sample to flow into the detection module and producing a reagent signal to cause the reagent to flow from a reagent module into the detection module. Because the flow of the constituents within the detection module can impact the environmental conditions (e.g., temperature of the detection module) and formation of the colorimetric signal(s), controlling the flow of such constituents during (or in consideration of) the digital read operation can produce more accurate results.

FIG. 11 is a schematic illustration of a molecular diagnostic test device 4000 (also referred to as a "test device" or "device") that can include an electronic detection system of the types shown and described herein (e.g., the electronic detection systems 1950, 2950, 3950). The schematic illustration describes the primary components of the test device 4000 as shown in FIGS. 12-19. Although the schematic illustration of FIG. 11 does not show an electronic detection system, it is understood that any of the electronic detection systems described herein can be included in the device 4000. Moreover, as described below, the device 4000 includes the electronic control system 4900, which in addition to including electronic components (motors, circuit boards, processors) and software for controlling the operation of the device 4000, can include any of the structure and function of any of the electronic detection systems described herein. Accordingly, although FIGS. 11-19 do not show details of a light source and a photodetector for detecting the presence of a colorimetric signal produced within the detection module 4800, it is understood that the device 4000 can include any such components of the electronic detection systems described herein.

The test device 4000 is an integrated device (i.e., the modules are contained within a single housing) that is suitable for use within a point-of-care setting (e.g., doctor's office, pharmacy or the like) or a decentralized test facility. In some embodiments, the device 4000 is suitable for use as an over-the-counter (OTC) diagnostic solution. Similarly stated, in some embodiments, the device 4000 (and methods performed with the device) are suitable for use by an untrained user (i.e., a lay user), can be supplied without a prescription, and can be performed independent of a health care facility (e.g., at the user's home). In some embodiments, the device 4000 can have a size, shape and/or weight such that the device 4000 can be carried, held, used and/or manipulated in a user's hands (i.e., it can be a "handheld" device). In other embodiments, the test device 4000 can be a self-contained, single-use device. In some embodiments, the test device 4000 can be configured with lock-outs or other mechanisms to prevent re-use or attempts to re-use the device.

Further, in some embodiments, the device 4000 can be a CLIA-waived device and/or can operate in accordance with methods that are CLIA waived. Similarly stated, in some embodiments, the device 4000 (and any of the other devices shown and described herein) is configured to be operated in a sufficiently simple manner, and can produce results with sufficient accuracy to pose a limited likelihood of misuse and/or to pose a limited risk of harm if used improperly. In some embodiments, the device 4000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 4000 can be configured for long term storage in a manner that poses a limited likelihood of misuse (spoilage of the reagent(s), expiration of the reagents(s), leakage of the reagent(s), or the like). In some embodiments, the molecular diagnostic test device 4000 is configured to be stored for up to about 36 months, up to about 32 months, up to about 26 months, up to about 24 months, up to about 20 months, up to about 48 months, or any values there between.

The test device 4000 is configured to manipulate a biological sample S1 to produce one or more output signals associated with one or more target amplicons (e.g., an amplicon to detect the presence of a target organism, an amplicon associated with a target SNP), and can be used to perform any of the molecular diagnostic methods described herein. Specifically, the device 4000 includes a sample preparation module 4200, an inactivation module 4300 (also referred to as a lysing module), a fluidic drive (or fluid transfer) module 4400, a mixing chamber (which can function as an amplification reagent module) 4500, an amplification module 4600, a detection module 4800 and an electronic control system 4900 (not shown in FIG. 11, see FIG. 16). The test device and certain components therein can be similar to any of the molecular test devices shown and described herein or in International Patent Publication No. WO2016/109691, entitled "Devices and Methods for Molecular Diagnostic Testing," which is incorporated herein by reference in its entirety. Accordingly, a detailed description of certain modules (e.g., the fluidic drive module 4400) is not provided herein.

Figure 12:
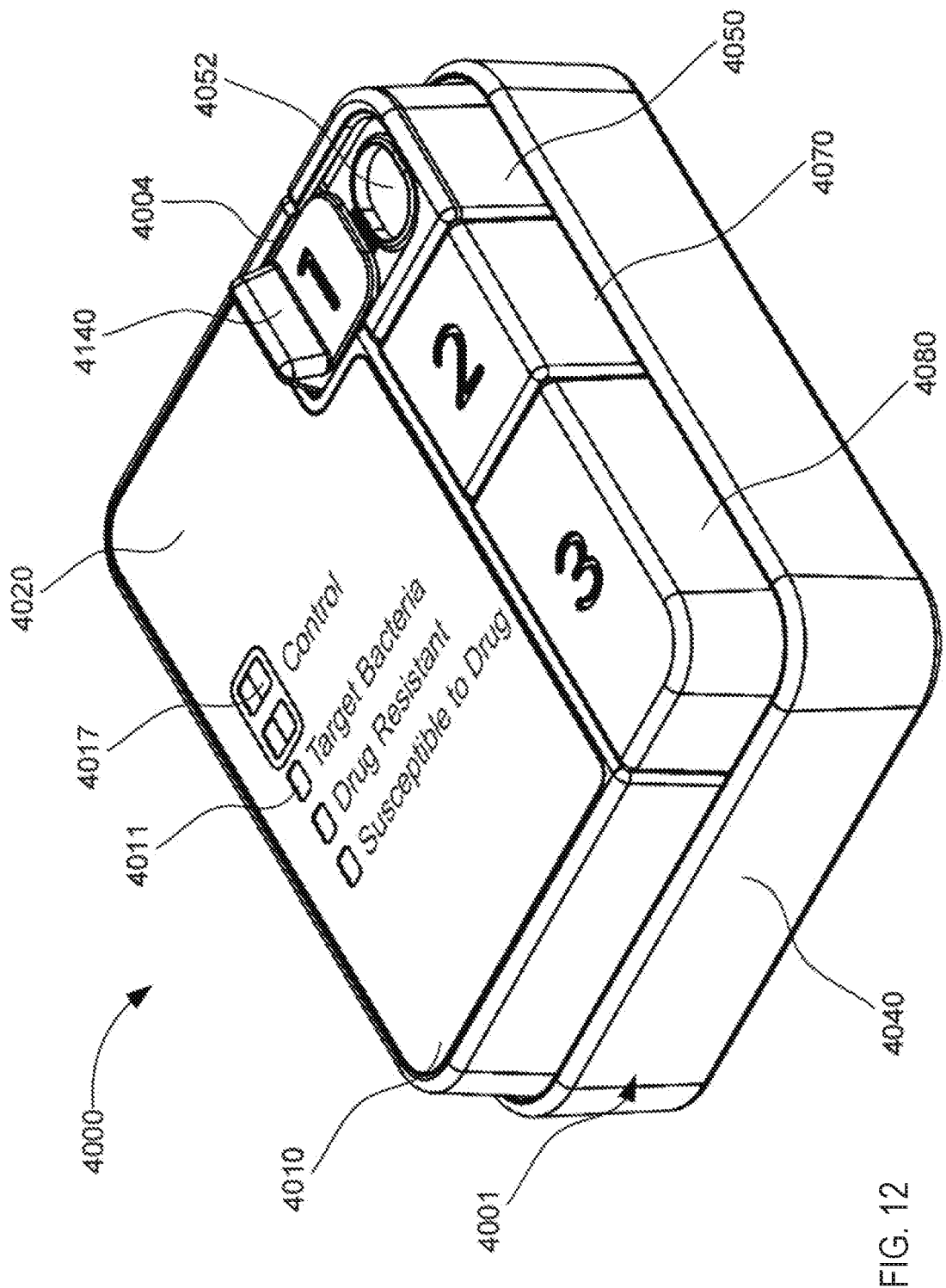
FIGS. 12 and 13 are a perspective view and a top view, respectively, of a molecular diagnostic test device, according to an embodiment.
Figure 13:
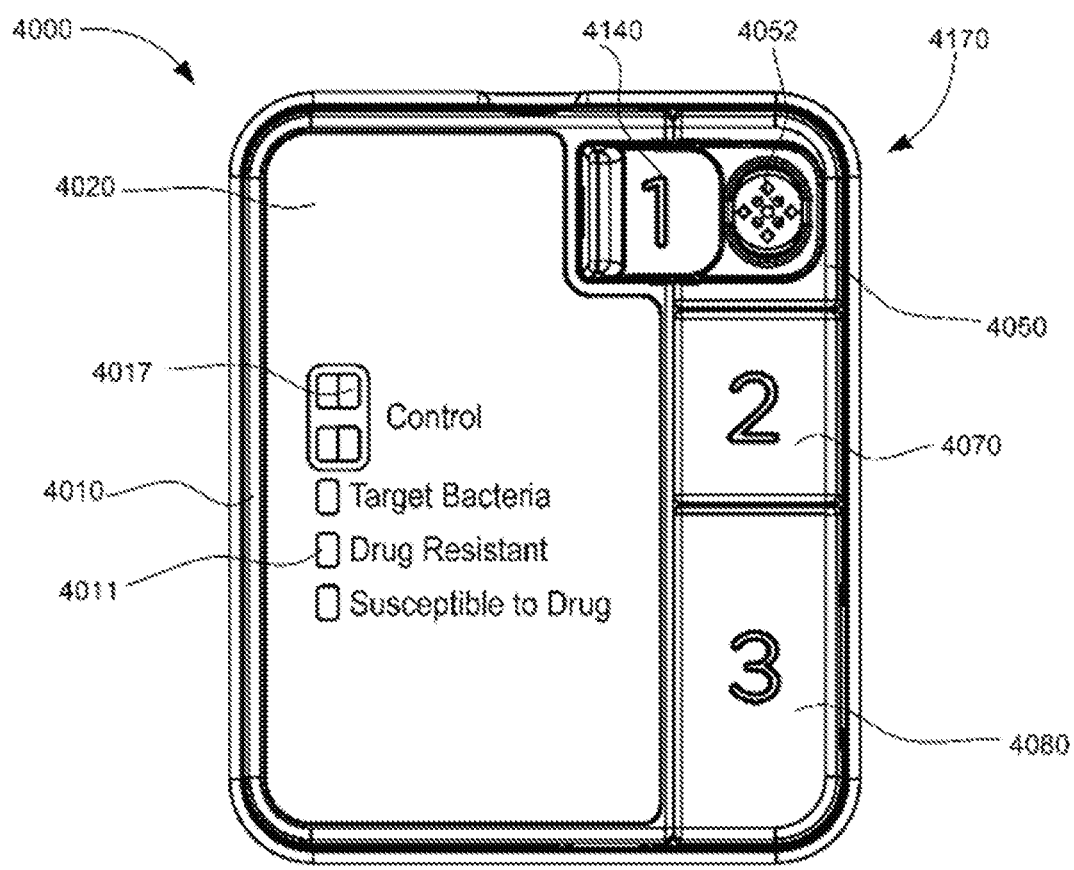
Figure 14:
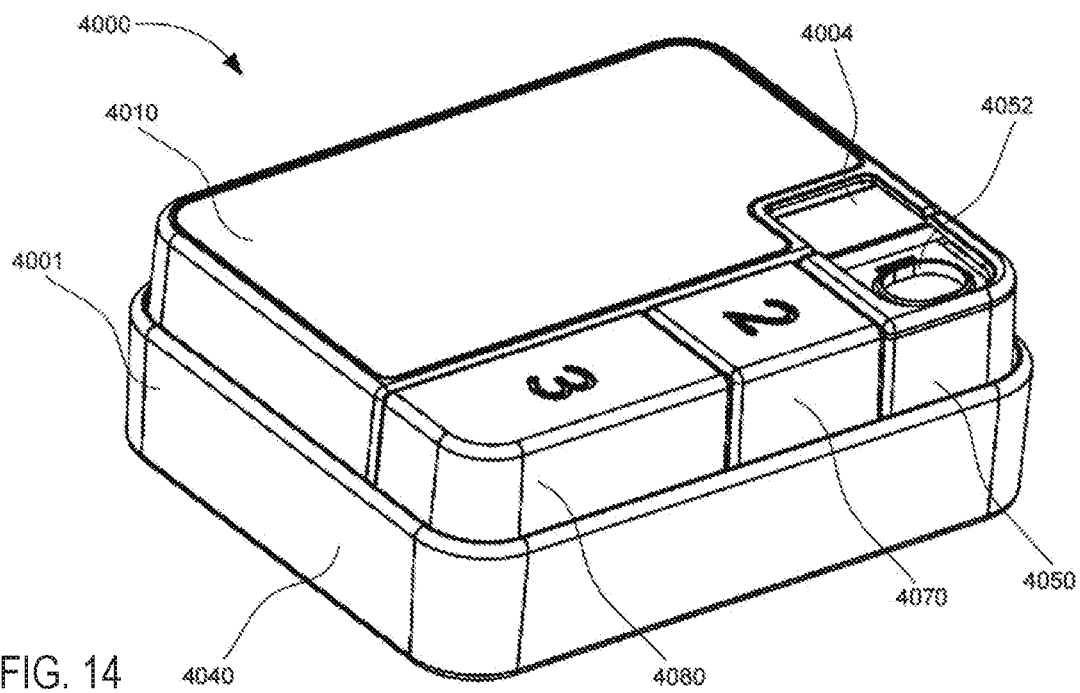
FIG. 14 is a perspective view of the molecular diagnostic test device shown in FIGS. 12 and 13, with the lid removed to show the sample input opening.
Figure 15:
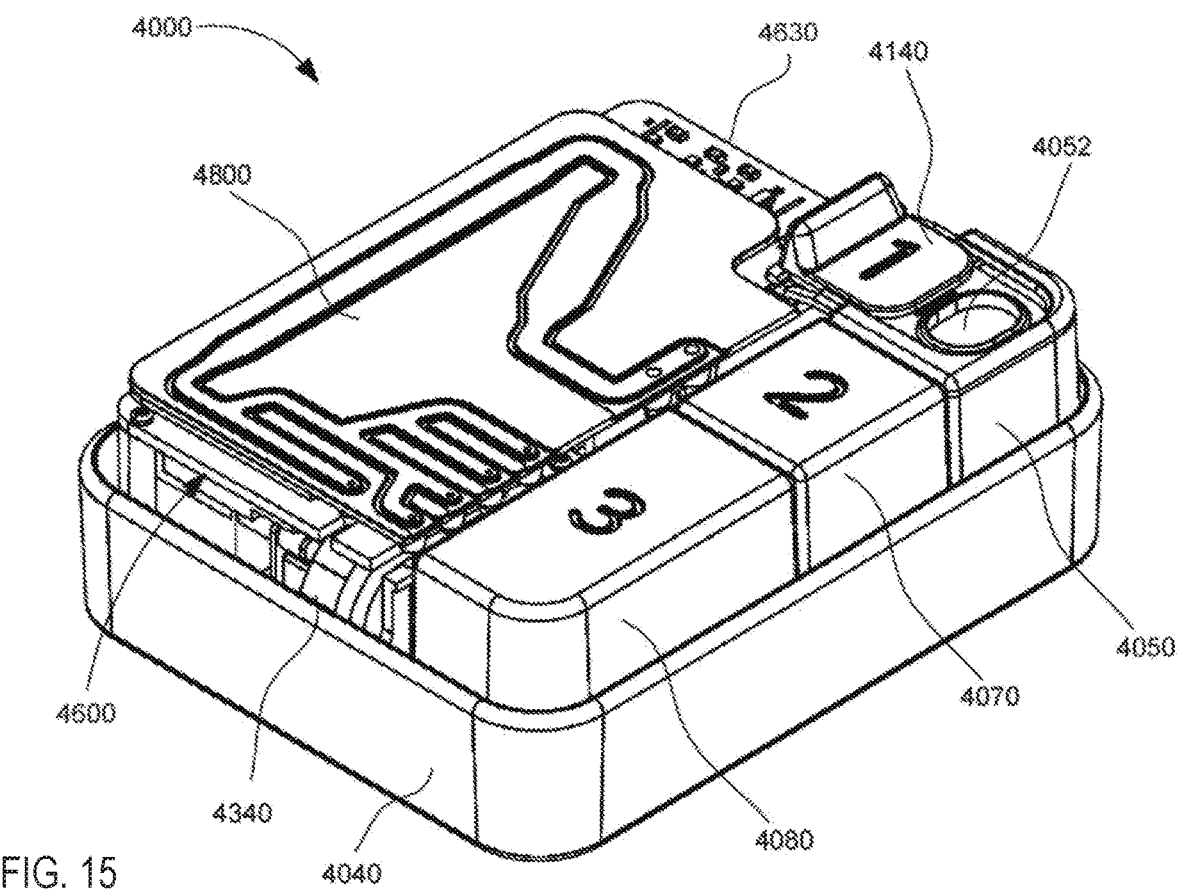
FIG. 15 is a perspective view of the molecular diagnostic test device shown in FIGS. 12 and 13 with the top portion of the housing removed to show the internal components.
Figure 16:
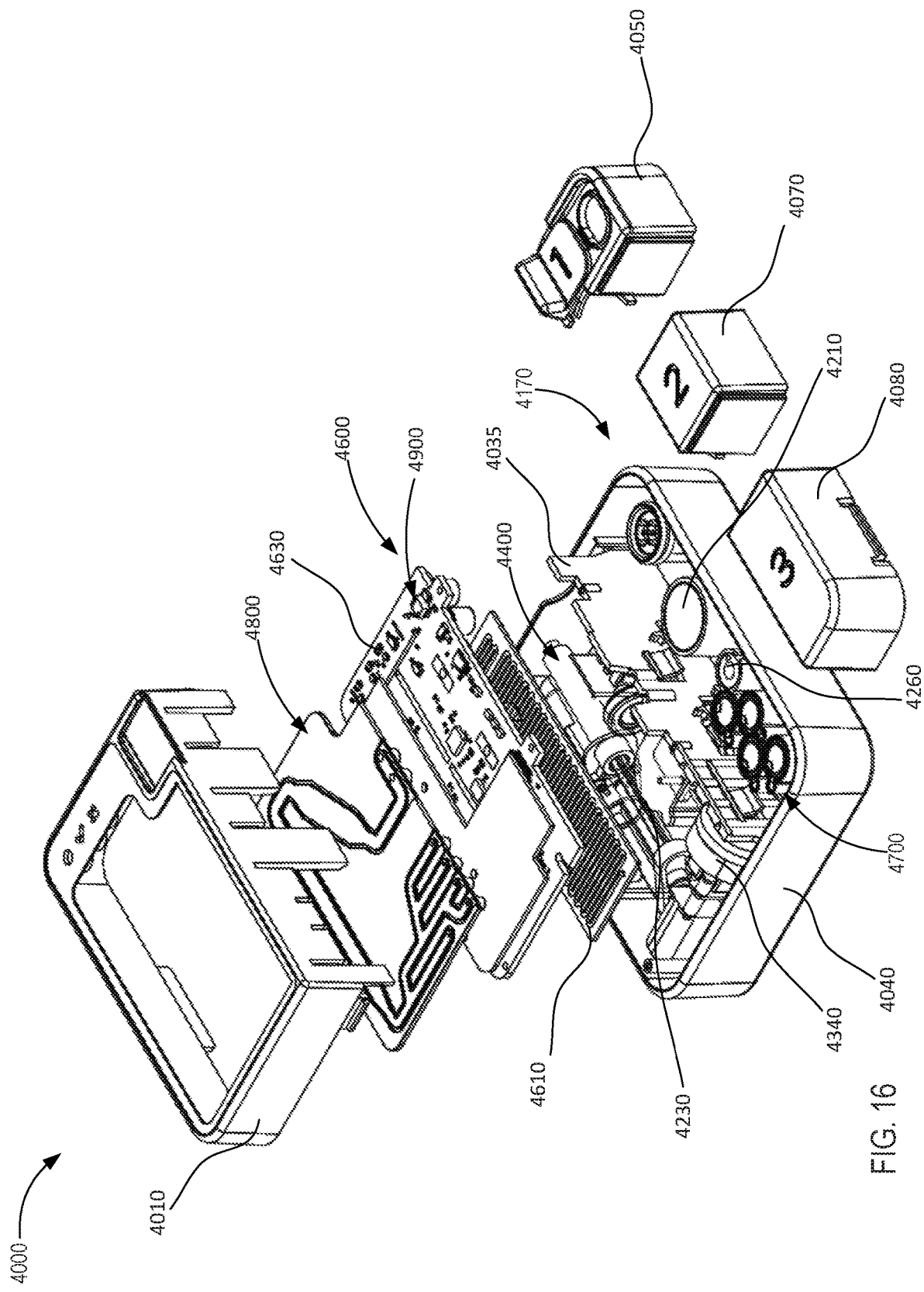
FIG. 16 is an exploded view of the molecular diagnostic test device shown in FIGS. 12 and 13.

The diagnostic test device 4000 includes a housing 4001 (including a top portion 4010 and a bottom portion 4040), within which the modules described herein are fully or partially contained. Similarly stated, the housing 4001 (including the top portion 4010 and/or the bottom portion 4040) at least partially surround and/or enclose the modules. As shown in FIGS. 11-13, the device 4000 includes a sample input module 4170, a sample preparation module 4200, an inactivation module 4300, a fluidic drive (or fluid transfer) module 4400, an amplification reagent module 4500 (see FIG. 11), an amplification module 4600, a detection module 4800, a reagent storage module 4700, a rotary venting valve 4340, and an electronic system 4900 (FIG. 16). In some embodiments, the sample preparation module 4200 can be considered as including the sample input module 4170 and/or the inactivation (also referred to as the lysing) module 4300, but in other embodiments, these modules can be considered as distinct from the sample preparation module 4200. In some embodiments, the sample preparation module 4200 can be considered as including the amplification reagent (or mixing) module 4500.

The housing assembly 4001 includes the top housing 4010, the bottom housing 4040, the vertical manifold 4035, and the sample transfer manifold 4100. As shown, the top housing 4010 includes a label 4020 that defines a series of detection openings (or windows) 4011 via which the device can be read. In some embodiments, the detection openings 4011 are aligned with the detection module 4800. In this manner, the signals produced by and/or on each detection surface of the detection module 4800 are visible through the appropriate detection opening 4011. In some embodiments, the top housing 4010 and/or the label 4020 is opaque (or semi-opaque), thereby "framing" or accentuating the detection openings. In some embodiments, for example, the top housing 4010 can include markings 4017 (e.g., thick lines, colors or the like) to highlight the detection opening 4011. In other embodiments, the detection openings 4011 are aligned with one or more light output devices (e.g., LEDs) that produce an electronic output to the user based on the signals produced by and/or within the detection module 4800. For example, in some embodiments, the electronic system 4900 can include a digital read module implemented in at least one of a memory or a processing device that determines the presence of a signal (e.g., colorimetric output) produced by the detection module 4800. For example, in some embodiments, the electronic system can include the structure and function of the electronic detection system 3950 described above. As shown, in some embodiments, the top housing 4010 can include indicia 4017 identifying the detection opening to a specific result (e.g., a control output, an indication of whether the target pathogen is present, and indications of whether the target pathogen is resistant to or susceptible to a drug or treatment regimen.

The top housing 4010 includes a lid portion to which the sample lid 4140 is movably coupled. The top housing 4010 includes a lock surface 4004 to which the lid 4140 engages to prevent downward motion of the lid 4140 and the sample input actuator 4050 when the lid 4140 is in the opened position. When the lid 4140 is in the opened position (FIGS. 12 and 13), the input opening 4052 (defined by the input actuator 4050 and/or the top housing 4010) is exposed, thereby allowing for the biological sample to be conveyed into the test device 4000.

Referring to FIG. 16, the housing assembly 4001 includes the vertical manifold 4035, which provides both structural support and defines flow paths for various fluids that are conveyed within the device 4000. In particular, the vertical manifold 4035 defines a series of reagent passages through which reagents are conveyed from the reagent module 4700 to the detection module 4800. Additionally, the vertical manifold 4035 defines on or more vent passages to allow venting to facilitate fluid movement throughout the device 4000. The housing assembly 4001 also includes the sample transfer manifold 4100, which provides both structural support and defines flow paths for various fluids that are conveyed within the device 4000. In particular, the sample transfer manifold 4100 includes a sample input portion 4102, a wash portion 4103, an elution portion 4104, and a reagent portion 4105.

The sample preparation module 4200 includes a sample input module 4170, a wash module 4210, an elution module 4260, a filter assembly 4230, and various fluidic conduits (e.g., tubes, lines, valves, etc.) connecting the various components. The device 4000 also includes the lysing module 4300 and the amplification reagent (or mixing) module 4500, which, together with the sample preparation module 4200, performs the nucleic acid extraction and preparation of an amplification solution according to any of the methods described herein. Thus, although the sample preparation module 4200, the sample input module 4170, the inactivation module 4300, and the amplification reagent module 4500 are described as separate modules, in other embodiments, the structure and function of the sample preparation module 4200 can be included within or performed by the inactivation module 4300, the amplification reagent module 4500, and/or the sample input module 4170, and vice-versa. Similarly stated, any of the sample input modules, sample preparation modules, inactivation modules and/or lysing modules described herein can include any of the structure and/or perform any of the functions of the other modules to perform any of the methods of sample preparation or nucleic acid extraction described herein. By eliminating the need for external sample preparation and a cumbersome instrument, the device 4000 is suitable for use within a point-of-care setting (e.g., doctor's office, pharmacy or the like) or at the user's home, and can receive any suitable biological sample S1. The biological sample S1 (and any of the input samples described herein) can be any of the types of samples described herein.

Figure 17:
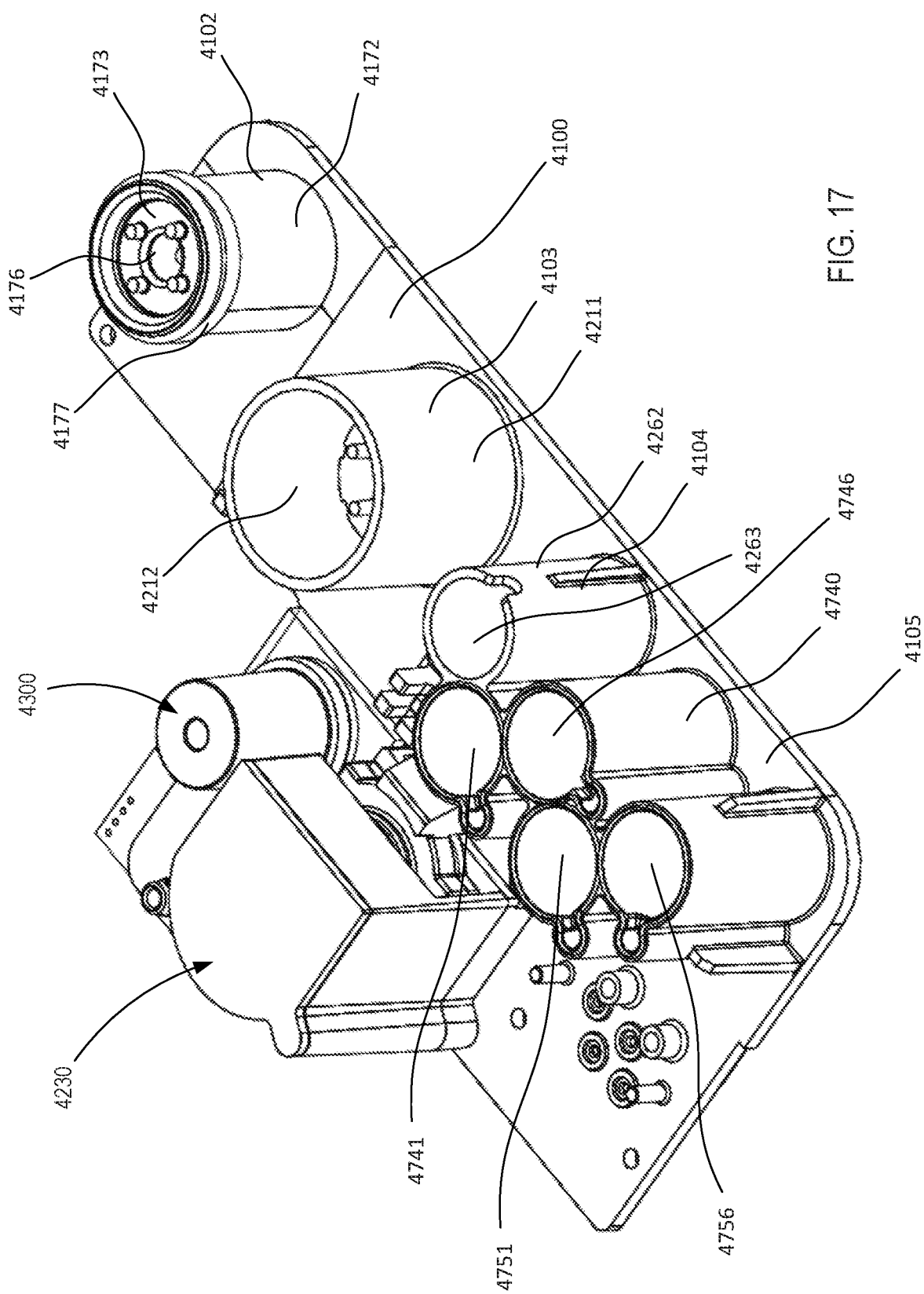
FIG. 17 is a perspective view of the molecular diagnostic test device shown in FIGS. 12 and 13, including an optional filter assembly and an inactivation assembly coupled thereto.

The sample input module 4170 is configured to receive a biological sample S1 containing a biological entity, and convey the biological sample toward the remaining elements of the sample preparation module 4200 (e.g., the filter assembly 4230). The sample input module 4170 includes the sample input portion 4102 of the sample transfer manifold 4100, the sample input (or first) actuator 4050, and the lid 4140. Referring to FIG. 17, the sample input portion 4102 of the sample transfer manifold 4100 includes a cylindrical housing 4172 and a cover. As shown, the top surface of the cylindrical housing 4172 (including the top surface 4173 and/or portions of the cover) and an inner surface of the first actuator 4050 define a sample input volume 4068, within which the biological sample is conveyed at the start of a test. The outer portion of the cylindrical housing 4172 includes one or more seals 4177 that slidingly engage the inner surface of the first actuator 4050 to form a fluid-tight seal. In some embodiments, the sample input volume 4068 or other portions of the sample input module 4170 can include a reagent (e.g., a positive control or other reagent as described herein).

The cylindrical housing 4172 defines a first (or vertical) fluid passage 4176 that is between (and fluid communication with) a sample input passage defined by the sample transfer manifold 4100 and that is in fluid communication with the wash module 4210 and the filter assembly 4230. In this manner, when the biological sample is compressed by the first actuator 4050 it is conveyed from the sample input volume 4068, through the first fluid passage and towards the filter assembly 4230.

The wash module 4210 is configured to convey a wash solution toward the remaining elements of the sample preparation module 4200 (e.g., the filter assembly 4230). In some embodiments, the wash module 4210 is configured such that it cannot be actuated out of the desired sequence of operations. Specifically, in some embodiments, the wash module 4210 is configured to be locked until after the biological sample has been conveyed to the sample preparation module 4200. The wash module 4210 includes the wash portion 4103 of the sample transfer manifold 4100, the wash (or second) actuator 4070, and a wash container. Referring to FIG. 17, the wash portion 4103 of the sample transfer manifold 4100 includes a cylindrical housing 4211 and a top surface (or cover) (not shown). The upper portion of the cylindrical housing 4211 defines a volume 4212 within which a wash container (not shown) is disposed. The wash container can be a sealed wash container that allows the sample wash solution to be stored for long periods of time (e.g., 6 months or longer). The wash solution within the wash container can be any suitable solution. The wash module 4210 is actuated by the wash (or second) actuator 4070.

As described herein, the biological sample and the wash solution are conveyed through the filter assembly 4230. The filter assembly is configured to receive an elution buffer (via a backflush operation) to convey the desired particles (and the elution buffer) to the lysing module 4300. After the filtering operation, the elution buffer and the captured particles flow out of the filter assembly 4230 and toward the lysing module 4300 via a sample outlet port.

The elution module (or assembly) 4260 of the sample preparation module 4200 is contained within the housing, and defines an elution volume within which an elution composition is stored. The elution composition can be any of the elution compositions described herein. In some embodiments, the elution composition can include proteinase K, which allows for the release of any bound cells and/or nucleic acid molecules (e.g., DNA) from the filter membrane. The output from the elution module 4260 can be selectively placed in fluid communication with the filter assembly 4230, when the filter assembly is toggled into a backflow configuration, as described above. Thus, the elution module 4260 can include any suitable flow control devices, such as check valves, duck-bill valves, or the like to prevent flow back towards and/or into the elution volume.

In some embodiments, the elution module 4260 is configured such that it cannot be actuated out of the desired sequence of operations. Specifically, in some embodiments, the elution module 4260 is configured to be locked until after the biological sample has been conveyed to the sample preparation module 4200 and the wash operation (described above) has occurred. The elution module 4260 includes the elution portion 4104 of the sample transfer manifold 4100, the reagent (or third) actuator 4080, and an elution plunger (not shown). Referring to FIG. 17, the elution portion 4104 of the sample transfer manifold 4100 includes a cylindrical housing 4262 that defines an elution volume 4263 within which the elution buffer (or composition) is contained. The elution module 4260 is actuated by the reagent (or third) actuator 4080.

The lysing module 4300 includes a chamber body and a heater. In use, the sample (e.g., the filtered sample) is conveyed into the chamber body and heated to a first temperature within a lysing temperature range to lyse certain constituents in the solution or de-activate the enzymes present in input fluid after lysis occurs. In some embodiments, the lysing module 4300 can be used in conjunction with RT-PCR and can heat or maintain the solution at a temperature to release a ribonucleic acid (RNA) molecule within the solution.

After the lysing and/or inactivation operations, the output from the lysing module 4300 can be conveyed into the mixing module (also referred to as the amplification reagent module) 4500, which mixes the output of inactivation module 4300 with the reagents to produce an amplification solution. In some embodiments, the amplification reagent module 4500 contains a primer set targeting a single nucleotide polymorphism (SNP) locus in a polynucleotide of the biological sample S1. The SNP primer set P can include any of the SNP primer sets shown and described herein. In some embodiments, the primer set P can also target a locus in a polynucleotide associated with a target pathogen (e.g., organism, bacteria). Thus, in some embodiments, the device (and methods using the device) can produce one amplicon through which the presence of the organism and whether the organism is resistant or susceptible to a treatment can be detected. In other embodiments, the device (and methods using the device) can produce two or more amplicons through which the presence of the organism and whether the organism is resistant or susceptible to a treatment can be detected. In some embodiments, the amplification reagent module 4500 is configured to reconstitute the reagent in a predetermined input volume, while ensuring even local concentrations of reagents in the entirety of the volume. In some embodiments, the mixing chamber module 4500 is configured to produce and/or convey a sufficient volume of liquid for the amplification module 4600 to provide sufficient volume output to the detection module 4800. The mixing module 4500 can be any suitable mixing module, such as those shown and described in International Patent Publication No. WO2016/109691, entitled "Devices and Methods for Molecular Diagnostic Testing," which is incorporated herein by reference in its entirety.

The fluidic drive (or transfer) module 4400 can be a pump or series of pumps configured to produce a pressure differential and/or flow of the solutions within the diagnostic test device 4000. Similarly stated, the fluid transfer module 4400 is configured to generate fluid pressure, fluid flow and/or otherwise convey the biological sample and the reagents through the various modules of the device 4000. The fluid transfer module 4400 is configured to contact and/or receive the sample flow therein. Thus, in some embodiments, the device 4000 is specifically configured for a single-use to eliminate the likelihood that contamination of the fluid transfer module 4400 and/or the sample preparation module 4200 will become contaminated from previous runs, thereby negatively impacting the accuracy of the results. The fluid transfer module 4500 can be any suitable fluid transfer module, such as those shown and described in International Patent Publication No. WO2016/109691, entitled "Devices and Methods for Molecular Diagnostic Testing," which is incorporated herein by reference in its entirety.

After being mixed within the amplification reagent module 4500, the prepared sample is then conveyed to the amplification module 4600 (as shown by the arrow EE in FIG. 11). The amplification module 4600 includes a flow member 4610 and a heater 4630. The flow member 4610 can be any suitable flow member that defines a volume or a series of volumes within which the that prepared solution can flow and/or be maintained to amplify the target nucleic acid molecules within the solution. The heater 4630 can be any suitable heater or group of heaters coupled to the flow member 4610 that can heat the prepared solution within the flow member 4610 to perform any of the amplification operations as described herein.

In some embodiments, the flow member 4610 defines a single volume within which the prepared solution is maintained and heated to amplify the nucleic acid molecules within the prepared solution. In other embodiments, the flow member 4610 can define a "switchback" or serpentine flow path through which the prepared solution flows. Similarly stated, the flow member 4610 defines a flow path that is curved such that the flow path intersects the heater 4630 at multiple locations. In this manner, the amplification module 4600 can perform a "flow through" amplification reaction where the prepared solution flows through multiple different temperature regions.

Although the amplification module 4600 is generally described as performing a thermal cycling operation on the prepared solution, in other embodiment, the amplification module 4600 can perform any suitable thermal reaction to amplify nucleic acids within the solution. In some embodiments, the amplification module 4600 (and any of the amplification modules described herein) can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process.

The detection methods enabled by the device 4000 include sequential delivery of the detection reagents and other substances within the device 4000. Further, the device 4000 is configured to be an "off-the-shelf" product for use in a point-of-care location (or other decentralized location), and is thus configured for long-term storage. Accordingly, the reagent storage module 4700 is configured for simple, non-empirical steps for the user to remove the reagents from their long-term storage containers, and for removing all the reagents from their storage containers using a single user action. In some embodiments, the reagent storage module 4700 and the rotary selection valve 4340 are configured for allowing the reagents to be used in the detection module 4800, one at a time, without user intervention.

Specifically, the device 4000 is configured such that the last step of the initial user operation (i.e., the depressing of the reagent actuator 4080) results in dispensing the stored reagents. This action crushes and/or opens the sealed reagent containers present in the assembly and relocates the liquid for delivery. The rotary venting selector valve 4340 allows the reagent module 4700 to be vented for this step, and thus allows for opening of the reagent containers, but closes the vents to the tanks once this process is concluded. Thus, the reagents remain in the reagent module 4700 until needed in the detection module 4800. When a desired reagent is needed, the rotary valve 4340 opens the appropriate vent path to the reagent module 4700, and the fluidic drive module 4400 applies vacuum to the output port of the reagent module 4700 (via the detection module 4800), thus conveying the reagents from the reagent module 4700. The reagent module 4700 and the valve 4340 can be similar to the reagent modules and valves shown and described in International Patent Publication No. WO2016/109691, entitled "Devices and Methods for Molecular Diagnostic Testing," which is incorporated herein by reference in its entirety.

The detection module 4800 is configured to receive output from the amplification module 4600 and reagents from the reagent module 4700 to produce one or more colorimetric changes to indicate presence or absence of target pathogen (e.g., bacteria, virus, or organism) in the initial input sample and whether the target pathogen is resistant to or susceptible to a treatment regimen (e.g., antibiotics). The detection module 4800 also produces one or more colorimetric signals to indicate the general correct operation of the test (positive control and negative control). In some embodiments, color change induced by the reaction is easy to read and binary, with no requirement to interpret shade or hue. In other embodiments, the electronic system 4900 of the device includes a digital read module implemented in at least one of a memory or a processing device that determines the presence the one or more colorimetric outputs produced by the detection module 4800. For example, in some embodiments, the electronic system 4900 can include at least one light source and at least one light detector and the digital detection module can perform an algorithm based on detected light attenuated by or reflecting from a detection surface to determine the presence of a color change on the detection surface. In some embodiments the electronic system 4900 can include any of the components and perform any of the features of the electronic system 1950, 2950 and 3950 described herein.

Figure 19:
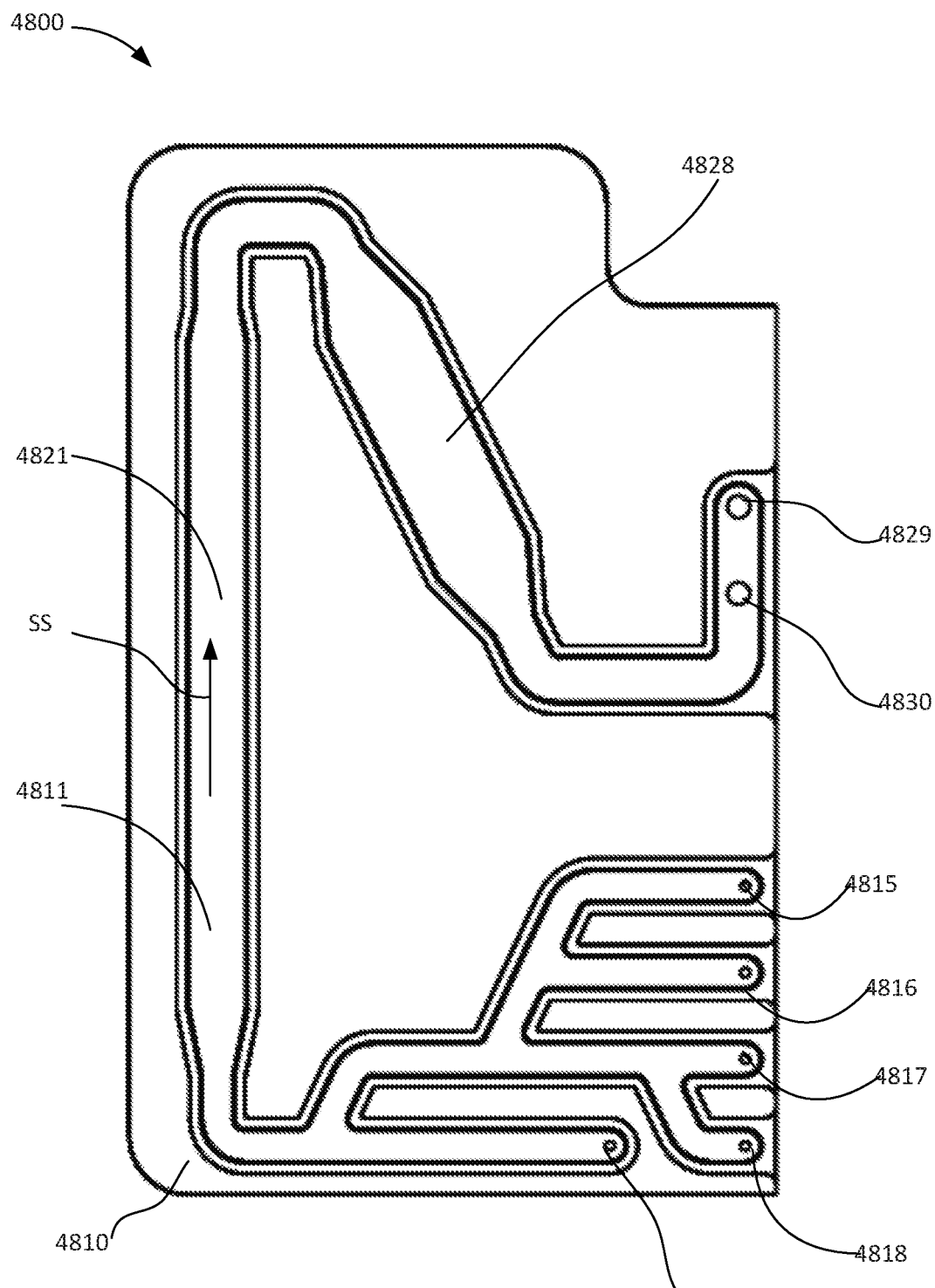
Figure 20:
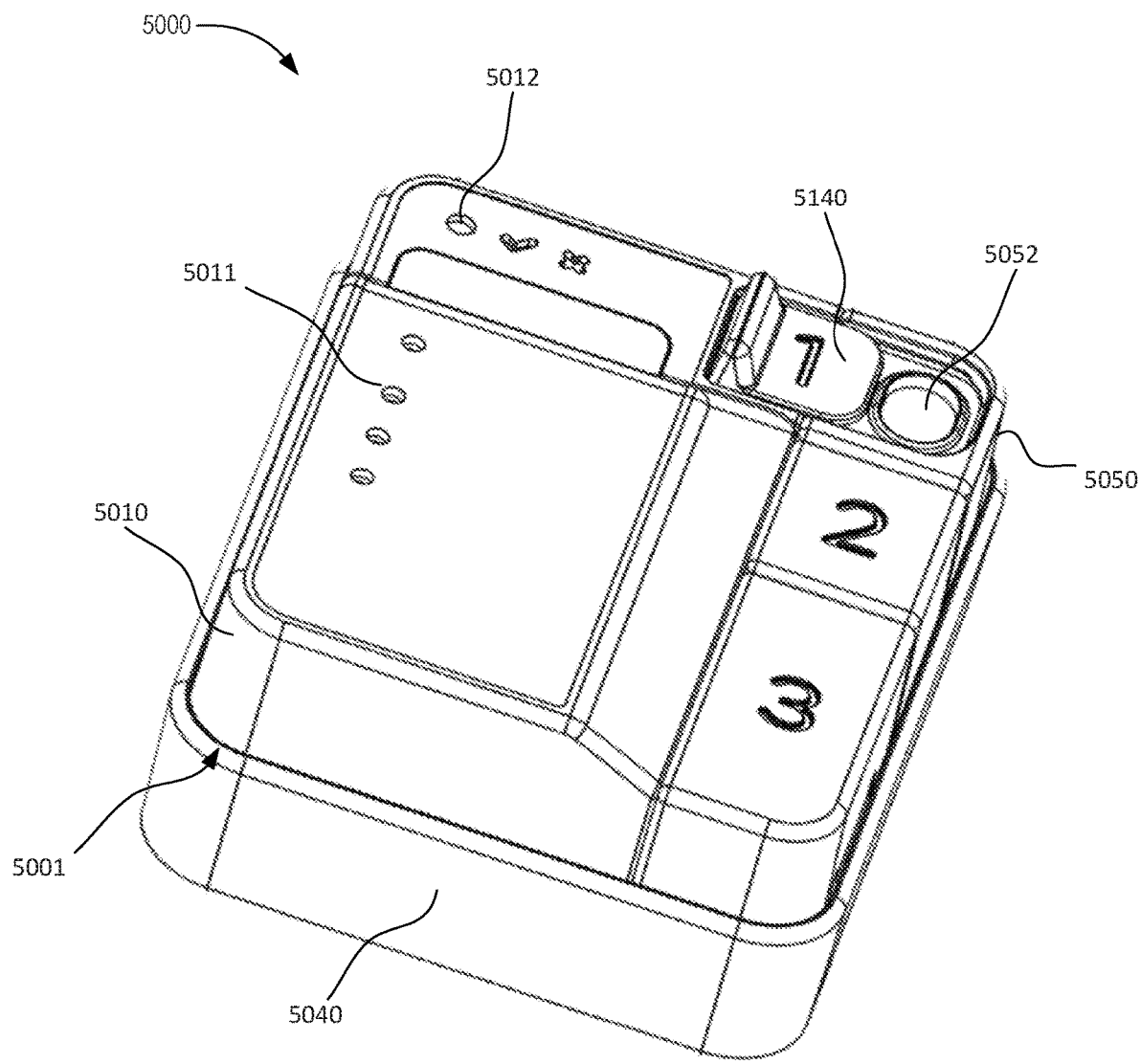
FIG. 20 is a perspective view of a molecular diagnostic test device with electronic detection capability, according to an embodiment.

Referring to FIGS. 18 and 19, the detection module includes a lid (not shown), a detection housing 4810 and a heater 4840. The heater 4840 can be similar to any of the circuit board heaters described herein and also shown and described in International Patent Publication No. WO2016/109691, entitled "Devices and Methods for Molecular Diagnostic Testing," which is incorporated herein by reference in its entirety. The lid and the detection housing 4810 form a flow cell for detection. The housing 4810 defines a detection chamber/channel 4812 having a sample inlet portion 4813, a reagent inlet portion, a detection portion 4821, and an outlet portion 4828. The sample inlet portion 4813 includes the sample inlet port 4814, which is fluidically coupled to the outlet of the amplification module 4600 and receives the amplified sample. The reagent inlet portion includes a first reagent inlet port 4815, a second reagent inlet port 4816, a third reagent inlet port 4817, and a fourth reagent inlet port 4818. The first reagent inlet port 4815 is coupled to the reagent module 4700 via the vertical manifold 4035. Thus, in use a first reagent (e.g., a detection reagent, such as the first reagent R1 described above with reference to the detection module 2800) can be conveyed into the detection channel 4812 via the first reagent inlet port 4815. The second reagent inlet port 4816 is coupled to the reagent module 4700 via the vertical manifold 4035. Thus, in use a second reagent (e.g., a wash solution) can be conveyed into the detection channel 4812 via the second reagent inlet port 4816. The third reagent inlet port 4817 is coupled to the reagent module 4700 via the vertical manifold 4035. Thus, in use a third reagent (e.g., a detection reagent, such as the second reagent R2 described above with reference to the detection module 2800) can be conveyed into the detection channel 4812 via the third reagent inlet port 4817. The fourth reagent inlet port 4818 is coupled to the reagent module 4700 via the vertical manifold 4035. Thus, in use a fourth reagent (e.g., a second flow of a detection reagent, such as the second reagent R2 described above with reference to the detection module 2800) can be conveyed into the detection channel 4812 via the first reagent inlet port 4818.

The detection channel 4812 includes an entrance portion 4811, a detection portion 4821, and outlet portion 4828. The detection portion (or "read lane") 4821 is defined, at least in part by, and/or includes a series of detection surfaces. The detection surfaces 4821 include a series of capture probes to which the target amplicon(s) produced during amplification can be bound when the detection solution flows across the detection surface 4821. For example, the capture probes may include one or more allele-specific probes, one or more capture probe that bind the target amplicon outside the SNP locus, and/or one or more capture probes that bind an second target amplicon for the same organism. In some embodiments, the detection surfaces 4821 are configured for multiplex detection and/or drug-sensitivity determination using multiple SNP loci and/or multiple target organisms. The capture probes can be any suitable probes formulated to capture or bind to the target amplicon, such as those described above with respect to the detection module 1800 or any other probes described herein.

Although the device 4000 is described as including a filter assembly 4230, in some embodiments, a sample preparation device need not include a filter or filter assembly. For example, in some embodiments, the sample input may be directly linked to a lysing/inactivation chamber, similar to the lysing chamber 4300 as shown above. Advantages of a device without a filter assembly include lower pressures in the device, no risk of breaking a filter, fewer parts, fewer reagents required, higher recovery of target organisms from the clinical sample matrix and higher recovery of DNA from target organisms. In such embodiments, a device differs from the device 4000 in that the sample is flowed from the input module 4170 directly to the lysing module 4300. In some embodiments, the sample may be lysed by heating without need for a specialized lysis buffer or lysis enzymes. Any proteases or nucleases released from the cells of the sample will be inactivated by heating. For example, a sample may be flowed into the lysing module and held until the module reaches a set temperature (for example greater than 90 C) and then flowed through an inactivation segment. In the inactivation segment, the sample is rapidly heated to 95 C causing the cells in the sample to lyse and proteins from within the cells to be inactivated.

The device 4000 can be used to perform any of the methods described herein. To use the device, a biological sample is first placed into the sample input volume 4068, as described above. The lid 4140 is then moved to it closed position, thereby sealing the sample input volume 4068. After the lid 4140 is closed, the first actuator 4050 can be manipulated to actuate the sample input module 4170. Movement of the first actuator 4050 compresses the sample input volume 4068 and pushes the sample to the filter assembly 4230. The second actuator 4070 can then be depressed. This causes the wash solution to be conveyed into the filter assembly 4230, as described above. The third actuator 4080 can then be depressed to actuate the filter assembly 4230 and also causes the elution solution to be conveyed into the filter assembly 4230, as described above. The movement of the third actuator 4080 also releases the reagents from the reagent canisters. In some embodiments, the device 4000 can be used to detect the presence of a target organism and whether the target organism is susceptible to a treatment regimen or resistant to the treatment regimen.

FIGS. 20-24 are various views of a molecular diagnostic test device 5000 that includes an electronic control system 5900 and an electronic detection system 5950, according to an embodiment. The test device 5000 is an integrated device (i.e., the modules are contained within a single housing) that is suitable for use within a point-of-care setting (e.g., doctor's office, pharmacy or the like) or a decentralized test facility In some embodiments, the device 5000 is suitable for use as an over-the-counter (OTC) diagnostic solution. Similarly stated, in some embodiments, the device 5000 (and the methods performed with the device) are suitable for use by an untrained user (i.e., a lay user), can be supplied without a prescription, and can be performed independent of a health care facility (e.g., at the user's home). In some embodiments, the device 5000 can have a size, shape and/or weight such that the device 5000 can be carried, held, used and/or manipulated in a user's hands (i.e., it can be a "handheld" device). In other embodiments, the test device 5000 can be a self-contained, single-use device. In some embodiments, the test device 5000 can be configured with lock-outs or other mechanisms to prevent re-use or attempts to re-use the device.

Further, in some embodiments, the device 5000 can be a CLIA-waived device and/or can operate in accordance with methods that are CLIA waived. Similarly stated, in some embodiments, the device 5000 (and any of the other devices shown and described herein) is configured to be operated in a sufficiently simple manner, and can produce results with sufficient accuracy to pose a limited likelihood of misuse and/or to pose a limited risk of harm if used improperly. In some embodiments, the device 5000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 5000 can be configured for long term storage in a manner that poses a limited likelihood of misuse (spoilage of the reagent(s), expiration of the reagents(s), leakage of the reagent(s), or the like). In some embodiments, the molecular diagnostic test device 5000 is configured to be stored for up to about 36 months, up to about 32 months, up to about 26 months, up to about 24 months, up to about 20 months, up to about 58 months, or any values therebetween.

The test device 5000 is configured to manipulate a biological sample to produce one or more output signals associated with one or more target polynucleotide sequences (e.g., an amplicon to detect the presence of a target organism, an amplicon associated with a target SNP), and can be used to perform any of the molecular diagnostic methods described herein. The test device 5000 and certain components therein are similar in structure and function to those described for the test device 4000, therefore a detailed description of certain modules (e.g., the sample preparation module, the lysing or RT-PCR module, the reagent module, the amplification module, and the fluidic drive module) is not provided herein. Rather, the following description focuses on the electronic control system 5900 and the electronic detection system 5950.

As shown, the diagnostic test device 5000 includes a housing 5001 (including a top portion 5010 and a bottom portion 5040), within which the modules described herein are fully or partially contained. The device 5000 includes any of the modules described with reference to the device 4000 or the device 6000. For example, the device can include a sample input module, a sample preparation module, a RT-PCR module, a fluidic drive (or fluid transfer) module, an amplification reagent module, an amplification module, a reagent storage module, and a rotary venting valve as described herein. In other embodiments, the test device 5000 need not include all of these modules. For example, in some embodiments, the test device 5000 can be devoid of a sample preparation module that includes filtering capabilities (as shown for the sample preparation module 4200). The test device 5000 also includes a detection module 5800, an electronic control system 5900, and an electronic detection system 5950.

As shown, the top housing 5010 includes a portion or label that defines a set of detection openings (or windows) 5011 and a set of status light openings 5012. The detection openings (or windows) 5011 are aligned with the output LEDs 5956 (only one of the four output LEDs is identified in FIG. 22) of the electronic detection system 5950. In this manner, the output signals produced by the output LEDs 5956 are visible through the appropriate detection opening 5011. Such light outputs can indicate whether a target polynucleotide sequence is present in the biological sample, whether a reference polynucleotide sequence is present in the biological sample, or a combination of various results. The determination of whether the target polynucleotide sequence is present is made by a digital read module of the electronic detection system 5950, as described herein. The status light openings 5012 are aligned with one or more status light output devices (e.g., LEDs) 5954 of the electronic control module 5900 (see FIG. 21). In this manner, a light output produced by such status lights is visible through the status light openings 5012. Such light outputs can indicate, for example, whether the device 5000 is receiving power from the power source, whether an error has occurred (e.g., an error associated with insufficient sample volume or the like), and whether the test has been successfully completed. In some embodiments, the status lights can produce an output (e.g., various colors, flashing patterns, or the like) that provide an indication of the test result.

The top housing 5010 includes a lid portion to which the sample lid 5140 is movably coupled. The top housing 5010 includes a lock surface to which the lid 5140 engages to prevent downward motion of the lid 5140 and the sample input actuator 5050 when the lid 5140 is in the opened position. When the lid 5140 is in the opened position (FIGS. 20 and 21), the input opening 5052 (defined by the input actuator 5050 and/or the top housing 5010) is exposed, thereby allowing for the biological sample to be conveyed into the test device 5000.

The detection module 5800 is configured to receive output from an amplification module (similar to the amplification module 4600 described above) and reagents from a reagent module (similar to the reagent module 4700 described above) to produce one or more colorimetric changes to indicate presence or absence of target polynucleotide sequence (e.g., bacteria, virus, or organism) in the initial input sample, whether the target pathogen is resistant to or susceptible to a treatment regimen (e.g., antibiotics), and/or other characteristics of the target pathogen. The detection module 5800 also produces one or more colorimetric signals to indicate the general correct operation of the test (positive control and negative control). As described, the electronic detection system 5950 of the device includes a digital read module implemented in at least one of a memory or a processing device that determines the presence the one or more colorimetric outputs produced by the detection module 5800.

Figure 22:
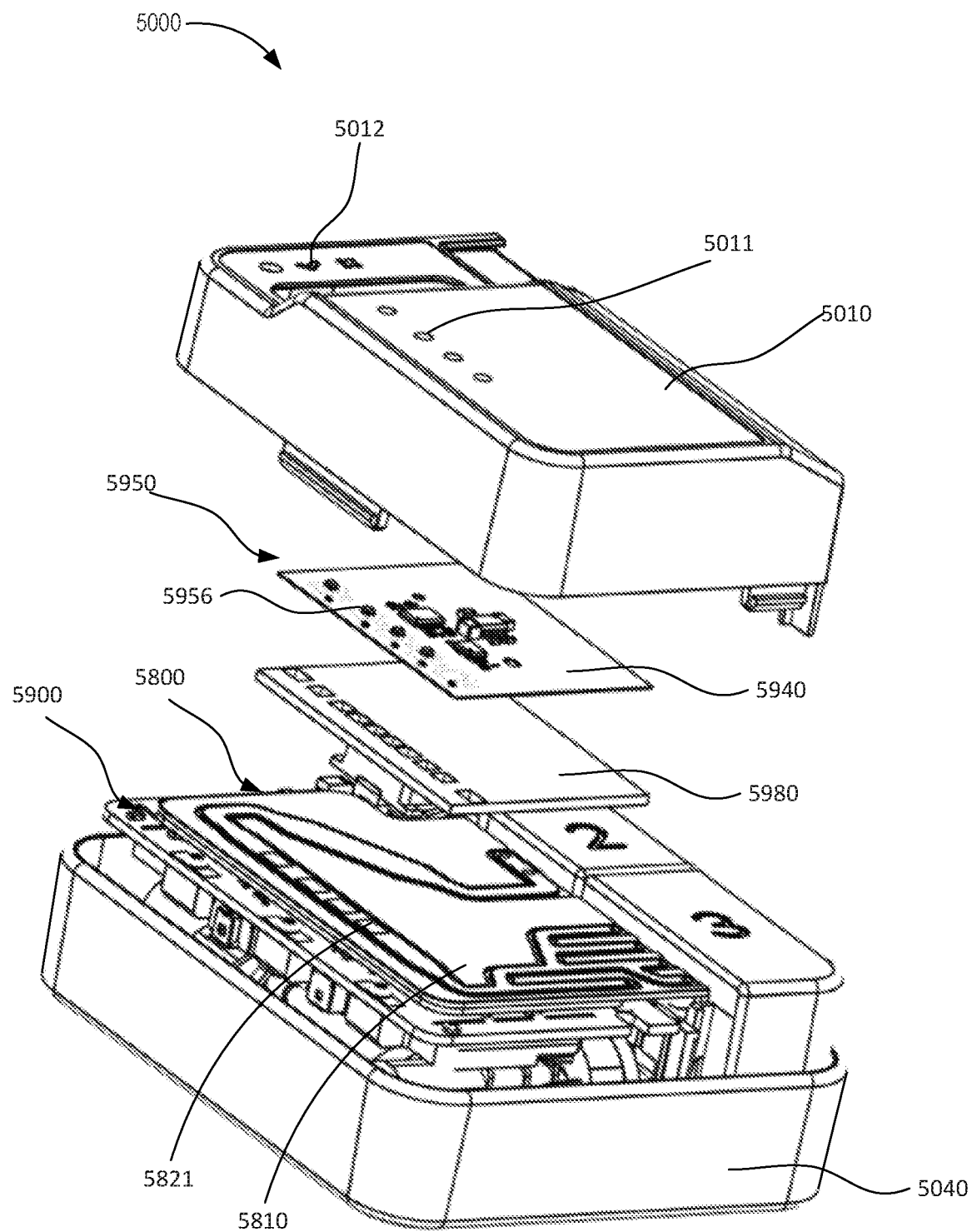
FIGS. 22 and 23 are exploded views of the molecular diagnostic test device shown in FIG. 20 from a top perspective (FIG. 22) and a bottom perspective (FIG. 23).
Figure 24:
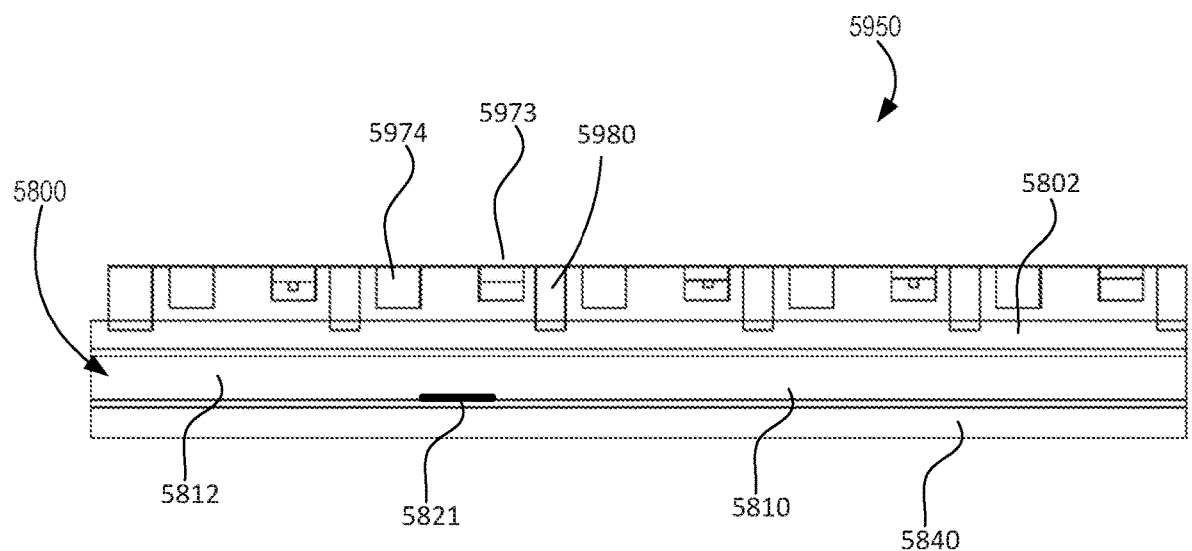
FIG. 24 is a cross-sectional view of a portion of the molecular diagnostic test device shown in FIG. 20 taken along line X-X in FIG. 21.

Referring to FIGS. 22 and 24, the detection module 5800 includes a lid 5802, a detection housing 5810 and a heater 5840. The heater 5840 can be similar to any of the circuit board heaters described herein and also shown and described in International Patent Publication No. WO2016/109691, entitled "Devices and Methods for Molecular Diagnostic Testing," which is incorporated herein by reference in its entirety. The lid 5802 and the detection housing 5810 form a flow cell for detection. Thus, the detection module 5800 defines a detection chamber/channel 5812 having a sample inlet portion, a reagent inlet portion, a detection portion, and an outlet portion. Similar to the detection module 4800 described above, the sample inlet portion is fluidically coupled to the outlet of the amplification module and receives the amplified sample. The reagent inlet portion is fluidically coupled to the reagent module to allow the desired detection reagents to be conveyed into the detection channel 5812 and reacted with biologic sample (or portions thereof that are resident in the detection module). The biological sample and the reagents can be reacted within a detection channel 5812 in any suitable manner to produce the desired signal (e.g. the reaction described above with reference to FIG. 6). For example, in some embodiments, the biological sample can be introduced at a first time such that only portions (e.g., a biotinylated amplicon) of the biological sample remain within the detection module. The reagents can be introduced at a second time and can react with the remaining portion of the biological sample to produce the colorimetric signals described herein. Thus, the biological sample and the reagent can be combined within a detection volume without the entirety of each component residing within the detection module at the same time. Moreover, in some embodiments, undesired portions of the biological sample can be washed from the detection module before the reagent is introduced into the detection module.

The detection channel 5812 includes a series of detection surfaces. The detection surfaces 5821 include a series of capture probes to which the target amplicon(s) produced during amplification can be bound when the biological sample (that has been processed via amplification) flows within the detection channel and across the detection surface 5821. For example, the capture probes may include one or more allele-specific probes, one or more capture probe that bind the target amplicon outside the SNP locus, and/or one or more capture probes that bind an second target amplicon for the same organism. In some embodiments, the detection surfaces 5821 are configured for multiplex detection and/or drug-sensitivity determination using multiple SNP loci and/or multiple target organisms. The capture probes can be any suitable probes formulated to capture or bind to the target amplicon, such as those described above with respect to the detection module 2800 or any other probes described herein.

Figure 21:
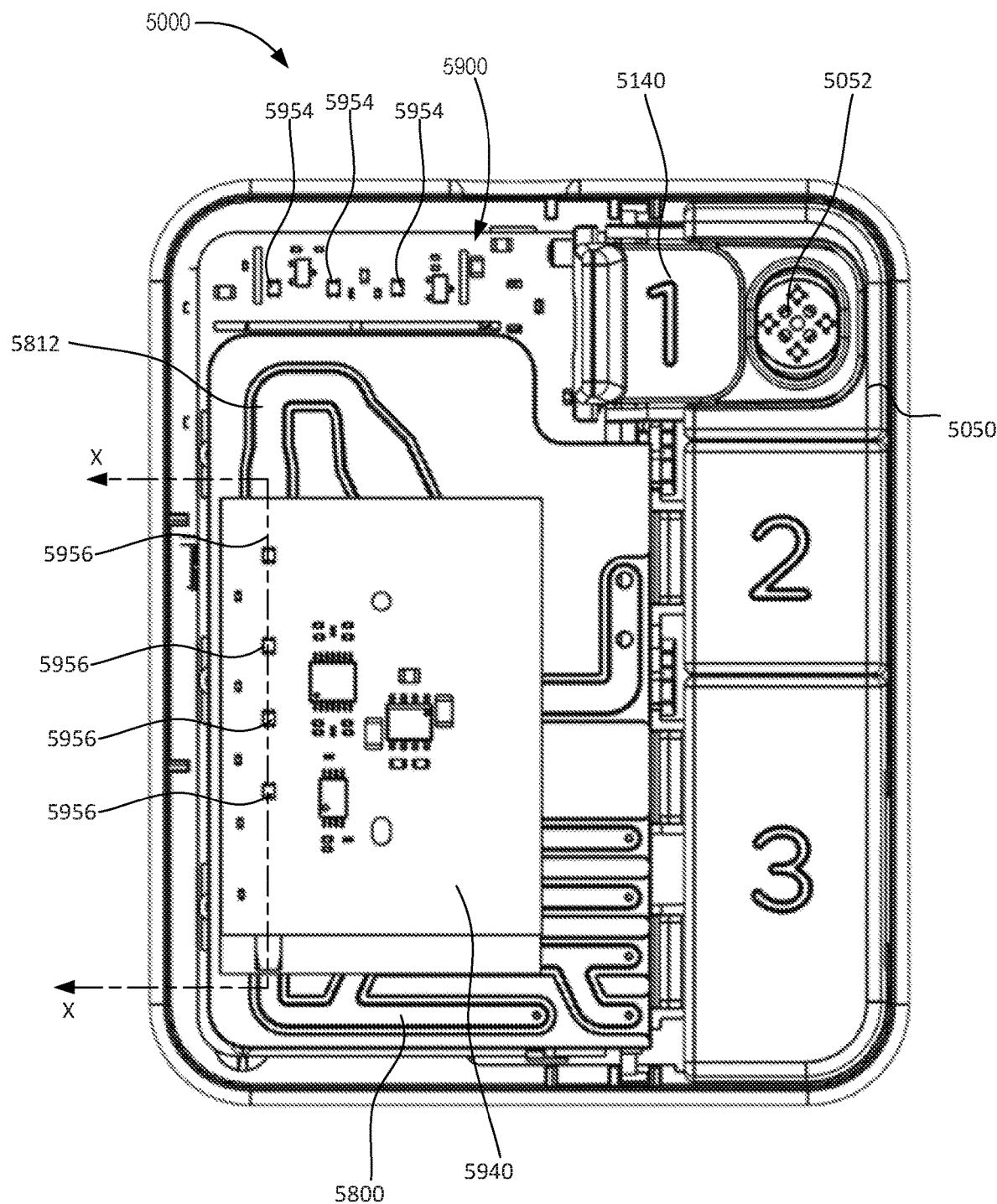
FIG. 21 is a top view of the molecular diagnostic test device shown in FIG. 20 with the top portion of the housing removed to show the internal components.

The electronic control system 5900 is coupled to and/or within a housing of the molecular diagnostic test device 4000, and includes one or more printed circuit boards, processors, and/or subsystems. Referring to FIG. 21, the electronic control system 5900 includes a printed circuit board heater 5630 that functions as a heater for the amplification module, that houses the components (e.g., processor(s), memory components, etc.) to control the overall operation of the device 5000. The electronic control system 5900 can include the components of the electronic system 3900 described herein, such as, for example, a flow control module, a heater control module, and a feedback module. Similar to the electronic system 3900 described herein, the electronic control system 5900 also includes at least one processor 3951, at least one memory 3952, one or more sensors (collectively identified as 3970), portions of an input/output subsystem (e.g., status output LEDs 5954).

The electronic control system 5900 also includes or is operatively coupled to the electronic detection system 5950. The electronic detection system 5950 includes a printed circuit board 5940 and a series of light-emitting diodes (LEDs) 5973 (collectively referred to as a light assembly) and photodiodes 5974 (collectively referred to as a photodetector assembly; only one pair of LEDs and photodiodes is identified). The printed circuit board 3940 can include a processor, a memory, and/or any other electrical components necessary for the detection module 5800 and the electronic detection system 5950 (or portions thereof) to operate as desired. For example, the electrical components can be resistors, capacitors, inductors, switches, microcontrollers, microprocessors and/or the like. The electronic detection system 5950 can include all of the structure (including software modules) and perform all of the functions shown and described above with reference to the electronic detection system 3950. Thus, the electronic control system 5950 can include a communication module (similar to the communication module 3961) and a digital read module (similar to the digital read module 3960).

Figure 23:
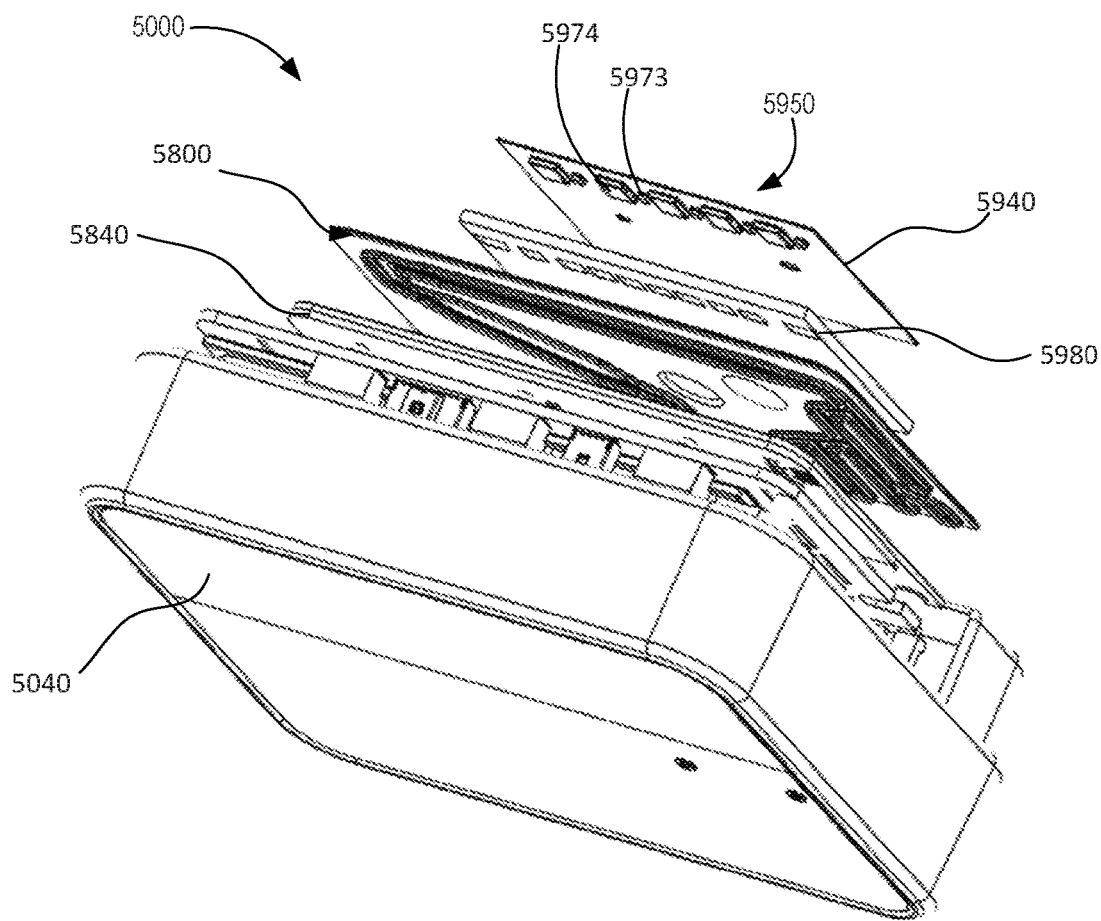

As shown in FIGS. 23 and 24, the LEDs 5973 and photodiodes 5974 are arranged on one side of the flow cell 5810, with one pair corresponding to each of the detection surfaces 5821. In this manner, when the LED is actuated, it will produce a light beam that is reflected from a reflective member (not shown, but that can be similar to the reflective member 3975) and back through the flow cell 5810 and detection surface 5821. The heater 5840 is coupled to the opposite side of the flow cell 5810. By positioning the LEDs and photodiodes in the manner (e.g., with a photodiode directly under each detection surface), the heater 5840 can be close-coupled to the detection surfaces to facilitate efficient heat transfer. Moreover, substantially all light detected by the photodiode will be from the light beam that passes through the detection surface 5821. In this manner, when the target nucleic acid is present, it will bind to the probe (as described above). Addition of the reagent, which can be a precipitating substrate formulated to produce an insoluble colored particle when the reagent is contacted with a catalyzing agent, then produces a colored "spot" on the detection surface. As the reaction proceeds, the light beam from the LED will be attenuated as it passes through the spot, thereby yielding a reduced light signal (not shown) detected by the photodiode 5974. Accordingly, by monitoring the signal from the photodiode 5974, the digital read module can determine when a color spot has sufficiently formed to produce a positive result. As described herein, the sensor signals from the photodiodes 5974 can be manipulated by the digital read module to determine a magnitude (e.g., average value, slope, average variability) over a time period. The digital read module can also compare the magnitude of a light signal from a first detection surface with that of a second detection surface to determine whether the color spot on the first detection surface has formed sufficiently to indicate the presence of the target polynucleotide sequence.

As shown in FIGS. 22-24, the detection module 5800 also includes a light shield 5980 to reduce light other than that emitted by the desired LED 5973 from reaching the desired photodiode 5974. The light shield 5980 surrounds a detection envelope associated with each of the detection surfaces 5821 between the top side of the flow cell 5810 and the photodiode/LED pair. The light shield 5980 can be a flexible material, such as a foam material to seal between the top of the flow cell 5810 and the printed circuit board 5940, thereby minimizing undesired light transfer into the detection envelope. In other embodiments, device 5000 can include a similar light shield that surrounds the status LEDs 5954 to reduce the likelihood that light from the status lights will impact the signals read by the photodiodes 5974. In yet other embodiments, the flow cell 5810 includes a light-blocking portion on one or more of its edges (e.g., the sides that are nonparallel to the heater 5840 and the top lid 5802.

In some embodiments, the electronic detection system 5950 actuates (or applies power to) only one LED at a time. In this manner, light from an adjacent LED will not affect the photodiode signal associated with a particular detection surface 5821. Specifically, the electronic detection system 5950 can multiplex the readings by continuously cycling through each pair of photodiodes and LEDs. The cycling frequency can be any suitable value, and can be selected to accurately assess the rate of formation of the color spot. In some embodiments, the bandwidth of an amplification circuit (used to amplify the signal from the photodiodes) can limit the reaction time of the signal to the applied light from the LED. Accordingly, the duration during which the LED remains powered (i.e., emitting light) must be sufficiently long to ensure an accurate reading.

In some embodiments, the LEDs 5973 and photodiodes 5974 (or any of the LEDs and photodetectors described herein) can be tuned to maximize the response of the photodiode to formation of the colorimetric signal (i.e., the assay signal). Similarly stated, in some embodiments, the LEDs 5973 (and any of the LEDs herein) can have an emitted light wavelength, and/or the photodiodes 5974 (and any of the photodetectors herein) can have a spectral sensitivity that is associated with the precipitating substrate that produces the color molecules through which the light passes. For example, in some embodiments, the substrate can be a precipitating substrate formulated to catalyze the production of the colorimetric signal by producing an insoluble colored product when contact with a first reagent. Such precipitating substrates can include, for example, TMB (3,3',5,5' tetramethylbenzidine), DAB (3,3' diaminobenzidine), or 4 CN (4-chloro-1-napthol) based membrane substrates for horseradish peroxidase enzymes, or BCIP (5-bromo-4-chloro-3-indolyl-phosphate) based membrane substrates for alkaline phosphatase. In some embodiments, the precipitating substrate can be the BioFX® TMB HRP Membrane Substrates produced by Surmodics. In some embodiments, such precipitating substrates can produce a dark color (e.g., dark purple), which can be matched with (and can produce significant attenuation of) the incident light produced by the LEDs 5973.

In some embodiments, the use of such precipitating substrates can produce a maximum attenuation of light intensity for emitted wavelengths between 520 nm and 580 nm. Accordingly, in some embodiments, the LEDs 5973 can have a peak wavelength of 570 nm. Moreover, in some embodiments, the spectral sensitivity of the photodiode 5974 can be maximized around 570 nm to correspond to the primary wavelength of light emitted from the LED 5973. In this manner, the electrical response of the photodiode 5974 can be maximized based on the selected substrate and LED performance. In other embodiments, the LEDs 5973 can have any suitable peak wavelength and the spectral sensitivity of the photodiodes can be maximized at any suitable wavelength.

Because the formation of the colorimetric signal on the detection surface 5821 occurs over several seconds, the signal produced by the photodiode 5974 will change as a function of time (e.g., the first time period and/or the second time period, as described herein). Further, because the change occurs over several seconds, the photodiodes 5974 need not have a fast response time. Accordingly, in some embodiments, the photodiodes 5974 are operated in photovoltaic mode. In this configuration, the photodiode 5974 produces a voltage (i.e., a sensor signal) in response to the applied light (e.g., the light signal that originates from the LED 5973). In some embodiments, the voltage signal can be amplified by any suitable amplification circuit. Because of the large time constant associated with the formation of the colorimetric signal, higher filtering can be included.

Figure 25:
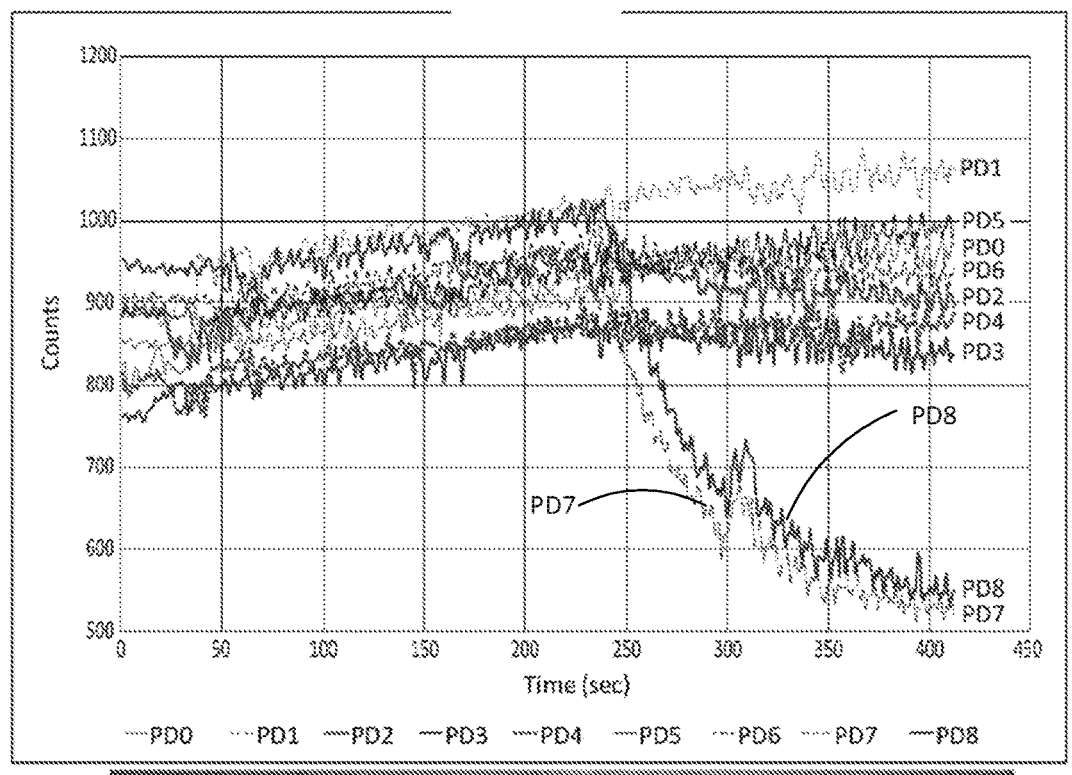
FIG. 25 is a plot showing a series of light signals (each corresponding to a detection surface) produced by an electronic system of a molecular diagnostic test device, according to an embodiment.

The device 5000 can be used to perform any of the methods described herein. Specifically, the digital read module of the electronic detection system 5950 is configured to receive a signal (e.g., from one or more photodiodes 2974) and determine, based on the signal, whether a color signal from the corresponding detection surface is present. Functions of the digital read module are described with respect to the plots shown in FIGS. 25 and 26 and the flow chart shown in FIG. 27. FIG. 25 is a plot showing a series of light signals (each corresponding to a detection surface 5821) produced by an electronic system (e.g., the electronic detection system 5950) of a molecular diagnostic test device (e.g., the device 5000) as a function of time. Specifically, FIG. 25 shows nine different light signals (in units of raw voltage counts), each corresponding to a different photodetector adjacent a detection surface (identified as photodetectors PD0 through PD8). As described herein, when the reagent (e.g., the substrate) is introduced into the detection module, a colorimetric signal (referred to as a "color spot") will form on those detection surfaces to which the target amplicon(s) have been bound by the capture probe. FIG. 25 shows a very strong color signal on the detection surfaces associated with photodetectors PD7 and PD8. Because the light beam (see the light beam LB in FIG. 7) is attenuated by the strong color, the light signals for PD7 and PD8 drop significantly as the color is formed. Because the colorimetric signals take time to form on the detection surface, the reduction in the light signal is not instantaneous, but occurs over time after the introduction of the reagent (which occurs at about a time of 250 seconds).

The presence of a color signal from other detection surfaces, however, is not as readily apparent. For example, the detection surfaces associated with photodetectors PD2, PD3, PD4, and PD6 appear to show some level of color, possibly indicating the presence of the target amplicon(s). Such low levels of color could be the result of a low concentration of the polynucleotide. The digital read module can employ any suitable algorithm to accurately and repeatably detect the presence of a colorimetric signal from the detection surfaces as described herein. In some embodiments, the digital read module can subtract a background measurement taken through a "background" portion of the detection module 5800 where no colorimetric signal is formed (or expected). The digital read module can then receive a light signal associated with a detection surface over a period of time (i.e., after the introduction of the reagent) and produce an output indicating the presence of a color signal if the value of the light signal drops below a predetermined threshold.

Figure 26:
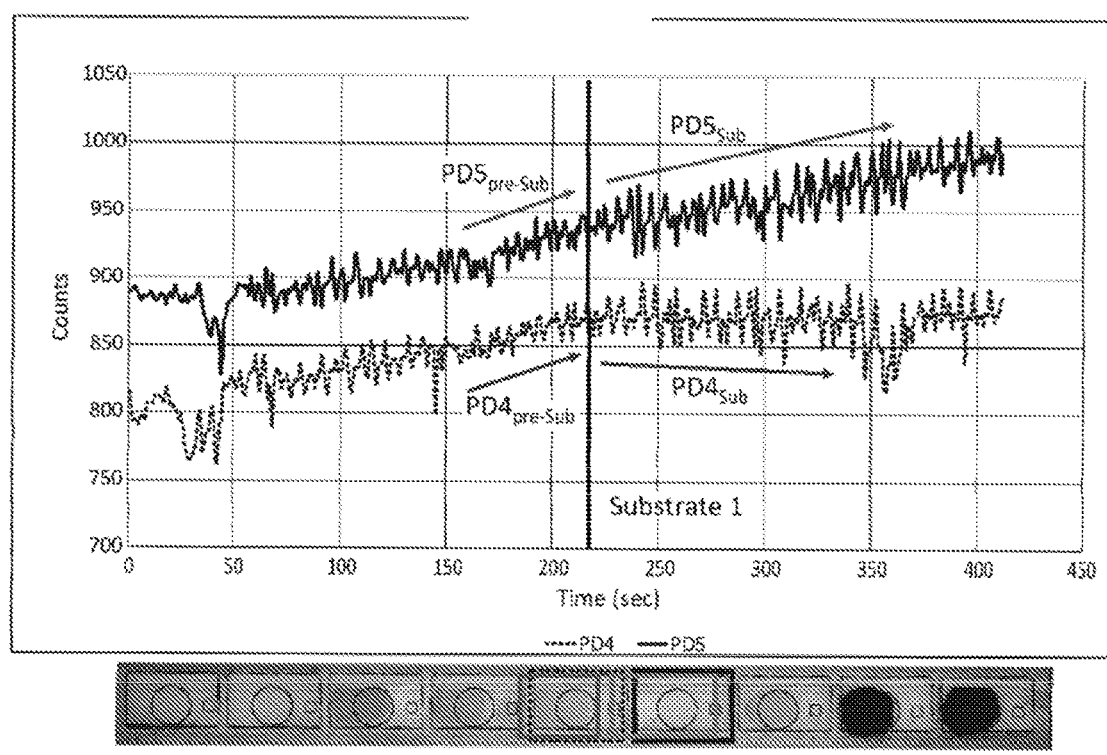
FIG. 26 is a plot showing two of light signals (each corresponding to a detection surface) to illustrate a detection algorithm according to an embodiment.

In other embodiments, the digital read module can determine the presence of a color signal based on the slope (or rate of change) of the light signal from the photodetector. As described above, because the intensity of the measured light beam is a function of the environmental and operational conditions (e.g. the temperature of the LED 5973 and/or the photodiode 5974), in the absence of any color, the magnitude of the light signal is not constant. Specifically, as shown in FIGS. 25 and 26, because device 5000 is generally cooling down during the detection operation (due to the completion of the amplification heating), the light signals generally increase as a function of time. In some embodiments, the digital read module first determines a baseline slope of the light signal during the time period before the substrate is introduced into the flow cell. This is shown in FIG. 26 as the slopes identified as PD$4_{pre-sub}$ and PD$5_{pre-sub}$. Because device 5000 is cooling, the slope during this time period is generally positive (reflecting an increase in the light signal). The digital read module then determines a slope of each light signal during the time period after the substrate is introduced into the flow cell. This is shown in FIG. 26 as the slopes identified as PD$4_{sub}$ and PD$5_{sub}$. If there is little attenuation (as shown for PD5), the light signal will continue to increase, and the slope PD$5_{sub}$ will remain positive. If, however, a color spot begins to form on the detection surface (as shown for PD4), the slope will decrease, and often become negative (as shown by the slope PD$4_{sub}$). The digital read module can produce an output indicating the presence of a color signal if the value of the slope of the light signal drops below a predetermined threshold. In other embodiments, the digital read module can produce an output indicating the presence of a color signal if the value of the slope of the light signal decreases by more than a threshold amount. For example, in some embodiments, the digital read module can produce an output indicating the presence of a color signal if the difference between the slope of the light signal during the second time period (i.e. after conveying the substrate) and the slope of the light signal during the first time period (i.e. before conveying the substrate) exceeds a threshold value.

Figure 27:
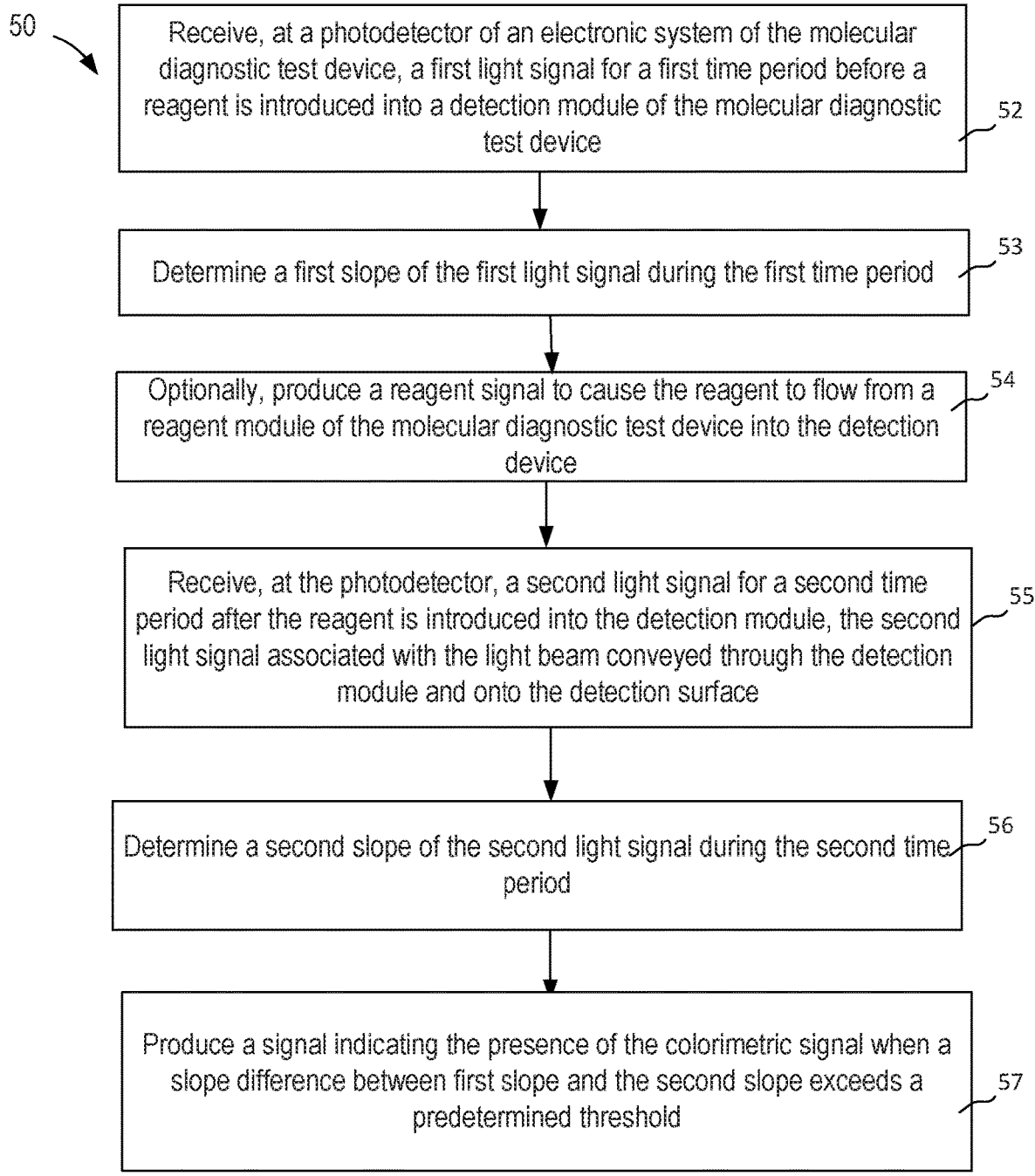
FIG. 27 is a flow chart of a method for detecting the presence of a colorimetric signal, according to an embodiment.

FIG. 27 is a flow chart of a computer-related method 50 of detecting a target organism and whether the target organism is susceptible to a treatment regimen or resistant to the treatment regimen using a molecular diagnostic test device, according to an embodiment. The method 50 is described in connection with the molecular diagnostic test device 5000 (also referred to as a "test device" or "device"). Although shown and described as being performed with the test device 5000, the method 50 and any of the methods described herein can be performed on any suitable molecular diagnostic device, such as any of the diagnostic devices shown and described herein or in International Patent Publication No. WO2016/109691, entitled "Devices and Methods for Molecular Diagnostic Testing," International Patent Publication No. WO2017/185067, entitled "Printed Circuit Board Heater for an Amplification Module," International Patent Publication No. WO2018/005870, entitled "Devices and Methods for Detection of Molecules Using a Flow Cell," International Patent Application No. PCT/US17/40112, entitled "Devices and Methods for Nucleic Acid Extraction," and International Patent Publication No. WO2019/060117, entitled "Portable Molecular Diagnostic Test Device and Methods for the Detection of Target Viruses," each of which is incorporated herein by reference in its entirety.

The method 50 includes receiving, at a photodetector of an electronic system of the molecular diagnostic test device, a first light signal for a first time period before a reagent is introduced into a detection module of the molecular diagnostic test device, at 52. The molecular diagnostic device can be the device 5000 and the electronic system can be the electronic system 5950, which includes the digital read module. A first slope (i.e., rate of change) of the first light signal during the first time period is determined, at 53. The determining the first slope can be performed by the digital read module. The digital read module and/or the electronic detection system 5950 can perform any suitable digital filtering, data smoothing, or other processes to manipulate the light signal (e.g., similar to the light signals shown in FIGS. 25 and 26) to determine the first slope.

In some embodiments, the electronic system 5900 can also control operations of the device, such as the heating (for amplification), the flow module (to move the biological sample and/or reagents within the device), and the detection operation. For example, in some embodiments, the method 50 optionally includes producing a reagent signal to cause the reagent to flow from a reagent module of the molecular diagnostic test device into the detection device, at 54. The reagent signal can be, for example, a signal to a valve (e.g., the valve 4340) and/or the fluidic drive module (e.g., the fluidic drive module 4400) to cause a detection reagent to be conveyed from the reagent storage module (e.g., the reagent storage module 4700) into the detection module.

The method 50 further includes receiving, at the photodetector, a second light signal for a second time period after the reagent is introduced into the detection module, at 55. The second light signal associated with the light beam conveyed through the detection module and onto the detection surface. A second slope (i.e., rate of change) of the second light signal during the second time period is determined, at 56. The determining the second slope can be performed by the digital read module. A signal indicating the presence of the colorimetric signal is produced when a slope difference between first slope and the second slope exceeds a predetermined threshold, at 57.

In addition to accurately determining the presence of a color signal from each of the detection surfaces, in some embodiments, the digital read module evaluates the signal(s) produced by each of the series of detection surfaces to produce a "yes/no" decision for whether the target organism (e.g., NG) is present and whether it is susceptible to a treatment regimen (e.g., NG that is susceptible to ciprofloxacin). In this manner, the digital read module can eliminate user subjectivity from interpreting test results, which can potentially produce errors when the detection surfaces produce a low color output. (i.e., a lightly-colored signal, such as the signal identified as $PD_4$ in FIG. 26).

Figure 28:
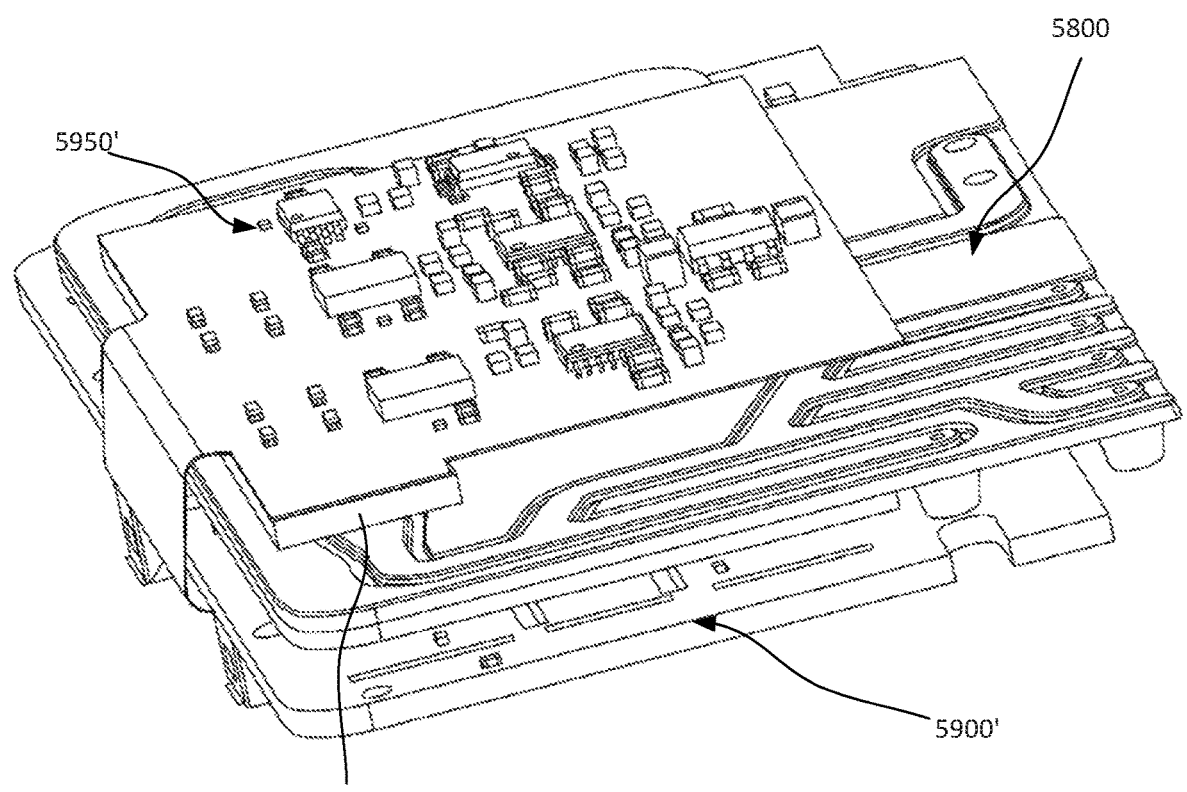
FIGS. 28 and 29 are a perspective view (FIG. 28) and an exploded view (FIG. 29) of a detection module and an electronic system of a molecular diagnostic test device, according to an embodiment.
Figure 29:
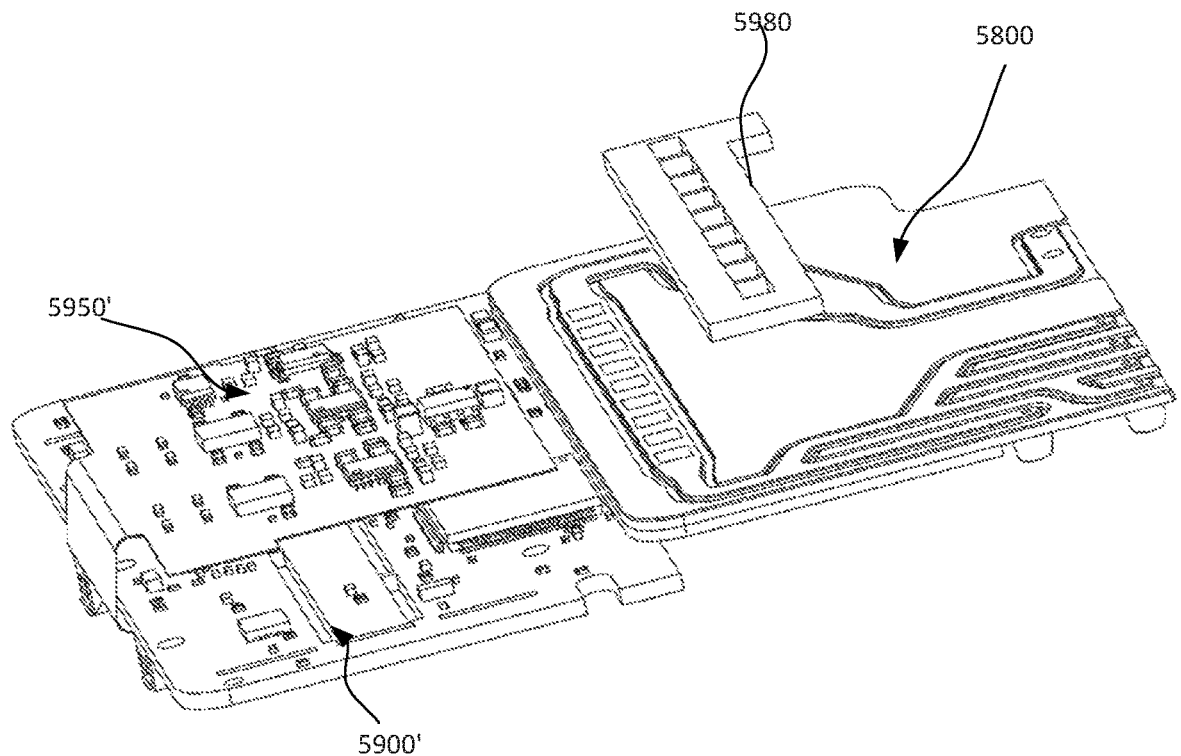

Although the electronic detection system 5950 is shown as including a circuit board 5940 that is operably coupled to, but separate from the circuit board of the electronic control system 5900, in other embodiments, a device can include an electronic detection system that is coupled to and/or shares a common printed circuit board with the electronic control system. In some embodiments, a device can include a circuit board system that wraps around a portion of the amplification module and detection module. For example, FIGS. 28 and 29 are perspective views of an electronic control system 5900' and an electronic detection system 5950' according to an embodiment. The electronic control system 5900' and the electronic detection system 5950' can be included in any of the devices described herein, including the device 5000, described above. The electronic control system 5900' and the electronic detection system 5950' are similar to the electronic control system 5900 and the electronic detection system 5950 described above, but the circuit boards for the two systems are joined on one side, as shown.

Figure 30:
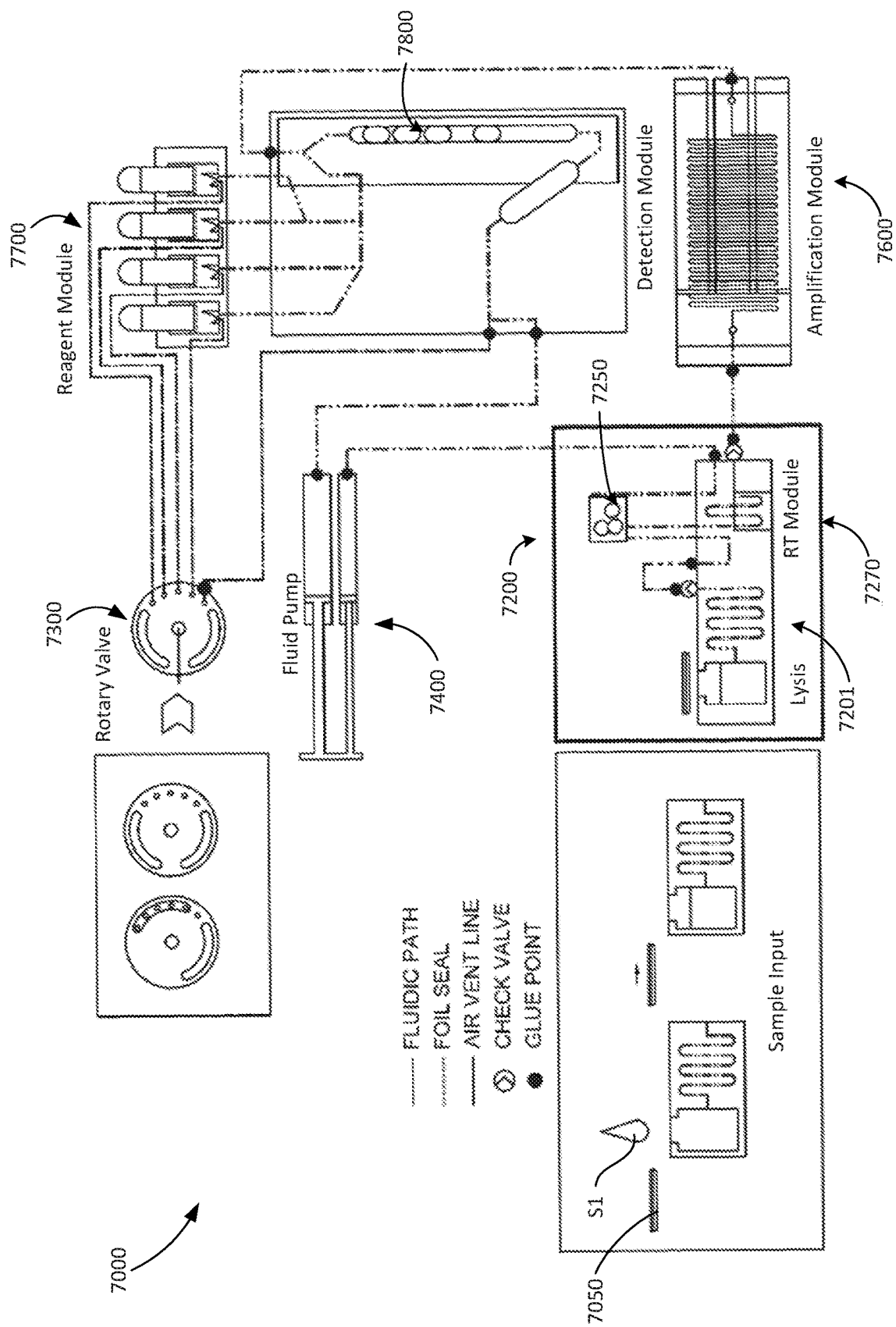
FIG. 30 is a schematic illustration of a molecular diagnostic test device, according to an embodiment.
Figure 31:
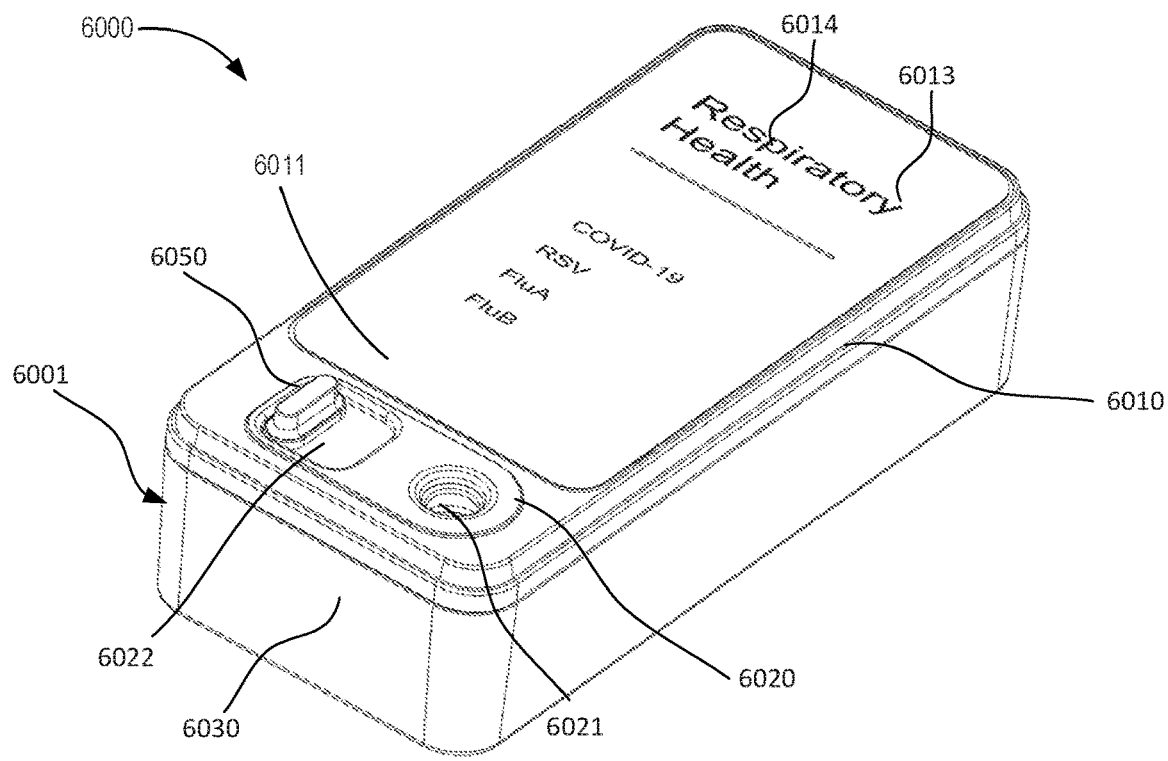
FIGS. 31 and 32 are a perspective view and a top view, respectively, of a molecular diagnostic test device, according to an embodiment.
Figure 32:
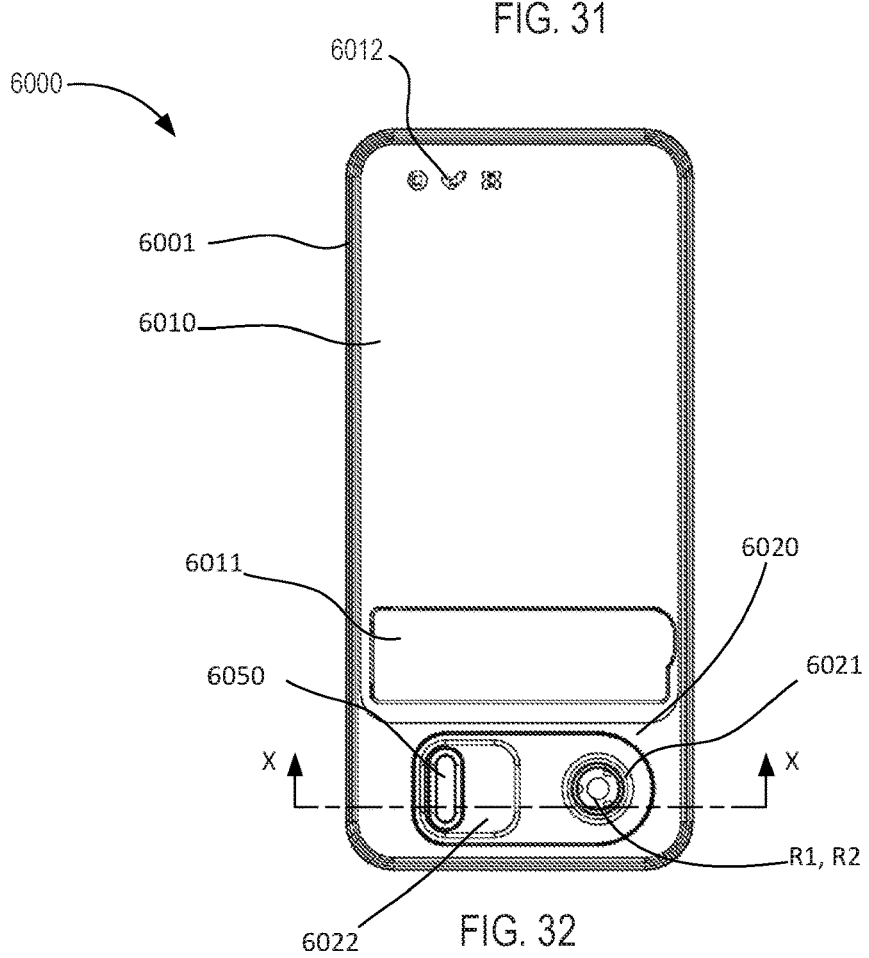

In some embodiments, a method includes lysing a raw sample and performing a reverse transcription polymerase chain reaction (PCR) on the lysed sample to facilitate detection of target RNA, for example to detect a target virus. To facilitate such methods, in some embodiments, a device can include a reverse transcription module to facilitate such methods of isolating and detecting viruses. As one example, FIG. 30 is a schematic illustration of a molecular diagnostic test device 7000 (also referred to as a "test device" or "device") that includes a reverse transcription module 7270, according to an embodiment. The schematic illustration describes the primary components of the test device 7000. Although the schematic illustration of FIG. 30 does not show an electronic detection system, it is understood that any of the electronic detection systems described herein can be included in the device 7000.

The test device 7000 is an integrated device (i.e., the modules are contained within a single housing) that is suitable for use within a point-of-care setting (e.g., doctor's office, pharmacy or the like) or a decentralized test facility. In some embodiments, the device 7000 is suitable for use as an over-the-counter (OTC) diagnostic solution. Similarly stated, in some embodiments, the device 6000 (and methods performed using the device) are suitable for use by an untrained user (i.e., a lay user), can be supplied without a prescription, and can be performed independent of a health care facility (e.g., at the user's home). In some embodiments, the device 7000 can have a size, shape and/or weight such that the device 7000 can be carried, held, used and/or manipulated in a user's hands (i.e., it can be a "handheld" device). A handheld device may have dimensions less than 15 cm×15 cm×15 cm, or less than 15 cm×15 cm×10 cm, or less than 12 cm×12 cm×6 cm. In other embodiments, the test device 7000 can be a self-contained, single-use device. Similarly stated, the test device 7000 is a stand-alone device that includes all necessary substances, mechanisms, and subassemblies to perform any of the molecular diagnostic tests described herein. As such, the device 7000 does not require any external instrument to manipulate the biological samples, and only requires a connection to a power source (e.g., a connection to an A/C power source, coupling to a battery, or the like) to complete the methods described herein. In some embodiments, the test device 7000 can be configured with lock-outs or other mechanisms to prevent re-use or attempts to re-use the device.

Further, in some embodiments, the device 7000 can be a CLIA-waived device and/or can operate in accordance with methods that are CLIA waived. Similarly stated, in some embodiments, the device 7000 (and any of the other devices shown and described herein) is configured to be operated in a sufficiently simple manner, and can produce results with sufficient accuracy to pose a limited likelihood of misuse and/or to pose a limited risk of harm if used improperly. In some embodiments, the device 7000 (and any of the other devices shown and described herein), can be operated by a user with minimal (or no) scientific training, in accordance with methods that require little judgment of the user, and/or in which certain operational steps are easily and/or automatically controlled. In some embodiments, the molecular diagnostic test device 7000 can be configured for long term storage in a manner that poses a limited likelihood of misuse (spoilage of the reagent(s), expiration of the reagents(s), leakage of the reagent(s), or the like). In some embodiments, the molecular diagnostic test device 7000 is configured to be stored for up to about 36 months, up to about 32 months, up to about 26 months, up to about 24 months, up to about 20 months, up to about 78 months, or any values there between.

The test device 7000 is configured to manipulate a biological sample S1 to produce one or more output signals associated with a target cell. Specifically, the device 7000 includes an actuator 7050, a sample preparation (or staging) module 7200, a fluidic drive (or fluid transfer) module 7400, a mixing module 7250, an amplification module 7600, a detection module 7800, a reagent module 7700, a valve 7300, and a power and control module (not shown). The test device and certain components therein can be similar to many of the components of the device 6000 shown and described with reference to FIGS. 31-34. Accordingly, the actuator 7050, the fluidic drive (or fluid transfer) module 7400, the mixing module 7250, the amplification module 7600, the detection module 7800, the reagent module 7700, and the valve 7300 are not described in detail herein. Moreover, the device including a reverse transcription module is similar the reverse transcription devices shown and described in International Patent Publication No. WO2018/005870, entitled "Devices and Methods for Nucleic Acid Extraction," each of which is incorporated herein by reference in its entirety.

The device 7000 includes a sample preparation module 7200 having a lysing chamber 7201 and a reverse transcription module 7270. The lysing chamber 7201 can be similar to the lysing chambers shown and described in International Patent Publication No. WO2018/005710, entitled "Devices and Methods for Detection of Molecules Using a Flow Cell," which is incorporated herein by reference in its entirety. Specifically, the lysing module 7300 includes a chamber body and a heater. In use, the sample (either a filtered sample or the raw biological sample S1) is conveyed into the chamber body and can be heated to a first temperature within a lysing temperature range to release a ribonucleic acid (RNA) molecule. The heater can convey thermal energy into the lysing module 7300 to produce a lysing temperature zone within any desired portion of the lysing module 7300 and for any of the time periods described herein. Accordingly, the lysing module can lyse the cells within the biological sample and also lyse the target virus that may be resident within the cells to produce the RNA suitable for a reverse transcription process.

Upon completion of the lysing, the lysed sample can then be mixed with a reverse transcriptase to form a reverse transcription solution. The mixing can be performed in any suitable portion of the device, such as, for example, in the flow paths between the lysing module 7201 and the reverse transcription module 7270. Alternatively, in some embodiments, the mixing of the lysed sample with the reverse transcriptase can occur within the mixing module 7250.

The reverse transcription module 7270 is integrated within the device and includes a flow member and a heater. The flow member defines a reverse transcription flow path through which the lysed sample containing the RNA can be conveyed. The reverse transcription module 7270 is configured to heat the reverse transcription solution to a second temperature within a reverse transcription temperature range to produce a complementary deoxyribonucleic acid (cDNA) molecule. In some embodiments, the reverse transcription module 7270 is configured to heat the reverse transcription solution to a third temperature above an inactivation temperature to cause inactivation of the reverse transcriptase. The reverse transcription solution can then be conveyed to the mixing module 7250 and mixed with the PCR reagents. After mixing, the solution can then be conveyed to the amplification module 7600 and amplified in a manner described herein.

Although the device 7000 is shown and described as including a reverse transcription module 7270, in other embodiments, a device and molecular diagnostic methods need not include a reverse transcription module.

FIGS. 31-34 show a test device 6000 that is an integrated device (i.e., the modules are contained within a single housing) that is suitable for use within a point-of-care setting (e.g., doctor's office, pharmacy or the like), decentralized test facility, or at the user's home. In some embodiments, the device 6000 can have a size, shape and/or weight such that the device 6000 can be carried, held, used and/or manipulated in a user's hands (i.e., it can be a "handheld" device). In other embodiments, the test device 6000 can be a self-contained, single-use device. Similarly stated, the test device 6000 is a stand-alone device that includes all necessary substances, mechanisms, and subassemblies to perform any of the molecular diagnostic tests described herein. As such, the device 6000 does not require any external instrument to manipulate the biological samples, and only requires a connection to a power source (e.g., a connection to an A/C power source, coupling to a battery, or the like) to complete the methods described herein. In some embodiments, the test device 6000 can be configured with lock-outs or other mechanisms to prevent re-use or attempts to re-use the device.

The test device 6000 is configured to manipulate a biological sample S1 to produce one or more output signals associated with a target cell. Specifically, the device 6000 includes a sample preparation module 6200, a fluidic drive (or fluid transfer) module 6400, an amplification module 6600, a detection module 6800, a reagent module 6700, a valve 6300, and a control module (not shown). The test device and certain components therein can be similar to any of the molecular test devices shown and described herein or in International Patent Publication No. WO2016/109691, entitled "Devices and Methods for Molecular Diagnostic Testing," which is incorporated herein by reference in its entirety. Accordingly, a detailed description of certain modules (e.g., the fluidic drive module 6400) is not provided herein. A description of each of the modules is provided below.

Figure 33:
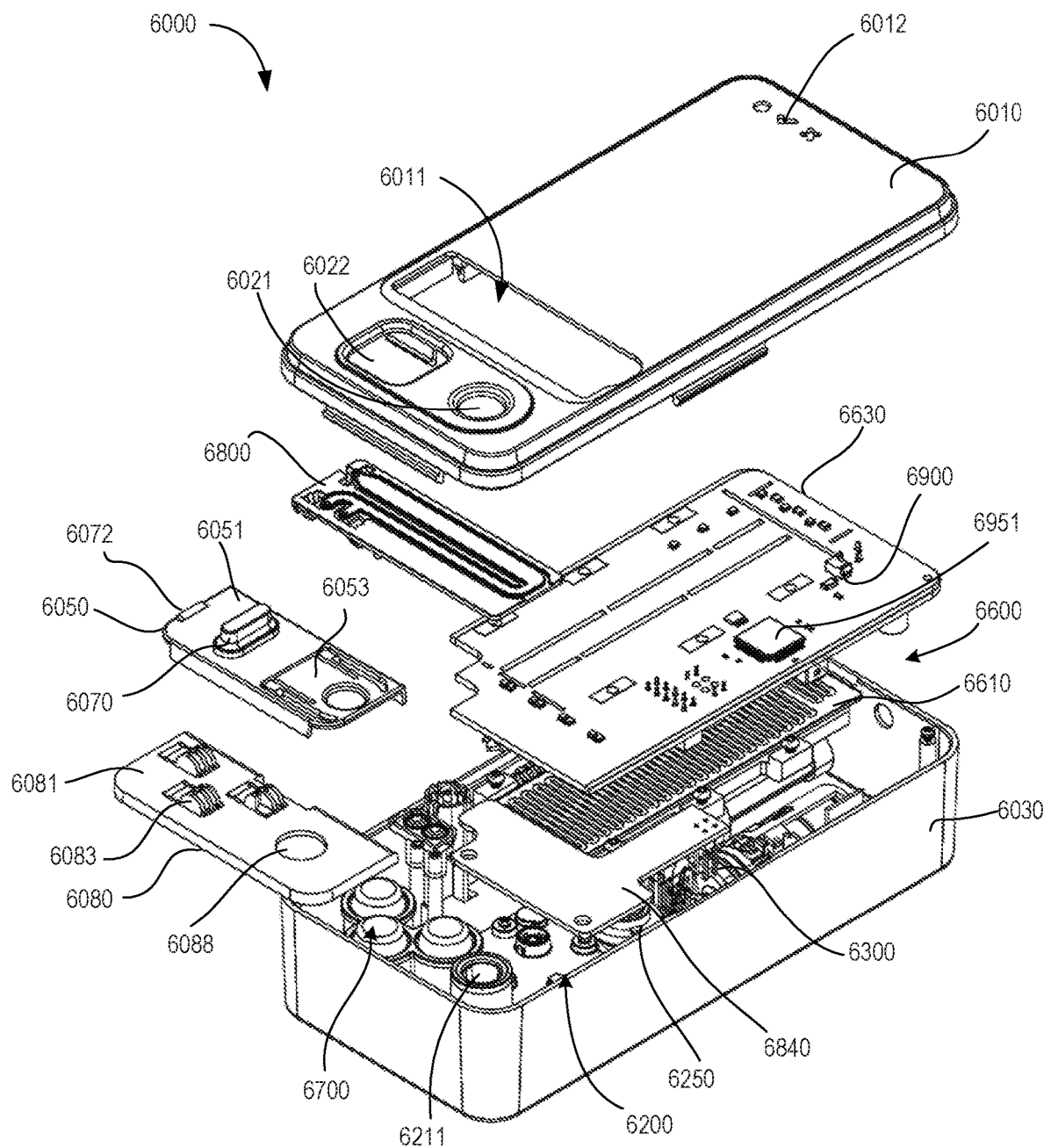
FIG. 33 is an exploded view of the molecular diagnostic test device shown in FIGS. 31 and 32.

The test device 6000 is configured to manipulate an input sample to produce one or more output signals associated with a target cell, according to any of the methods described herein. The diagnostic test device 6000 includes a housing 6001 (including a top portion 6010 and a bottom portion 6030), within which the modules described herein are fully or partially contained. Similarly stated, the housing 6001 (including the top portion 6010 and/or the bottom portion 6030) at least partially surround and/or enclose the modules. FIG. 33 shows the sample preparation module 6200, the fluidic drive (or fluid transfer) module 6400, the amplification module 6600, the detection module 6800, the reagent module 6700, the fluid transfer valve 6300, and the electronic control module 6950 situated within the housing 6001.

The housing assembly 6001 includes a top housing 6010, a bottom housing 6030, and a lid 6050 (which functions as a cover and an actuator). As shown, the top housing 6010 defines a detection opening (or window) 6011 and a series of status light openings 6012. The top housing 6010 also includes a sample input portion 6020 and a label 6013. The detection opening (or window) 6011 is aligned with output LEDs, touch screen or other visual output device (not shown) of the electronic detection system. In this manner, the output signals produced by the visual output device are visible through the detection opening 6011. Such visual outputs can indicate whether a target polynucleotide sequence is present in the biological sample, whether a reference polynucleotide sequence is present in the biological sample, or a combination of various results. The determination of whether the target polynucleotide sequence is present is made by a digital read module of an electronic detection system of the device 6000, in accordance with any of the methods described herein. In some embodiments, an electronic signal produced through the detection opening 6011 is not visible to the naked eye, but instead is read using another method. For example, in some embodiments, the reading of the device 6000 can include using a secondary device, such a mobile computing device to scan or otherwise receive the signal. In yet other embodiments, the reading the result can include indirectly reading a secondary signal produced by the device 6000 that conveys the results associated with (or describing) the primary output from the detection module 6800. Such secondary signal can be a light signal (e.g., from the LEDs), a series of flashing lights, a wireless signal (e.g., a short-range wireless signal, including Bluetooth or near field communication (NFC)).

The status light openings 6012 are aligned with one or more light output devices (e.g., LEDs) of the electronic control module 6900. In this manner, a light output produced by such status lights is visible through the status light openings 6012. Such light outputs can indicate, for example, whether the device 6000 is receiving power from the power source, whether an error has occurred (e.g., an error associated with insufficient sample volume or the like), and whether the test has been successfully completed. In some embodiments, the status lights can produce an output (e.g., various colors, flashing patterns, or the like) that provide an indication of the test result.

The detection module 6800 is configured to receive output from the amplification module 6600 and reagents from the reagent module 6700 to produce a colorimetric change to indicate presence or absence of target organism in the initial input sample. The detection module 6800 also produces a colorimetric signal to indicate the general correct operation of the test (positive control and negative control). The device 6000 (or any of the devices described herein) includes an electronic detection system (not shown, but which can be similar to the electronic detection system 5950) that automatically produces a binary signal based on the colorimetric signal produced by the detection module 6800.

Figure 34:
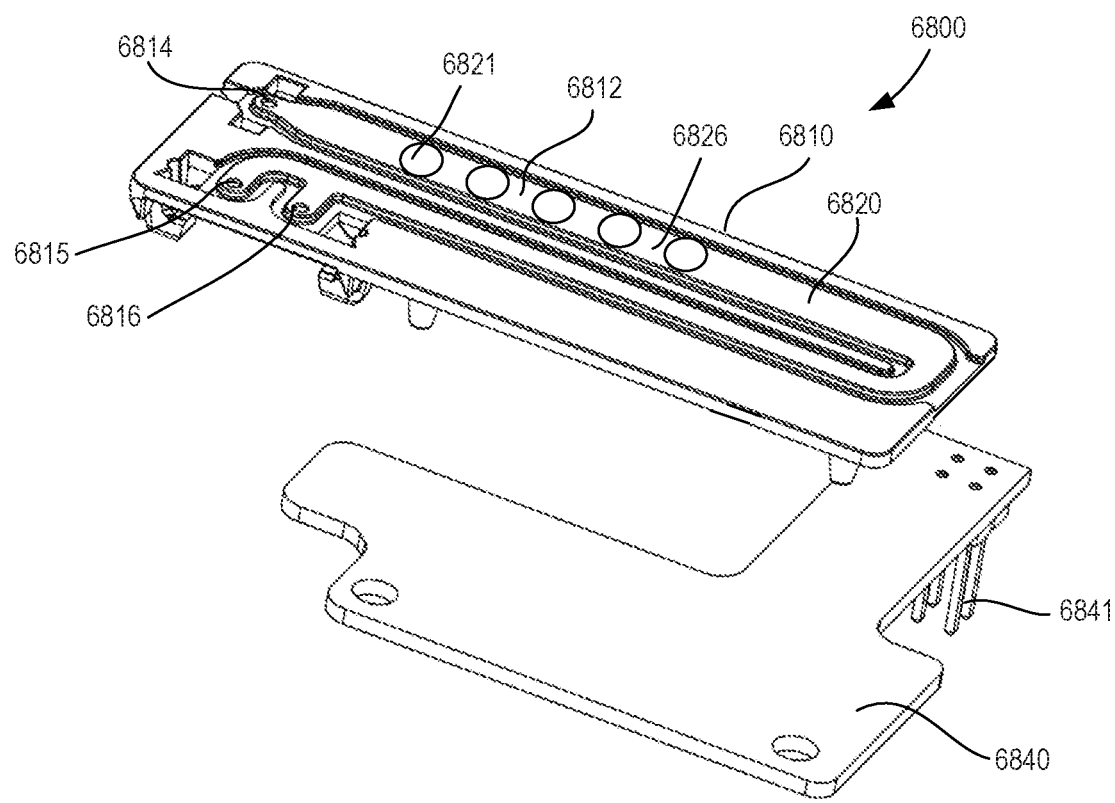
FIG. 34 is an exploded view of the detection module of the molecular diagnostic test device shown in FIGS. 31 and 32.

Referring to FIG. 34, the detection module includes a lid, a detection housing 6810 and a heater 6840. The heater 6840 can be similar to any of the circuit board heaters described herein and also shown and described in International Patent Publication No. WO2016/109691, entitled "Devices and Methods for Molecular Diagnostic Testing," which is incorporated herein by reference in its entirety. The lid and the detection housing 6810 form a flow cell for detection. The housing 6810 defines a detection chamber/channel 6812 having a sample inlet port 6814, a first reagent inlet/outlet port 6815, a second reagent inlet/outlet port 6816. The sample inlet port 6814 is fluidically coupled to the outlet of the amplification module 6600 and receives the amplified sample. The first reagent port 6815 and the second reagent port are coupled to the reagent module 6700 via a fluid interconnect. Thus, in use a wash/blocking reagent can be conveyed into the detection channel 6812 via the first reagent port 6815 or the second reagent port 6816. Similarly, a detection enzyme and a detection substrate can be conveyed into the detection channel 6812 via the first reagent port 6815 or the second reagent port 6816. Additionally, the first reagent port 6815 or the second reagent port 6816 can also be used to receive waste or excess reagents or flows out of the first reagent port 6815 or the second reagent port 6816.

The detection channel 6812 is surrounded or defined by a surface 6820 that includes one or more detection surfaces 6821, as well as non-detection surfaces 6826. The detection surfaces 6821 include a series of capture probes to which the target amplicon can be bound when the detection solution flows across the detection surface 6821. The capture probes can be any suitable probes formulated to capture or bind to the target amplicon. Specifically, in some embodiments, the detection portion 6821 includes five detection surfaces. Each of the detection surfaces are chemically modified to contain a desired capture probe configuration. In some embodiments, a first detection surface can include a hybridization probe specific to *Neisseria gonorrhea* (NG). A second detection surface can include a hybridization probe specific to *Chlamydia trachomatis* (CT). A third detection surface can include a hybridization probe specific to *Trichomonas vaginalis* (TV). A fourth detection surface can include non-target probe for a negative control. A fifth detection surface can include a hybridization probe for a positive control (*A. fischeri*, *N. subflava*, or the like). The non-detection surfaces 6826 can be those surfaces surrounding the detection surfaces 6821.

The detection operation is accomplished by conveying a series of reagents into the detection module at specific times. Although closing the lid 6050 actuates the reagent module 6700 to open (or release) the reagents from their respective sealed containers, the reagents remain in the reagent module 6700 until needed in the detection module 6800. When a particular reagent is needed, the rotary valve 6300 opens the appropriate vent path (i.e., the wash solution vent path 6315, the detection enzyme vent path 6316, and the detection substrate vent path 6317) to the reagent module 6700. Actuation of the fluidic drive module 6400 applies vacuum to the output port of the reagent module 6700 (via the detection module 6800), thus conveying the selected reagent from the reagent module 6700 into the detection module 6800.

As described herein, the device 6000 includes an electronic detection system that produces a digital signal indicating whether one of the detection surfaces 6821 has undergone a sufficient change in color to be considered as a positive result. In this manner, the device 6000 includes digital detection capability and does not rely on the user's judgment in determining whether any of the detection surfaces 6821 have undergone sufficient change to represent a positive test result. The detection circuit can produce one or more digital signals based on any suitable computer-related method for "reading" (or interpreting) one or more of the detection surfaces 6821. In some embodiments, the detection circuit can include one or more photodetectors and a computer-implemented module that determines a characteristic of the light associated with the detection surfaces 6821. In some embodiments, the computer-implemented module can execute an algorithm to detect a color produced by (or that characterizes) the detection surfaces 6821. In other embodiments, the computer-implemented module can execute an algorithm to detect a size or shape of the colored detection surface (e.g., using an edge detection algorithm).

In some embodiments, any of the diagnostic test devices described herein can include both digital detection capability as well as data output functionality. Similarly stated, any of the diagnostic test devices herein can include an electronic control system (e.g., similar to the electronic control system 5900) or an electronic detection system (e.g., similar to the electronic detection system 5950) that includes components and/or modules to send output signals to (or establish a communications connection with) a remote computing device (e.g., a smart phone). Such output signals can include information associated with the test, such as the test result for each detection surface (e.g., a positive or negative reading for each indication), an identification of the test device (e.g., a lot number), a time stamp associated with when the test was conducted, or any other suitable information. The output signal can be any suitable signal, such as a short-range wireless signal, cellular telephone wireless signals (to directly access a remote server without requiring a short-range connection), or a RFID signal. In other embodiments, the output signal can be a light signal in the visible spectrum. For example, in some embodiments, the signal can include a series of light flashes produced by the status light (e.g., status lights that produce light via the status light openings 5012 described above).

Figure 35:
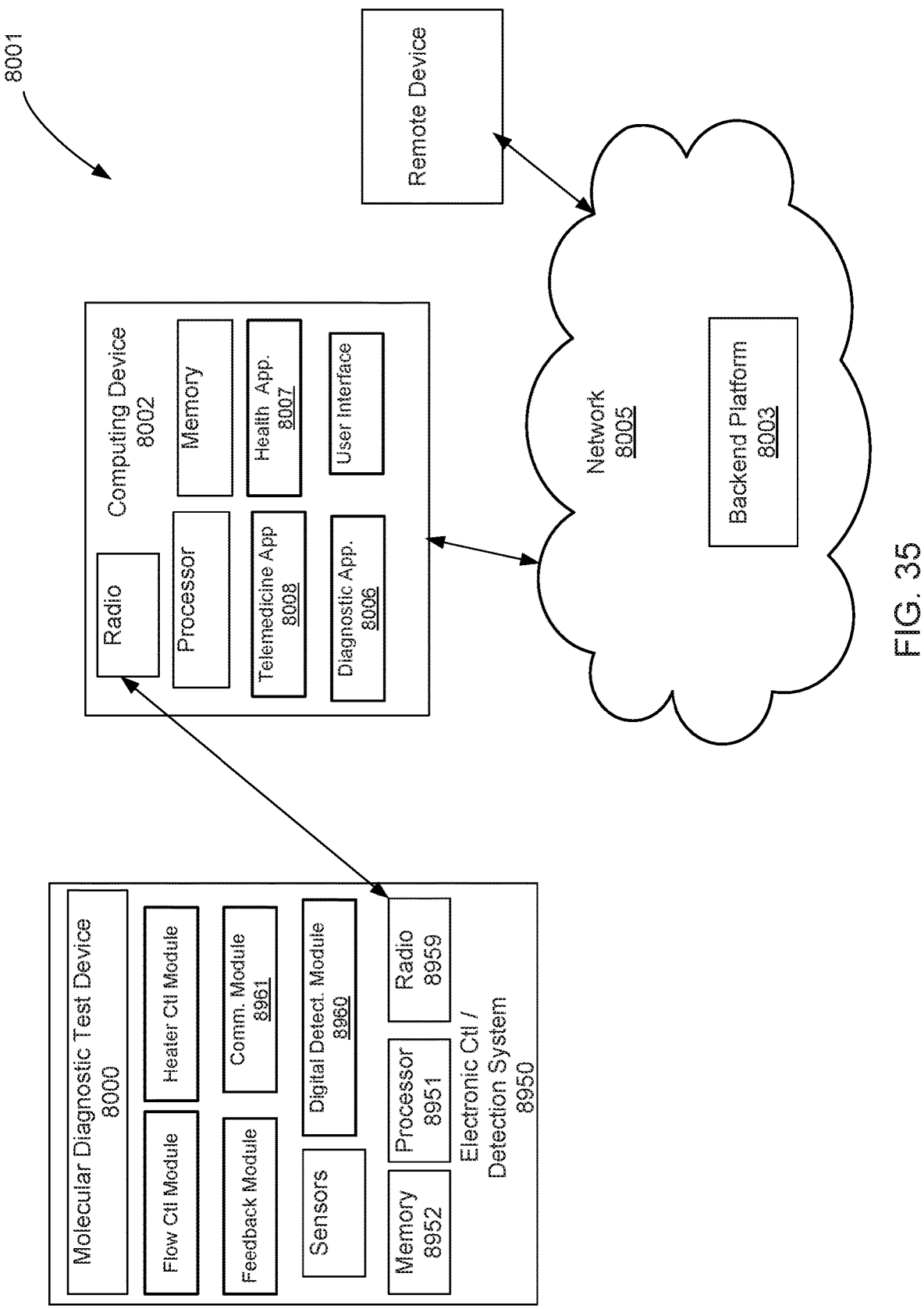
FIG. 35 is a schematic illustration of a connected health system including a molecular diagnostic test device having wireless connectivity, according to an embodiment.

FIG. 35 is a schematic illustration of a molecular diagnostic test system 8001 (also referred to herein as "the connected health system 8001" or the "system 8001") according to an embodiment. The system 8001 includes a molecular diagnostic test device 8000, a first remote computing device 8002, one or more second remote computing devices, and a backend platform 8003. The components, modules, and/or functions described in connection with the connected health system 8001 can be included within any of the connected health systems described herein. Similarly, the components, modules and/or functions described in the other connected health systems described herein can be included in the connected health system 8001.

The backend platform 8003 can be any suitable computer-implemented interface and/or computing entity, such as a server or personal computer, that is configured to communicate via the network 8005 with the remote computing device 8002, the secondary remote computing device, and/or any other portions of the connected health system 8001 (e.g., a call center interface, a payer/provider interface, or the like). More specifically, the backend platform 8003 can receive information from devices within the connected health system 8001, manipulate the information, and produce information to any other devices within the connected health system 8001. For example, in some embodiments, the backend platform 8003 can be associated with a healthcare provider (HCP), an electronic health record (EHR) database, a governmental entity for tracking disease, or the like. In some embodiments, test result information (e.g., positive/negative results) associated with the molecular diagnostic test device 8000 can be transmitted from the device 8000 to the remote computing device 8002. The remote computing device 8002 can transmit the test result information (e.g., via the network 8005) to the backend platform 8003. Based on the test result information, the backend platform 8003 can transmit notifications back to the remote computing device 8002 and/or the secondary remote computing device (e.g., a caregiver's device) to establish a telemedicine session, provide follow-up care instructions, to provide a prescription for treatment, or the like. In this manner, the backend platform 8003 can control and/or manage certain notifications and/or features.

The network 8005 can be a piconet, the Internet, an intranet, a local area network (LAN), a wide area network (WAN), a virtual network, a telecommunications network, any other suitable communication system and/or combination of such networks. The network 8005 can be implemented as a wired and/or wireless network. Although FIG. 35 shows the molecular diagnostic test device 8000 being coupled to the network 8005 via the computing device 8002, in other embodiments, the molecular diagnostic test device 8000 can be coupled to (or connected with) the network via any suitable mechanism and/or by any protocol.

The molecular diagnostic test device 8000 can be any of the molecular diagnostic test devices described herein. The molecular diagnostic test device 8000 can be a stand-alone device similar to the molecular diagnostic test device 6000 described herein. The molecular diagnostic test device 8000 includes or is attached to an electronic control system 8950. For example, in some embodiments, the electronic control system 8950 can be coupled to and/or within a housing of the molecular diagnostic test device 8000, like the electronic control module 6950 described herein. The electronic control system 8950 includes a processor 8951, a memory 8952, one or more sensors, and a radio 8959. The electronic control system 8950 also includes a communication module 8961 and a digital detection module 8960. The electronic control system 8950 also includes other modules for controlling the device (e.g., a flow control module, a heater control module, and a feedback module. Although shown as including each of these application modules, in other embodiments, an electronic control system need not include all (or any) of these modules, and can include any other modules described herein.

The processor 8951, and any of the processors described herein can be any suitable processor for performing the methods described herein. In some embodiments, processor 8951 can be configured to run and/or execute application modules, processes and/or functions associated with the molecular diagnostic test device 8000. For example, the processor 8951 can be configured to run and/or execute the communication module 8961, the digital detection module 8960, and/or any of the other modules described herein, and perform the methods associated therewith. The processor 8951 can be, for example, a Field Programmable Gate Array (FPGA), an Application Specific Integrated Circuit (ASIC), a Digital Signal Processor (DSP), and/or the like. The processor 8951 can be configured to retrieve data from and/or write data to memory, e.g., the memory 8952. As described herein, in some embodiments, the processor 8951 can cooperatively function with the radio 8959 and/or execute instructions from code to provide signals to communicatively couple to the computing device 8002 (e.g., via wireless communication) and/or any other computing entity via a network 8005. In some embodiments, the processor 8951 is a Bluetooth® low energy (BLE) processor.

The memory 8952 can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth. In some embodiments, the memory 8952 stores instructions to cause the processor 8951 to execute modules, processes and/or functions associated with the molecular diagnostic test device 8000. For example, the memory 8952 can store instructions to cause the processor 8951 to execute any of the application modules described herein, and perform the methods associated therewith. In some embodiments, the memory 8952 stores information, such as one or more short-term or long-term security keys received from and/or exchanged with the remote computing device 8002 as a part of the pairing and/or bonding process described herein.

The sensor(s) included within the electronic control system 8950 can include any number of switches, optical/light input sensors, temperature sensors, contact sensors, and/or any other suitable input device. In some embodiments, the sensor(s) can include any of the sensors described herein. For example, in some embodiments, the sensor(s) can include one or more photodiodes, as described above.

The radio 8959 (also referred to as a receiver, transmitter and/or transceiver) can be operable to send signals to, and/or receive radio signals, such as Bluetooth®, ZigBee, Wi-Fi, cellular telephone signals, etc. In some embodiments, such as embodiments where the processor 8951 is Bluetooth® processor, the radio 8959 can be integral with the processor 8951. In other embodiments, the radio 8959 can include a processor distinct from the processor 8951. In some embodiments, the radio 8959 can be operable to communicatively couple (also referred to herein as "linking," "pairing," or "bonding") the electronic control system 8950 to the computing device 8002 and/or any other computing entity via a network 8005.

The digital detection module 8960 can be a hardware and/or software module (stored in memory 8952 and/or executed in the processor 8951). The digital detection module 8960 is configured to receive a signal (e.g., from one or more photodiodes) and determine, based on the signal a test result (e.g., a positive or negative). Functions of the digital detection module (or circuit) are described above.

The communication module 8961 can be a hardware and/or software module (stored in memory 8952 and/or executed in the processor 8951). The communication module 8961 is configured to receive an indication (e.g., from the sensor(s)) and/or test result information from the digital detection module 8960 and transmit an output signal associated with the test result.

The remote computing device 8002 (or secondary remote computing device) can be a mobile computing entity, such as a smart mobile phone (e.g., an iPhone®, an Android® device, a Windows® phone, a Blackberry® phone, etc.), a tablet computer (e.g., an Apple iPad®, a Samsung Nexus® device, a Microsoft Surface® device, etc.), or a computer (e.g., a laptop, desktop, smart TV, etc.), and/or any other suitable computing entity. For example, in some embodiments, the remote computing device 8002 can be the patient's smart phone. In other embodiments, the remote computing device 8002 can be a computer or system of computers at a point of care setting (e.g., a doctor's office). The remote computing device 8002 includes a processor, a memory, a user interface, and a radio. Additionally, although the remote computing device 8002 is shown as being operably coupled to the molecular diagnostic test device 8000 by a wireless signal (e.g., transmitted by the radio 8959, in other embodiments, the remote computing device 8002 can be operably coupled to the molecular diagnostic test device 8000 by wired connection, such as, for example, via a USB connection. Accordingly, the computer-implemented methods described herein (e.g., the method 60 shown in FIG. 38) can be performed via a hard-wired connection.

The remote computing device 8002 also includes one or more modules or software applications. For example, in some embodiments, the remote computing device 8002 can include a diagnostic application 8006 that is specific to the molecular diagnostic test device 8000. The diagnostic application 8006 can perform the pairing and/or onboarding functions to establish an appropriate connection between the remote computing device 8002 and the molecular diagnostic test device 8000 and the backend platform 8003. For example, in some embodiments, the diagnostic application 8006 to cause the remote computing device 8002 to produce a series of prompts and information (e.g., via the user interface) to facilitate the creation of a user account within the connected health system 8001. Specifically, the diagnostic application 8006 can cause the remote computing device 8002 to produce one or more graphical user interface (GUI) elements that prompt the user to enter information associated with the patient, including (but not limited to) demographic information, health history information, and identification information. The diagnostic application 8006 can also cause the remote computing device 8002 to produce one or more graphical user interface (GUI) elements that prompt the user to enter information associated with the patient's primary care provider, pharmacy, insurance company, or other entities associated with the patient's health care network (including authorization for sharing information). In some embodiments, for example, the diagnostic application 8006 can also cause the remote computing device 8002 to produce one or more graphical user interface (GUI) elements that prompt the user to enter information associated with a telemedicine provider.

In some embodiments, the diagnostic application 8006 can cause the remote computing device 8002 to display one or more GUI elements providing details or instructions for the user. In some embodiments, the diagnostic application 8006 can cause the remote computing device 8002 to display a video showing instructions for collecting the patient sample (e.g., an instruction for taking a swab sample).

In some embodiments, the diagnostic application 8006 can exchange information to and/or receive information from other software applications. As shown, the remote computing device 8002 can include a health application 8007 (e.g., the Apple Health App), a telemedicine application 8008 (e.g., the MinuteClinic® App, a telemedicine app by Kareo, etc.). Thus, in some embodiments, the diagnostic application 8006 can exchange information regarding a test result, demographic information, etc. with the health application 8007, the telemedicine application 8008, or any other applications operating on the remote computing device 8002.

Figure 36:
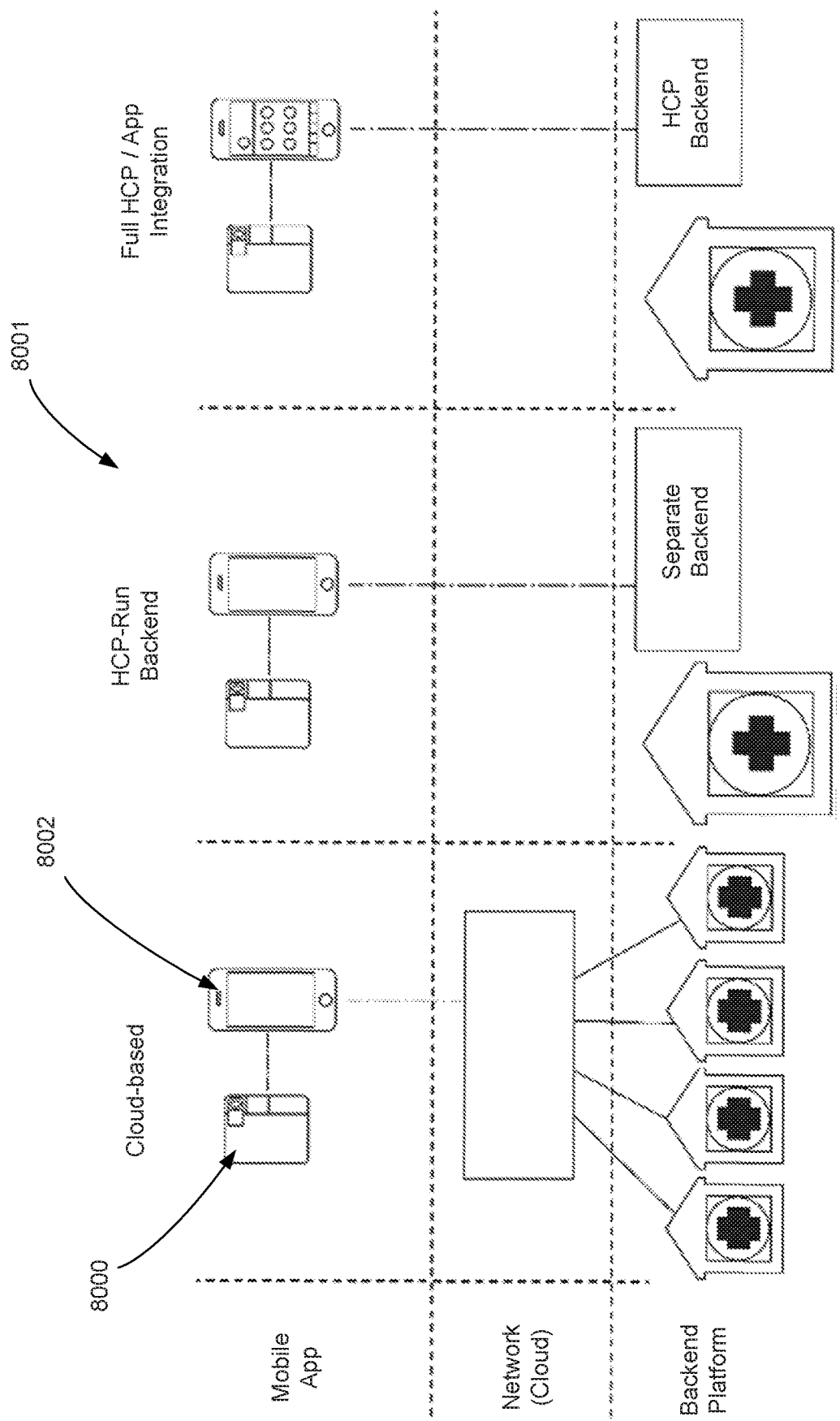
FIG. 36 shows a schematic illustration of a connected health system that facilitates electronic health record (EHR) integration, according to an embodiment.

FIG. 36 shows a schematic illustration of a portion of the connected health system 8001 showing various options for facilitating electronic health record (EHR) integration, according to an embodiment. In particular, FIG. 36 shows three different integration options.

Figure 37:
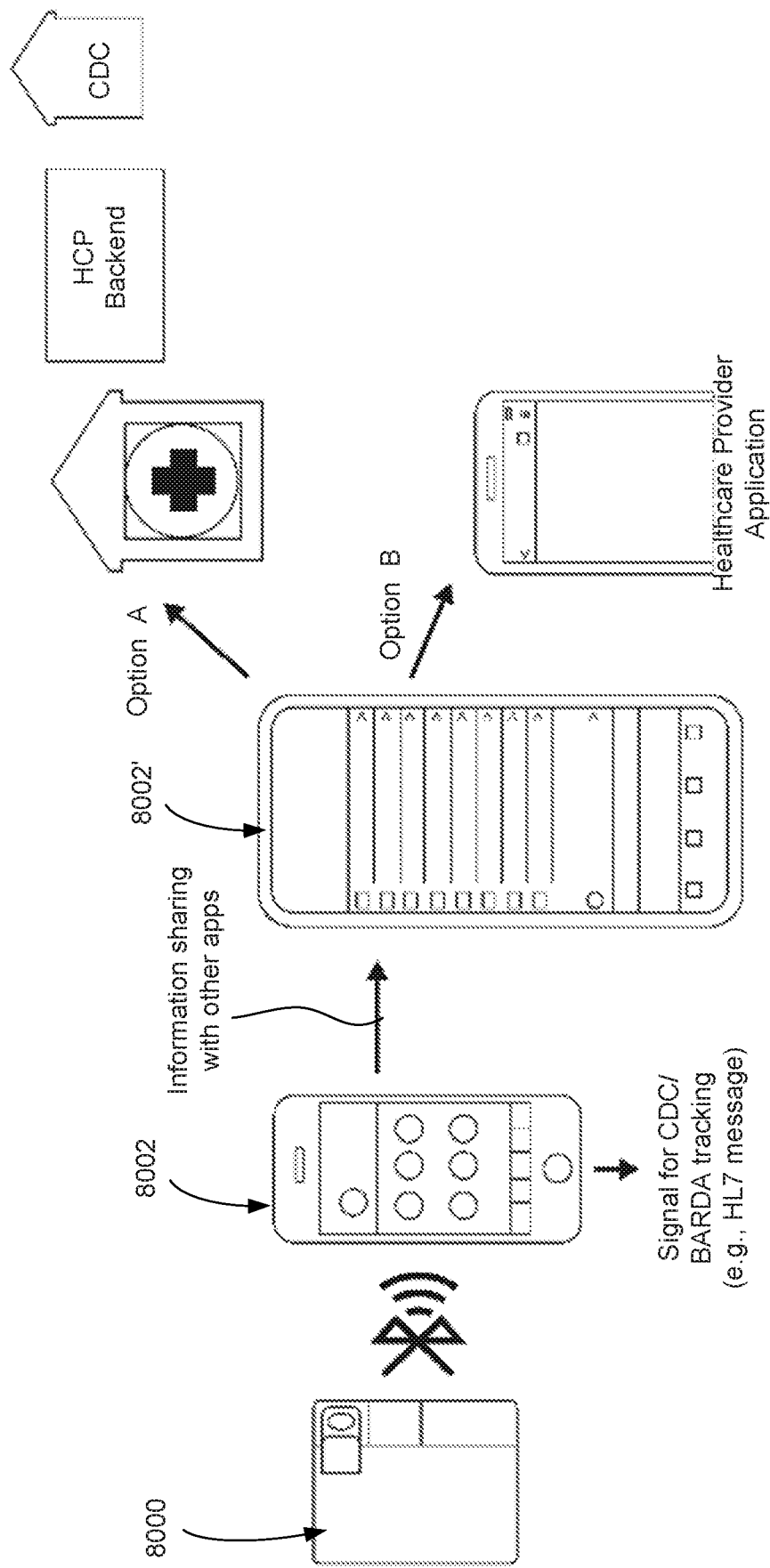
FIG. 37 shows a schematic illustration of a connected health system that facilitates integration of a smartphone application via the application Apple Health, according to an embodiment.

FIG. 37 shows a schematic illustration of a connected health system that facilitates integration of a smartphone application via the application Apple Health, according to an embodiment. As shown, in some embodiments, an application associated with the molecular diagnostic test device (e.g., the diagnostic application 8006) can send a HL7 message. In some embodiments, the application can de-identify the information in the message to protect privacy of the patient. For example, in some embodiments, the information transmitted can include any of a location (e.g., via GPS information from the user's remote computing device), a time stamp associated with a test result, an identification of the test device, and the test results. In this manner, the de-identified data (i.e., data that includes no personal information associated with the patient) can be used by governmental agencies (e.g., CDC/BARDA) for disease tracking and/or surveillance purposes. In other embodiments, such data can be sent to healthcare providers, payers, or others.

In some embodiments, a method includes real-time (or quasi-real-time) surveillance data collection, enabled by the systems described herein. Eliminating the traditional batch collection (or periodic transmission of data to CDC/BARDA) can allow for more immediate notification of a potential health threat (e.g., pandemic, biothreat, etc.). In some embodiments, the HL7 message can be associated with a standardized interface (e.g., HL7 clinical document architecture record).

In some embodiments, an application associated with the molecular diagnostic test device (e.g., the diagnostic application 8006) can exchange information with other applications resident on the remote computing device 8002 or another remote computing device 8002' (e.g., a caregiver's device). Such information can be shared via the HealthKit API and Clinical Document Architecture (CDA) object, or any other suitable protocol.

As shown, FIG. 37 shows different integration options, as discussed above. For example, "Option A" provides an HCP interface with the Health application (e.g., the application 8007). In this option, the Health application receives information associated with the test result (e.g., from the diagnostic application 8006) and provides information to the patient as well as various backend functions (e.g., via the interface with the backend platform). "Option B" provides for direct interface with the healthcare provider application. In this option, the records can be transferred via the HealthKit API and the healthcare provider application (e.g., the telemedicine application 8008) can provide instructions, perform backend functions, etc.

Figure 38:
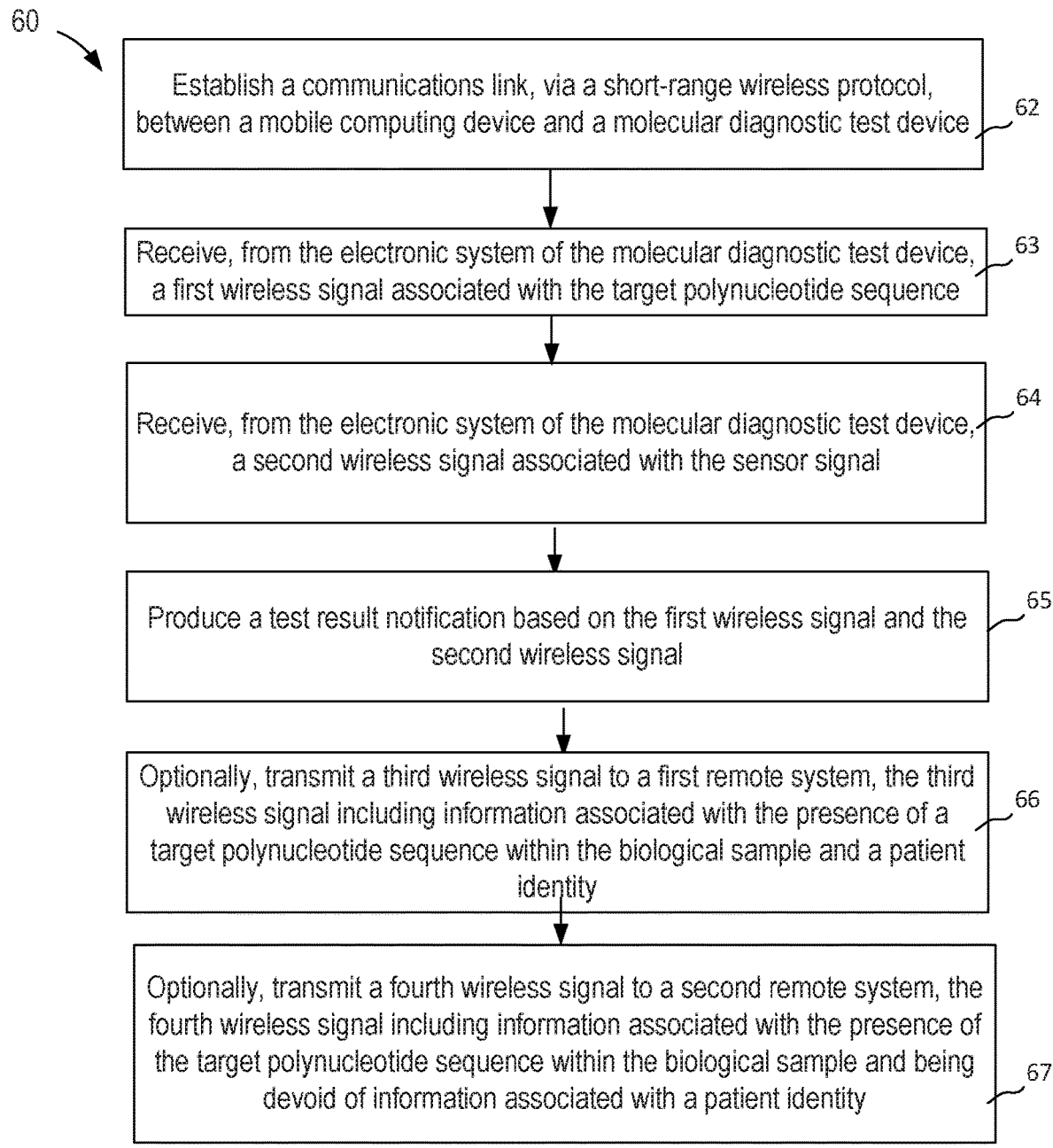
FIG. 38 is a flow chart of a method for transmitting data from a molecular diagnostic test device, according to an embodiment.

FIG. 38 is a flow chart of a method 60 of transmitting data from a molecular diagnostic test device, according to an embodiment. The method 60 can be performed by a digital read module, communication module, or any other application modules described herein. The method 60 can be performed by and/or within the connected health system 8001 or can be performed by any of the connected health systems (or include any of the components) described herein. The method 60 includes establishing a communications link, via a short-range wireless protocol, between a mobile computing device and a molecular diagnostic test device, at 62. The molecular diagnostic test device can be any of the molecular diagnostic test devices described herein. Specifically, the molecular diagnostic test device can include a housing, a detection module within the housing, a reagent within the housing, and an electronic system within the housing. The detection module, which can be similar to the detection modules 3800, 5800 or 6800 defines a detection volume into which a biological sample can be conveyed. The reagent is formulated to facilitate production of an assay signal within the detection module after the biological sample (or portions thereof) and the reagent are combined within (or each introduced into) the detection volume. The assay signal indicates the presence of a target polynucleotide sequence within the biological sample. As described herein, the electronic system includes a sensor (e.g., a photodetector) configured to produce a sensor signal associated with the assay signal. The short-range wireless protocol can be any of the protocols described herein, including the Bluetooth® wireless protocol.

A first wireless signal associated with the target polynucleotide sequence is received from the electronic system of the molecular diagnostic test device, at 63. The first wireless signal can be an initialization signal indicating that the molecular diagnostic test device has been turned on, that the sample lid has been closed, that identifies the type of pathogen(s) that are to be tested by the device, a unique identifier of the molecular diagnostic test device, or the like. The first wireless signal can be received at any time and in any manner consistent with the communications link and/or wireless protocol established. For example, in some embodiments, such as when the molecular diagnostic test device in proximity to the mobile computing device, the wireless signal can be received contemporaneously upon completion of the test. In other embodiments, the molecular diagnostic test device may not be in communication range with the mobile computing device, and the first wireless signal can be received at a later time when the communication link is established.

A second wireless signal associated with the sensor signal is received from the electronic system of the molecular diagnostic test device, at 64. The sensor signal can be any of the sensor signals described herein and can indicate whether the target polynucleotide sequence is present. The method further includes producing a test result notification based on the first wireless signal and the second wireless signal, at 65. The notification can be, for example, a visual notification produced by a touch screen or user interface of the mobile computing device. In other embodiments, the notification can be an audible or haptic output produced by the mobile computing device that indicates the test result.

In some embodiments, the method optionally includes transmitting a third wireless signal to a first remote system, at 66. The third wireless signal includes information associated with the presence of a target polynucleotide sequence within the biological sample and a patient identity. The third wireless signal can be transmitted to a health care provider (i.e., operating the first remote system) of the patient and can be used to provide a prescription, unique to the patient, to treat the condition detected by the molecular diagnostic test device.

In some embodiments, the method optionally includes transmitting a fourth wireless signal to a second remote system, at 67. The fourth wireless signal includes information associated with the presence of the target polynucleotide sequence within the biological sample and being devoid of information associated with a patient identity. The fourth wireless signal can be transmitted to an organization, such as CDC (i.e., operating the second remote system) and can be used to provide track general health results, without the patient's identity.

In some embodiments, the molecular diagnostic test devices and connected health systems described herein can enable a self-test administered at a decentralized location (e.g., at home) and a telemedicine application to provide follow-up care. There are several potential home-use models, including "Scenario 1" where the patient has the molecular diagnostic test device prior to getting ill or displaying symptoms (e.g., "device on hand") and "Scenario 2" where the patient contacts their physician via a telemedicine smartphone app and is guided to purchase the molecular diagnostic test device and perform the test to verify their condition.

In some embodiments, the method can optionally include transmitting information from the first application (e.g., the diagnostic application 8006) to a second application that functions as a telemedicine application. In this manner, if the device 8000 is provided as an OTC solution, the connected health system can ensure a robust and reliable connection (and access to) a telemedicine provider and application. This arrangement ensures that proper instructions will be provided for taking sample, operating the device 8000, and taking appropriate follow-up steps.

In some embodiments, the method includes, receiving from the second application (e.g., the telemedicine application), a validation code. If the validation code is not received, indicating that the patient has not properly engaged the telemedicine application, the test result notification includes an error message indicating an invalid test. In this manner, the connected health system can ensure that the telemedicine application has been accessed before providing a test result. This arrangement may reduce the likelihood of misuse, improper sampling, and/or the patient not following up on post-test procedures.

FIG. 39 is a schematic illustration showing the workflow for Scenario 1 above, as it relates to a molecular diagnostic test device 8000 being sold through a pharmacy and the patient-to-physician interaction via a pharmacy-specific smartphone application (e.g., the telemedicine application 8008). In Scenario 1, if the patient feels sick, the patient can consult with a practitioner (nurse, doctor, pharmacist) or via a preselected set of questions provided by the telemedicine application. If the conditions are such that conducting the diagnostic test is appropriate, the telemedicine application will produce a notification providing information for and/or instructions to complete the test (step A). The test result will be transmitted either to the remote computing device via any of the methods described herein (see step B), such as via wireless communication or hardwired communication (e.g., USB connection). The test result will be transmitted either directly from the device 8000 to the telemedicine application, or it will be transmitted from a diagnostic application (e.g., the diagnostic application 8006) to the telemedicine application (see step C). The test result is then automatically sent to the pharmacy or other healthcare providers (or to CDC/BARDA for monitoring). If the result is positive (step D), the healthcare provider (e.g., nurse practitioner) reviews the test and prescribes the appropriate treatment. The prescription can be transmitted to the appropriate pharmacy for pickup by the patient or their caregiver. If, however, the test is negative (step E), no prescription is provided.

FIG. 40 is a schematic illustration showing the workflow for Scenario 2 above where use of the diagnostic test device is recommended via the telemedicine interaction prior to prescription of an antiviral treatment.

Although the schematics described above show the molecular diagnostic test device being coupled to the remote computing device via a wireless communications connection (e.g., Bluetooth or NFC), in other embodiments, the molecular diagnostic test device can be coupled to the remote computing device via a USB power connector. This interface provides bi-directional communication with an external computer for development testing, software updates, and debugging.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. While the embodiments have been particularly shown and described, it will be understood that various changes in form and details may be made.

For example, although the amplification modules are generally described herein as performing a thermal cycling operation on the prepared solution, in other embodiment, an amplification module can perform any suitable thermal reaction to amplify nucleic acids within the solution. In some embodiments, any of the amplification modules described herein can perform any suitable type of isothermal amplification process, including, for example, Loop Mediated Isothermal Amplification (LAMP), Nucleic Acid Sequence Based Amplification (NASBA), which can be useful to detect target RNA molecules, Strand Displacement Amplification (SDA), Multiple Displacement Amplification (MDA), Ramification Amplification Method (RAM), or any other type of isothermal process.

As another example, any of the sample input modules, sample preparation modules, amplification modules, heater assemblies, and detection modules shown and described herein can be used in any suitable diagnostic device. Such devices can include, for example, a single-use device that can be used in a point-of-care setting and/or in a user's home. Similarly stated, in some embodiments, the device (and any of the other devices shown and described herein) can be configured for use in a decentralized test facility. Further, in some embodiments, any of the sample input modules, sample preparation modules, amplification modules, heater assemblies, and detection modules shown and described herein can be included within a CLIA-waived device and/or can facilitate the operation of a device in accordance with methods that are CLIA waived. Similarly stated, in some embodiments, the sample input modules, the sample preparation modules, the amplification modules, and the detection modules shown and described herein can facilitate operation of a device in a sufficiently simple manner that can produce results with sufficient accuracy to pose a limited likelihood of misuse and/or to pose a limited risk of harm if used improperly. In some embodiments, the sample input modules, the sample preparation modules, the amplification modules, and the detection modules shown and described herein can be used in any of the diagnostic devices shown and described in International Patent Publication No. WO2016/109691, entitled "Devices and Methods for Molecular Diagnostic Testing," which is incorporated herein by reference in its entirety," which is incorporated herein by reference in its entirety.

Although the electronic detection system 3950 is shown and described as including pairs of LEDs and photodiodes, in other embodiment any of the electronic detection system described herein can include any suitable light-emitting components and light detecting components.

The devices and methods described herein can be used to analyze any suitable type of biological sample, such as a tissue sample (e.g., a blood sample). In some cases, the biological sample comprises a bodily fluid taken from a subject. In some cases, the bodily fluid includes one or more cells comprising nucleic acids. In some cases, the one or more cells comprise one or more microbial cells, including, but not limited to, bacteria, archaebacteria, protists, and fungi. In some cases, the biological sample includes one or more virus particles. In some cases, the biological sample includes one or more microbes that causes a sexually-transmitted disease. A sample may comprise a sample from a subject, such as whole blood; blood products; red blood cells; white blood cells; buffy coat; swabs; urine; sputum; saliva; semen; lymphatic fluid; endolymph; perilymph; gastric juice; bile; mucus; sebum; sweat; tears; vaginal secretion; vomit; feces; breast milk; cerumen; amniotic fluid; cerebrospinal fluid; peritoneal effusions; pleural effusions; biopsy samples; fluid from cysts; synovial fluid; vitreous humor; aqueous humor; bursa fluid; eye washes; eye aspirates; plasma; serum; pulmonary lavage; lung aspirates; animal, including human, tissues, including but not limited to, liver, spleen, kidney, lung, intestine, brain, heart, muscle, pancreas, cell cultures, as well as lysates, extracts, or materials and fractions obtained from the samples described above or any cells and microorganisms and viruses that may be present on or in a sample. A sample may include cells of a primary culture or a cell line. Examples of cell lines include, but are not limited to, 293-T human kidney cells, A2870 human ovary cells, A431 human epithelium, B35 rat neuroblastoma cells, BHK-21 hamster kidney cells, BR293 human breast cells, CHO chinese hamster ovary cells, CORL23 human lung cells, HeLa cells, or Jurkat cells. The sample may include a homogeneous or mixed population of microbes, including one or more of viruses, bacteria, protists, monerans, chromalveolata, archaea, or fungi. The biological sample can be a urine sample, a vaginal swab, a cervical swab, an anal swab, or a cheek swab. The biological sample can be a nasal swab, including a mid-turbinate swab, a nasopharyngeal swab, or an anterior nares swab. The biological sample can be obtained from a hospital, laboratory, clinical or medical laboratory.

The devices and methods described herein, however, are not limited to performing a molecular diagnostic test on human samples. In some embodiments, any of the devices and methods described herein can be used with veterinary samples, food samples, and/or environmental samples. Examples of environmental sources include, but are not limited to agricultural fields, lakes, rivers, water reservoirs, air vents, walls, roofs, soil samples, plants, and swimming pools. Examples of industrial sources include, but are not limited to clean rooms, hospitals, food processing areas, food production areas, food stuffs, medical laboratories, pharmacies, and pharmaceutical compounding centers. Examples of subjects from which polynucleotides may be isolated include multicellular organisms, such as fish, amphibians, reptiles, birds, and mammals. Examples of mammals include primates (e.g., apes, monkeys, gorillas), rodents (e.g., mice, rats), cows, pigs, sheep, horses, dogs, cats, or rabbits. In some examples, the mammal is a human.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or microinstructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

The processor included within a control module (and any of the processors and/or controllers described herein) can be any processor configured to, for example, write data into and read data from the memory of the controller, and execute the instructions and/or methods stored within the memory. Furthermore, the processor can be configured to control operation of the other modules within the controller (e.g., the temperature feedback module and the flow module). Specifically, the processor can receive a signal including temperature data, current measurements or the like and determine an amount of power and/or current to be supplied to each heater assembly, the desired timing and sequence of the piston pulses and the like. For example, in some embodiments, the controller can be an 8-bit PIC microcontroller, which will control the power delivered to various heating assemblies and components within the amplification module 4600. This microcontroller can also contain code for and/or be configured to minimize the instantaneous power requirements on the power source.

In other embodiments, any of the processors described herein can be, for example, an application-specific integrated circuit (ASIC) or a combination of ASICs, which are designed to perform one or more specific functions. In yet other embodiments, the microprocessor can be an analog or digital circuit, or a combination of multiple circuits.

Any of the memory devices described herein can be any suitable device such as, for example, a read only memory (ROM) component, a random access memory (RAM) component, electronically programmable read only memory (EPROM), erasable electronically programmable read only memory (EEPROM), registers, cache memory, and/or flash memory. Any of the modules (the pressure feedback module and the position feedback module) can be implemented by the processor and/or stored within the memory.

Although various embodiments have been described as having particular features and/or combinations of components, other embodiments are possible having a combination of any features and/or components from any of embodiments as discussed above.

Any of the devices and methods described herein can be utilized to detect the presence or absence of nucleic acids associated with one or more bacterial cells in a biological sample. In some embodiments, the one or more bacterial cells are pathogens. In some embodiments, the one or more bacterial cells are infectious. Non-limiting examples of bacterial pathogens that can be detected include Mycobacteria (e.g., *M. tuberculosis, M. bovis, M. avium, M. leprae,* and *M. africanum*), *rickettsia, mycoplasma, chlamydia,* and *legionella*. Some examples of bacterial infections include, but are not limited to, infections caused by Gram positive *bacillus* (e.g., *Listeria, Bacillus* such as *Bacillus anthracis, Erysipelothrix* species), Gram negative *bacillus* (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio* and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, Pneumococcus species, *Staphylococcus* species, and *Neisseria* species. Specific examples of infectious bacteria include, but are not limited to: *Helicobacter pyloris, Legionella pneumophilia, Mycobacterium tuberculosis, Mycobacterium avium, Mycobacterium intracellulare, Mycobacterium kansaii, Mycobacterium gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus faecalis, Streptococcus bovis, Streptococcus pneumoniae, Haemophilus influenzae, Bacillus antracis, Erysipelothrix rhusiopathiae, Clostridium tetani, Enterobacter aerogenes, Klebsiella pneumoniae, Pasteurella multocida, Fusobacterium nucleatum, Streptobacillus moniliformis, Treponema pallidium, Treponema pertenue, Leptospira, Rickettsia,* and *Actinomyces israelii, Acinetobacter, Bacillus, Bordetella, Borrelia, Brucella, Campylobacter, Chlamydia, Chlamydophila, Clostridium, Corynebacterium, Enterococcus, Haemophilus, Helicobacter, Mycobacterium, Mycoplasma, Stenotrophomonas, Treponema, Vibrio, Yersinia, Acinetobacter baumanii, Bordetella pertussis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Corynebacterium diphtheriae, Enterobacter sazakii, Enterobacter agglomerans, Enterobacter cloacae, Enterococcus faecalis, Enterococcus faecium, Escherichia coli, Francisella tularensis, Helicobacter pylori, Legionella pneumophila, Leptospira interrogans, Mycobacterium leprae, Mycobacterium tuberculosis, Mycobacterium ulcerans, Mycoplasma pneumoniae, Pseudomonas aeruginosa, Rickettsia rickettsii, Salmonella typhi, Salmonella typhimurium, Salmonella enterica, Shigella sonnei, Staphylococcus epidermidis, Staphylococcus saprophyticus, Stenotrophomonas maltophilia, Vibrio cholerae, Yersinia pestis,* and the like. In some instances, the infectious bacteria is *Neisseria gonorrhoeae* or *Chlamydia trachomatis*.

Any of the devices and methods described herein can be utilized to detect the presence or absence of nucleic acids associated with one or more viruses in a biological sample, including influenza, SARS-CoV-2. Non-limiting examples of viruses include the herpes virus (e.g., human cytomegalomous virus (HCMV), herpes simplex virus I (HSV-1), herpes simplex virus 2 (HSV-2), varicella zoster virus (VZV), Epstein-Barr virus), influenza A virus and Hepatitis C virus (HCV) or a picornavirus such as Coxsackievirus B3 (CVB3). Other viruses may include, but are not limited to, the hepatitis B virus, HIV, poxvirus, hepadavirus, retrovirus, and RNA viruses such as flavivirus, togavirus, coronavirus, Hepatitis D virus, orthomyxovirus, paramyxovirus, rhabdovirus, bunyavirus, filo virus, Adenovirus, Human herpesvirus, type 8, Human papillomavirus, BK virus, JC virus, Smallpox, Hepatitis B virus, Human bocavirus, Parvovirus B 19, Human astrovirus, Norwalk virus, coxsackievirus, hepatitis A virus, poliovirus, rhinovirus, Severe acute respiratory syndrome virus, Hepatitis C virus, yellow fever virus, dengue virus, West Nile virus, Rubella virus, Hepatitis E virus, and Human immunodeficiency virus (HIV). In some embodiments, the virus is an enveloped virus. Examples of such enveloped viruses include, but are not limited to, viruses that are members of the hepadnavirus family, herpesvirus family, iridovirus family, poxvirus family, flavivirus family, togavirus family, retrovirus family, coronavirus family, filovirus family, rhabdovirus family, bunyavirus family, orthomyxovirus family, paramyxovirus family, and arenavirus family. Other examples include, but are not limited to, Hepadnavirus hepatitis B virus (HBV), woodchuck hepatitis virus, ground squirrel (Hepadnaviridae) hepatitis virus, duck hepatitis B virus, heron hepatitis B virus, Herpesvirus herpes simplex virus (HSV) types 1 and 2, varicellazoster virus, cytomegalovirus (CMV), human cytomegalovirus (HCMV), mouse cytomegalovirus (MCMV), guinea pig cytomegalovirus (GPCMV), Epstein-Barr virus (EBV), human herpes virus 6 (HHV variants A and B), human herpes virus 7 (HHV-7), human herpes virus 8 (HHV-8), Kaposi's sarcoma—associated herpes virus (KSHV), B virus Poxvirus vaccinia virus, variola virus, smallpox virus, monkeypox virus, cowpox virus, camelpox virus, ectromelia virus, mousepox virus, rabbitpox viruses, raccoon pox viruses, molluscum contagiosum virus, orf virus, milker's nodes virus, bovin papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, Yabapox virus, Flavivirus dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, Kyasanur Forest disease virus, Togavirus, Venezuelan equine encephalitis (VEE) virus, chikungunya virus, Ross River virus, Mayaro virus, Sindbis virus, rubella virus, Retrovirus human immunodeficiency virus (HIV) types 1 and 2, human T cell leukemia virus (HTLV) types 1, 2, and 5, mouse mammary tumor virus (MMTV), Rous sarcoma virus (RSV), lentiviruses, Coronavirus, severe acute respiratory syndrome (SARS) virus, Filovirus Ebola virus, Marburg virus, Metapneumoviruses (MPV) such as human metapneumovirus (HMPV), Rhabdovirus rabies virus, vesicular stomatitis virus, Bunyavirus, Crimean-Congo hemorrhagic fever virus, Rift Valley fever virus, La Crosse virus, Hantaan virus, Orthomyxovirus, influenza virus (types A, B, and C), Paramyxovirus, parainfluenza virus (PIV types 1, 2 and 3), respiratory syncytial virus (types A and B), measles virus, mumps virus, Arenavirus, lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Punta torn virus (PTV), Tacaribe virus and Tamiami virus. In some embodiments, the virus is a non-enveloped virus, examples of which include, but are not limited to, viruses that are members of the parvovirus family, circovirus family, polyoma virus family, papillomavirus family, adenovirus family, iridovirus family, reovirus family, birnavirus family, calicivirus family, and picornavirus family. Specific examples include, but are not limited to, canine parvovirus, parvovirus B19, porcine circovirus type 1 and 2, BFDV (Beak and Feather Disease virus, chicken anaemia virus, Polyomavirus, simian virus 40 (SV40), JC virus, BK virus, Budgerigar fledgling disease virus, human papillomavirus, bovine papillomavirus (BPV) type 1, cotton tail rabbit papillomavirus, human adenovirus (HAdV-A, HAdV-B, HAdV-C, HAdV-D, HAdV-E, and HAdV-F), fowl adenovirus A, bovine adenovirus D, frog adenovirus, Reovirus, human orbivirus, human coltivirus, mammalian orthoreovirus, bluetongue virus, rotavirus A, rotaviruses (groups B to G), Colorado tick fever virus, aquareovirus A, cypovirus 1, Fiji disease virus, rice dwarf virus, rice ragged stunt virus, sidnoreovirus 1, mycoreovirus 1, Birnavirus, bursal disease virus, pancreatic necrosis virus, Calicivirus, swine vesicular exanthema virus, rabbit hemorrhagic disease virus, Norwalk virus, Sapporo virus, Picornavirus, human polioviruses (1-3), human coxsackieviruses Al-22, 24 (CAl-22 and CA24, CA23 (echovirus 9)), human coxsackieviruses (B1-6 (CB1-6)), human echoviruses 1-7, 9, 11-27, 29-33, vilyuish virus, simian enteroviruses 1-18 (SEVI-18), porcine enteroviruses 1-11 (PEV1-11), bovine enteroviruses 1-2 (BEVI-2), hepatitis A virus, rhinoviruses, hepatoviruses, cardio viruses, aphthoviruses and echoviruses. The virus may be phage. Examples of phages include, but are not limited to T4, TS, λ, phage, T7 phage, G4, Pl, φ6, *Thermoproteus tenax* virus 1, M13, MS2, Qβ, φX174, Φ29, PZA, Φ15, BS32, B103, M2Y (M2), Nf, GA-I, FWLBc1, FWLBc2, FWLLm3, B4. The reference database may comprise sequences for phage that are pathogenic, protective, or both. In some cases, the virus is selected from a member of the Flaviviridae family (e.g., a member of the Flavivirus, Pestivirus, and Hepacivirus genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofiin virus, Louping ill virus and the Negishi virus; seabird tick-borne viruses, such as the Meaban virus, Saumarez Reef virus, and the Tyuleniy virus; mosquito-borne viruses, such as the Arna virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, *Montana myotis* leukoencephalitis virus, Phnom Penh bat virus, Rio Bravo virus, Tamana bat virus, and the Cell fusing agent virus. In some cases, the virus is selected from a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Whitewater Arroyo virus, Chapare virus, and Lujo virus. In some cases, the virus is selected from a member of the Bunyaviridae family (e.g., a member of the Hantavirus, Nairovirus, Orthobunyavirus, and Phlebovirus genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus. In some cases, the virus is selected from a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the Alphavirus genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O' nyong'nyong virus, and the chikungunya virus; a member of the Poxyiridae family (e.g., a member of the Orthopoxvirus genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or HINI swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picornaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types I and 2), and human T-lymphotropic virus Types I and II (HTLV-1 and HTLV-2, respectively).

Any of the devices and methods described herein can be utilized to detect the presence or absence of nucleic acids associated with one or more fungi in a biological sample. Examples of infectious fungal agents include, without limitation *Aspergillus, Blastomyces, Coccidioides, Cryptococcus, Histoplasma, Paracoccidioides, Sporothrix*, and at least three genera of Zygomycetes. The above fungi, as well as many other fungi, can cause disease in pets and companion animals. The present teaching is inclusive of substrates that contact animals directly or indirectly. Examples of organisms that cause disease in animals include *Malassezia furfur, Epidermophyton floccosur, Trichophyton mentagrophytes, Trichophyton rubrum, Trichophyton tonsurans, Trichophyton equinum, Dermatophilus congolensis, Microsporum canis, Microsporu audouinii, Microsporum gypseum, Mal-*

*assezia ovale, Pseudallescheria, Scopulariopsis, Scedosporium*, and *Candida albicans*. Further examples of fungal infectious agent include, but are not limited to, *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii*, Zygomycetes spp., *Absidia corymbifera, Rhizomucor pusillus*, or *Rhizopus arrhizus*.

Any of the devices and methods described herein can be utilized to detect the presence or absence of nucleic acids associated with one or more parasites in a biological sample. Non-limiting examples of parasites include *Plasmodium, Leishmania, Babesia, Treponema, Borrelia, Trypanosoma, Toxoplasma gondii, Plasmodium falciparum, P. vivax, P. ovale, P. malariae, Trypanosoma* spp., or *Legionella* spp. In some cases, the parasite is *Trichomonas vaginalis*.

What is claimed is:

1. A molecular diagnostic test device, comprising:
   a housing defining an input opening through which a biological sample can be conveyed;
   a detection module within the housing, the detection module defining a detection volume into which the biological sample can be conveyed;
   a reagent within the housing, the reagent formulated to facilitate production of an assay signal indicating a presence of a target polynucleotide sequence within the biological sample; and
   an electronic system within the housing, the electronic system including a photodetector assembly, a memory, a processing device and a digital read module implemented in at least one of the memory or the processing device, the digital read module configured to:
      receive, from the photodetector assembly, a first light signal for a first time period before the biological sample and a reagent are reacted within the detection volume;
      determine a first magnitude associated with the first light signal during the first time period;
      receive, from the photodetector assembly, a second light signal for a second time period after the biological sample and the reagent are reacted within the detection volume of the detection module, the second light signal associated with the assay signal;
      determine a second magnitude associated with the second light signal during the second time period; and
      determine, based on a comparison of the first magnitude and the second magnitude, whether the target polynucleotide sequence is present in the biological sample; the electronic system configured to produce an electronic output when the target polynucleotide sequence is determined to be present in the biological sample.

2. The molecular diagnostic test device of claim 1, wherein:
   the first magnitude is any one of a slope of the first light signal during the first time period or an average intensity of the first light signal during the first time period; and
   the second magnitude is any one of a slope of the second light signal during the second time period or an average intensity of the second light signal during the second time period.

3. The molecular diagnostic test device of claim 1, wherein:
   the housing defines a status opening; and
   the electronic system includes a light output device configured to produce the electronic output, which is a light output, the light output being visible via the status opening.

4. The molecular diagnostic test device of claim 1, wherein:
   the assay signal is a first assay signal;
   the reagent is formulated to facilitate production of a second assay signal indicating the presence of a reference polynucleotide sequence; and
   the digital read module is further configured to:
      receive, from the photodetector assembly, a third light signal for a third time period after the biological sample and the reagent are reacted within the detection volume of the detection module, the third light signal associated with the second assay signal;
      determine a third magnitude associated with the third light signal during the third time period; and
      determine, based on a comparison of the second magnitude and the third magnitude, whether the target polynucleotide sequence is present in the biological sample.

5. The molecular diagnostic test device of claim 4, wherein:
   the reference polynucleotide sequence comprises at least one of a control polynucleotide sequence or an invariant polynucleotide sequence associated with the target polynucleotide sequence.

6. The molecular diagnostic test device of claim 1, wherein:
   the assay signal is a colorimetric signal;
   the detection module includes a detection surface, the colorimetric signal being produced at the detection surface; and
   the electronic system includes a light source, the light source configured to produce a first light beam through the detection module at the detection surface during the first time period and a second light beam through the detection module at the detection surface during the second time period, the first magnitude associated with a first attenuation of the first light beam, the second magnitude associated with a second attenuation of the second light beam.

7. The molecular diagnostic test device of claim 6, wherein:
   the detection module includes a probe adhered to the detection surface, the probe designed to bind an amplicon associated with the target polynucleotide sequence, the colorimetric signal being produced from the detection surface.

8. A computer-implemented method of detecting a presence of a target polynucleotide sequence within a biological sample, the method performed by a molecular diagnostic test device including an electronic system and a detection module, the method comprising:
   receiving, at a photodetector assembly of the electronic system, a first light signal for a first time period after the biological sample and a reagent are reacted within a detection volume of the detection module, the reagent formulated to facilitate production of a first assay signal and a second assay signal, the first assay signal indicating the presence of the target polynucleotide sequence, the second assay signal indicating the presence of a reference polynucleotide sequence, the first light signal associated with the first assay signal;

determining a first magnitude associated with the first light signal during the first time period;

receiving, at the photodetector assembly, a second light signal for a second time period after the biological sample and the reagent are reacted within the detection volume of the detection module, the second light signal associated with the second assay signal;

determining a second magnitude associated with the second light signal during the second time period; and producing an electronic output when a comparison of the first magnitude and the second magnitude indicates that the target polynucleotide sequence is present.

9. The computer-implemented method of claim 8, wherein:

the first magnitude is any one of a slope of the first light signal during the first time period or an average intensity of the first light signal during the first time period; and the second magnitude is any one of a slope of the second light signal during the second time period or an average intensity of the second light signal during the second time period.

10. The computer-implemented method of claim 8, wherein the determining the first magnitude, the determining the second magnitude, and the comparing of the first magnitude and the second magnitude are performed in a digital read module implemented in at least one of a memory or a processing device of the electronic system.

11. The computer-implemented method of claim 8, wherein:

the first assay signal is any one of a colorimetric signal, a chemiluminescence signal, or a fluorescence signal.

12. The computer-implemented method of claim 8, wherein:

the detection module includes a first detection surface and a second detection surface;

the first assay signal is a first colorimetric signal produced at the first detection surface, the first light signal being associated with a first light beam conveyed through the first detection surface, the first magnitude associated with a first attenuation of the first light beam; and the second assay signal is a second colorimetric signal produced at the second detection surface, the second light signal being associated with a second light beam conveyed through the second detection surface, the second magnitude associated with a second attenuation of the second light beam.

13. A molecular diagnostic test device, comprising:

a housing defining an input opening through which a biological sample can be conveyed;

a detection module within the housing, the detection module defining a detection volume into which the biological sample can be conveyed;

a reagent within the housing, the reagent formulated to facilitate production of a colorimetric signal within the detection module after the biological sample and the reagent are reacted within the detection volume, the colorimetric signal indicating a presence of a target polynucleotide sequence within the biological sample; and an electronic system within the housing, the electronic system including a light assembly, a photodetector assembly, a memory, a processing device and a digital read module implemented in at least one of the memory or the processing device, the light assembly positioned on a first side of the detection module, the light assembly configured to produce a light beam that passes through detection volume of the detection module;

the photodetector assembly positioned on the first side of the detection module, the photodetector assembly configured to receive a light signal, the light signal associated with any of a reflection or an attenuation of the light beam; and the digital read module configured to determine a magnitude of the light signal and produce, based on the magnitude, an indication whether the colorimetric signal is present in the detection volume.

14. The molecular diagnostic test device of claim 13, wherein:

the light signal is a first light signal;

the magnitude is a first magnitude; and the digital read module is configured to:

receive, from the photodetector assembly, the first light signal for a first time period before the biological sample and the reagent are reacted within the detection volume;

determine the first magnitude associated with the first light signal during the first time period;

receive, from the photodetector assembly, a second light signal for a second time period after the biological sample and the reagent are reacted within the detection volume of the detection module, the second light signal associated with the colorimetric signal; and determine a second magnitude associated with the second light signal during the second time period; and determine, based on a comparison of the first magnitude and the second magnitude, whether the colorimetric signal is present in the detection volume.

15. The molecular diagnostic test device of claim 13, wherein the electronic system is configured to produce any one of a light output, an audible output, a wireless signal, or a haptic output based on the indication whether the colorimetric signal is present in the detection volume.

16. The molecular diagnostic test device of claim 13, wherein:

the detection module includes a detection flow cell that includes a reflective portion on a second side of the detection module, the reflective portion configured to reflect the light beam produced by the light assembly positioned on the first side of the detection module back towards the photodetector assembly positioned on the first side of the detection module.

17. The molecular diagnostic test device of claim 16, wherein:

the detection flow cell includes a light-blocking portion on a third side of the detection module, the third side of the detection module being nonparallel to the first side and the second side.

18. The molecular diagnostic test device of claim 13, wherein:

the colorimetric signal is a first colorimetric signal;

the light signal is a first light signal;

the light beam is a first light beam;

the magnitude is a first magnitude; and the detection module includes a first detection surface and a second detection surface, the first colorimetric signal being produced at the first detection surface, the reagent formulated to facilitate production of a second colorimetric signal at the second detection surface after the biological sample and the reagent are reacted within the detection volume, the second colorimetric signal indicating the presence of a reference polynucleotide sequence;

the light assembly is configured to produce the first light beam and a second light beam, the first light beam incident upon the first detection surface, the second light beam incident upon the second detection surface;

the photodetector assembly is configured to receive the first light signal and a second light signal, the first light signal associated with any of the reflection or the attenuation of the first light beam, the second light signal associated with any of a reflection or an attenuation of the second light beam; and the digital read module is configured to determine a second magnitude of the second light signal.

19. The molecular diagnostic test device of claim 18, wherein:

a first detection envelope is defined about the first detection surface, the first light beam and the first light signal each being within the first detection envelope; and a second detection envelope is defined about the second detection surface, the second light beam and the second light signal each being within the second detection envelope;

the molecular diagnostic test device further comprising:

a light shield between the first detection envelope and the second detection envelope.

20. The molecular diagnostic test device of claim 19, wherein:

the housing defines a status opening;

the electronic system includes a light output device configured to produce a light output visible via the status opening; and the light shield is a first light shield;

the molecular diagnostic test device further comprising:

a second light shield surrounding at least a portion of the light output device.

21. A computer-implemented method of detecting a presence of a colorimetric signal produced by a molecular diagnostic test device to indicate the presence of a target polynucleotide sequence within a biological sample, the method comprising:

receiving, at a photodetector of an electronic system of the molecular diagnostic test device, a first light signal for a first time period before the biological sample and a reagent are reacted within a detection volume of a detection module of the molecular diagnostic test device, the reagent formulated to facilitate production of the colorimetric signal within the detection volume, the colorimetric signal indicating the presence of the target polynucleotide sequence, the first light signal associated with a light beam conveyed through the detection module and into the detection volume;

determining a first slope of the first light signal during the first time period;

receiving, at the photodetector, a second light signal for a second time period after the biological sample and the reagent are reacted within the detection volume of the detection module, the second light signal associated with the light beam conveyed through the detection module and into the detection volume;

determining a second slope of the second light signal during the second time period; and producing an electronic output indicating the presence of the colorimetric signal when a slope difference between the first slope and the second slope exceeds a predetermined slope threshold.

22. The computer-implemented method of claim 21, wherein the determining the first slope and the determining the second slope is performed in a digital read module implemented in at least one of a memory or a processing device of the electronic system.

23. The computer-implemented method of claim 21, wherein the first light signal and the second light signal are each associated with an attenuation of the light beam through the detection volume of the detection module.

24. The method of claim 21, wherein:

a housing defines a status opening; and the electronic output includes a light output, the light output being visible via the status opening.

25. A molecular diagnostic test device, comprising:

a housing defining an input opening through which a biological sample can be conveyed;

a detection module within the housing, the detection module defining a detection volume into which the biological sample can be conveyed;

a reagent within the housing, the reagent formulated to facilitate production of an assay signal within the detection module after the biological sample and the reagent are reacted within the detection volume, the assay signal indicating a presence of a target polynucleotide sequence within the biological sample; and an electronic system within the housing, the electronic system including:

a sensor configured to produce a sensor signal associated with the assay signal;

a digital read module implemented in at least one of a memory or a processing device, the digital read module configured to determine, based on at least one of an intensity of the sensor signal, a slope of the sensor signal, or a variability of the sensor signal, whether the assay signal is present in the detection volume; and a radio configured to electronically communicate with a computing device via a short-range wireless communication protocol, the radio sending a first wireless signal to establish a communications link between the computing device and the molecular diagnostic test device, the radio sending a second wireless signal indicating whether the assay signal is present.

* * * * *